(12) United States Patent
Migawa et al.

(10) Patent No.: US 9,012,421 B2
(45) Date of Patent: Apr. 21, 2015

(54) BICYCLIC CYCLOHEXOSE NUCLEIC ACID ANALOGS

(75) Inventors: Michael T. Migawa, Carlsbad, CA (US); Punit P. Seth, Carlsbad, CA (US); Eric E. Swayze, Encinitas, CA (US); Bruce S. Ross, Princeton, NJ (US); Quanlai Song, Carlsbad, CA (US); Mingming Han, Nazareth, PA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 534 days.

(21) Appl. No.: 13/388,115

(22) PCT Filed: Aug. 5, 2010

(86) PCT No.: PCT/US2010/044549
§ 371 (c)(1),
(2), (4) Date: Mar. 21, 2012

(87) PCT Pub. No.: WO2011/017521
PCT Pub. Date: Feb. 10, 2011

(65) Prior Publication Data
US 2012/0172414 A1   Jul. 5, 2012

Related U.S. Application Data

(60) Provisional application No. 61/231,885, filed on Aug. 6, 2009.

(51) Int. Cl.
| | |
|---|---|
| A61K 31/712 | (2006.01) |
| C07H 19/06 | (2006.01) |
| C07H 21/00 | (2006.01) |
| C12N 5/071 | (2010.01) |
| C07H 19/16 | (2006.01) |

(52) U.S. Cl.
CPC .............. *C07H 21/00* (2013.01); *C07H 19/06* (2013.01); *C07H 19/16* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan, Jr. |
| 4,415,732 A | 11/1983 | Caruthers et al. |
| 4,458,066 A | 7/1984 | Caruthers et al. |
| 4,469,863 A | 9/1984 | Tso |
| 4,476,301 A | 10/1984 | Imbach |
| 4,500,707 A | 2/1985 | Caruthers et al. |
| 4,668,777 A | 5/1987 | Caruthers et al. |
| 4,725,677 A | 2/1988 | Koster |
| 4,845,205 A | 7/1989 | Huynh Dinh et al. |
| 4,973,679 A | 11/1990 | Caruthers et al. |
| 4,981,957 A | 1/1991 | Lebleu |
| 5,013,830 A | 5/1991 | Ohtsuka |
| 5,023,243 A | 6/1991 | Tullis |
| 5,034,506 A | 7/1991 | Summerton |
| 5,118,800 A | 6/1992 | Smith |
| 5,130,302 A | 7/1992 | Spielvogel |
| 5,132,418 A | 7/1992 | Caruthers et al. |
| 5,134,066 A | 7/1992 | Rogers |
| RE34,036 E | 8/1992 | McGeehan |
| 5,149,797 A | 9/1992 | Pederson |
| 5,166,315 A | 11/1992 | Summerton |
| 5,175,273 A | 12/1992 | Bischofberger |
| 5,177,196 A | 1/1993 | Meyer, Jr. |
| 5,177,198 A | 1/1993 | Spielvogel |
| 5,185,444 A | 2/1993 | Summerton |
| 5,188,897 A | 2/1993 | Suhadolnik |
| 5,194,599 A | 3/1993 | Froehler |
| 5,214,134 A | 5/1993 | Weis |
| 5,216,141 A | 6/1993 | Benner |
| 5,220,007 A | 6/1993 | Pederson |
| 5,235,033 A | 8/1993 | Summerton |
| 5,256,775 A | 10/1993 | Froehler |
| 5,264,423 A | 11/1993 | Cohen |
| 5,264,562 A | 11/1993 | Matteucci |
| 5,264,564 A | 11/1993 | Matteucci |
| 5,276,019 A | 1/1994 | Cohen |
| 5,278,302 A | 1/1994 | Caruthers |
| 5,286,717 A | 2/1994 | Cohen |
| 5,319,080 A | 6/1994 | Leumann |
| 5,321,131 A | 6/1994 | Agrawal |
| 5,359,044 A | 10/1994 | Cook |
| 5,366,878 A | 11/1994 | Pederson |
| 5,367,066 A | 11/1994 | Urdea |
| 5,378,825 A | 1/1995 | Cook |
| 5,386,023 A | 1/1995 | Sanghvi |

(Continued)

FOREIGN PATENT DOCUMENTS

| | | |
|---|---|---|
| WO | WO 94/02499 | 2/1994 |
| WO | WO 94/17093 | 8/1994 |

(Continued)

OTHER PUBLICATIONS

Eschenmoser, Albert, Pure & Applied Chemistry, "Hexose nucleic acids", 1993, vol. 65, No. 6, pp. 1179-1188.*
Zhou, C. et al., Archive for Organic Chemistry, "New methylene-bridged hexopyranosyl nucleoside modified oligonucleotides (BHNA): synthesis and biochemical studies", 2009, vol. iii, pp. 171-186.*
Bass, "Double-stranded RNA as a template for gene silencing" Cell (2000) 101:235-238.
Beaucage et al., "Advances in the Synthesis of Oligonucleotides by the Phosphoramidite Approach" Tetrahedron (1992) 48(12):2223-2311.
Beaucage et al., "The Functionalization of Oligonucleotides Via Phosphoramidite Derivatives" Tetrahedron (1993) 49(10):1925-1963.

(Continued)

*Primary Examiner* — Layla Bland
*Assistant Examiner* — Bahar Craigo
(74) *Attorney, Agent, or Firm* — Isis Pharmaceuticals, Inc. Patent Dept.; Casimir Jones, S.C.

(57) ABSTRACT

The present invention provides bicyclic cyclohexose nucleoside analogs and oligomeric compounds comprising these nucleoside analogs. These bicyclic nucleoside analogs are useful for enhancing properties of oligomeric compounds including nuclease resistance.

29 Claims, No Drawings

(56) References Cited

U.S. PATENT DOCUMENTS

| | | |
|---|---|---|
| 5,393,878 A | 2/1995 | Leumann |
| 5,399,676 A | 3/1995 | Froehler |
| 5,403,711 A | 4/1995 | Walder |
| 5,405,938 A | 4/1995 | Summerton |
| 5,405,939 A | 4/1995 | Suhadolnik |
| 5,432,272 A | 7/1995 | Benner |
| 5,434,257 A | 7/1995 | Matteucci |
| 5,446,137 A | 8/1995 | Maag |
| 5,453,496 A | 9/1995 | Caruthers |
| 5,455,233 A | 10/1995 | Spielvogel |
| 5,457,187 A | 10/1995 | Gmeiner |
| 5,459,255 A | 10/1995 | Cook |
| 5,466,677 A | 11/1995 | Baxter |
| 5,466,786 A | 11/1995 | Buhr |
| 5,470,967 A | 11/1995 | Huie |
| 5,476,925 A | 12/1995 | Letsinger |
| 5,484,908 A | 1/1996 | Froehler |
| 5,489,677 A | 2/1996 | Sanghvi |
| 5,491,133 A | 2/1996 | Walder |
| 5,502,177 A | 3/1996 | Matteucci |
| 5,514,785 A | 5/1996 | Van Ness |
| 5,519,126 A | 5/1996 | Hecht |
| 5,519,134 A | 5/1996 | Acevedo |
| 5,525,711 A | 6/1996 | Hawkins |
| 5,527,899 A | 6/1996 | Froehler |
| 5,536,821 A | 7/1996 | Agrawal |
| 5,541,306 A | 7/1996 | Agrawal |
| 5,541,307 A | 7/1996 | Cook |
| 5,550,111 A | 8/1996 | Suhadolnik |
| 5,552,540 A | 9/1996 | Haralambidis |
| 5,561,225 A | 10/1996 | Maddry |
| 5,563,253 A | 10/1996 | Agrawal |
| 5,565,350 A | 10/1996 | Kmiec |
| 5,565,555 A | 10/1996 | Froehler |
| 5,567,811 A | 10/1996 | Misiura |
| 5,571,799 A | 11/1996 | Tkachuk |
| 5,576,427 A | 11/1996 | Cook |
| 5,587,361 A | 12/1996 | Cook |
| 5,587,469 A | 12/1996 | Cook |
| 5,591,722 A | 1/1997 | Montgomery |
| 5,594,121 A | 1/1997 | Froehler |
| 5,596,086 A | 1/1997 | Matteucci |
| 5,596,091 A | 1/1997 | Switzer |
| 5,597,909 A | 1/1997 | Urdea |
| 5,602,240 A | 2/1997 | De Mesmaeker |
| 5,608,046 A | 3/1997 | Cook |
| 5,610,289 A | 3/1997 | Cook |
| 5,610,300 A | 3/1997 | Altmann |
| 5,614,617 A | 3/1997 | Cook |
| 5,618,704 A | 4/1997 | Sanghvi |
| 5,623,065 A | 4/1997 | Cook |
| 5,623,070 A | 4/1997 | Cook |
| 5,625,050 A | 4/1997 | Beaton |
| 5,627,053 A | 5/1997 | Usman et al. |
| 5,633,360 A | 5/1997 | Bischofberger |
| 5,639,873 A | 6/1997 | Barascut |
| 5,645,985 A | 7/1997 | Froehler |
| 5,646,265 A | 7/1997 | McGee |
| 5,646,269 A | 7/1997 | Matteucci |
| 5,652,355 A | 7/1997 | Metelev |
| 5,652,356 A | 7/1997 | Agrawal |
| 5,663,312 A | 9/1997 | Chaturvedula |
| 5,670,633 A | 9/1997 | Cook |
| 5,672,697 A | 9/1997 | Buhr |
| 5,677,437 A | 10/1997 | Teng |
| 5,677,439 A | 10/1997 | Weis |
| 5,681,941 A | 10/1997 | Cook |
| 5,700,920 A | 12/1997 | Altmann |
| 5,700,922 A | 12/1997 | Cook |
| 5,721,218 A | 2/1998 | Froehler |
| 5,750,692 A | 5/1998 | Cook |
| 5,763,588 A | 6/1998 | Matteucci |
| 5,792,608 A | 8/1998 | Swaminathan |
| 5,792,847 A | 8/1998 | Buhr et al. |
| 5,830,653 A | 11/1998 | Froehler |
| 6,005,096 A | 12/1999 | Matteucci |
| 6,268,490 B1 | 7/2001 | Imanishi et al. |
| 6,426,220 B1 | 7/2002 | Bennett et al. |
| 6,600,032 B1 | 7/2003 | Manoharan et al. |
| 6,770,748 B2 | 8/2004 | Imanishi et al. |
| 6,794,499 B2 | 9/2004 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 2003/0082807 A1 | 5/2003 | Wengel |
| 2003/0207841 A1 | 11/2003 | Kaneko et al. |
| 2003/0224377 A1 | 12/2003 | Wengel et al. |
| 2004/0143114 A1 | 7/2004 | Imanishi et al. |
| 2004/0171570 A1 | 9/2004 | Allerson et al. |
| 2004/0192918 A1 | 9/2004 | Imanishi et al. |
| 2005/0130923 A1 | 6/2005 | Bhat et al. |
| 2007/0287831 A1* | 12/2007 | Seth et al. ............ 536/22.1 |

FOREIGN PATENT DOCUMENTS

| | | |
|---|---|---|
| WO | WO 99/14226 | 3/1999 |
| WO | WO 2005/121371 | 12/2005 |
| WO | WO 2005/121372 | 12/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2009/067647 | 5/2009 |

OTHER PUBLICATIONS

Beaucage et al., "The Synthesis of Specific Ribonucleotides and Unrelated Phosphorylated Biomolecules by the Phosphoramidite Method" Tetrahedron (1993) 49(46):10441-10488.

Brazma et al., "Gene expression data analysis" FEBS Letters (2000) 480:17-24.

Carulli et al., "High Throughput Analysis of Differential Gene Expression" J. Cell. Biochem. Suppl. (1998) 30:286-296.

Celis et al., "Gene expression profiling: monitoring transcription and translation products using DNA microarrays and proteomics" FEBS Lett (2000) 480:2-16.

Chiang et al., "Antisense Oligonucleotides Inhibit Intercellular Adhesion Molecule 1 Expression by Two Distinct Mechanisms" J. Biol. Chem. (1991) 266:18162-18171.

Elbashir, "Duplexes of 21-nucleotide RNAs mediate RNA interference in cultured mammalian cells" Nature (2001) 411:494-498.

Elbashir, "RNA interference is mediated by 21- and 22-nucleotide RNAs" Genes & Devel. (2001) 15:188-200.

Fire et al., "Potent and Specific Genetic Interference by Double-Stranded RNA in *Caenorhabditis elegans*" Nature (1998) 391:806-811.

Fuchs et al., "Identification of Differentially Expressed Genes by Mutually Subtracted RNA Fingerprinting" Anal. Biochem. (2000) 286:91-98.

Gait, "Oligoribonucleotides" Antisense Research and Applications (1993), CRC Press, Boca Raton, pp. 289-301.

Gallo et al., "2'-C-Methyluridine Phosphoramidite: A New Building Block for the Preparation of RNA Analogues Carrying the 2'-Dydroxyl Group" Tetrahedron (2001) 57: 5707-5713.

Going et al., "Molecular Pathology and Future Developments" Eur. J. Cancer (1999) 35:1895-1904.

Jungblut et al., "Proteomics in human disease: Cancer, heart and infections diseases" Electrophoresis (1999) 20:2100-2110.

Jurecic et al., "Long-distance DD-PCR and cDNA microarrays" Curr. Opin. Microbiol. (2000) 3:316-321.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

Kumar et al., "The first analogues of LNA (locked nucleic acids): phosphorothioate-LNA and 2'-thio-LNA" Bioorg Med Chem Lett. (1998) 8:2219-2222.

Larsson et al., "High-throughput protein expression of cDNA products as a tool in functional genomics" J. Biotech. (2000) 80:143-157.

(56) References Cited

OTHER PUBLICATIONS

Madden et al., "Serial analysis of gene expression: from gene discovery to target identification" DDT(2000) 5:415-425.

Montgomery et al., "RNA as a target of double-stranded RNA-mediated genetic interference in *Caenorhabditis elegans*" Proc Natl. Acad. Sci. (1998) 95:15502-7.

Nishikura et al., "A Short Primer on RNAi: RNA-Directed RNA Polymerase Acts as a Key Catalyst" Cell (2001) 107:415-418.

Prashar et al., "READS: A Method for Display of 3'-End Fragment of Restriction Enzyme-Digested cDNAs for Analysis of Differential Gene Expression" Methods Enzymol. (1999) 303:258-272.

Scaringe, "RNA Oligonucleotide Synthesis via 5'-Silyl-2'-Orthoester Chemistry" Methods (2001) 23:206-217.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Sutcliffe et al., "TOGA: An automated parsing technology for analyzing expression of nearly all genes" PNAS (2000) 97:1976-1981.

Tabara et al., "RNAi in *C. elegans*: Soaking in the Genome Sequence" Science (1998) 282:430-431.

Tijsterman et al., "RNA hellcase MUT-14-dependent gene silencing triggered in *C. elegans* by short antisense RNAs" Science (2002) 295:694-7.

Timmons et al., "Specific Interference by Ingested dsRNA" Nature (1998) 395:854.

Timmons et al., "Ingestion of bacterially expressed dsRNAs can produce specific and potent genetic interference in *Caenorhabditis elegans*" Gene (2001) 263:103-112.

To, "Identification of Differential Gene Expression by High Throughput Analysis" Comb. Chem. High Throughput Screen (2000) 3:235-241.

Tuschl et al., "Targeted mRNA degradation by double-stranded RNA in vitro" Genes Dev. (1999) 15:3191-7.

Wahlestedt et al., "Potent and nontoxic antisense oligonucleotide containing locked nucleic acids" Proc. Natl. Acad. Sci. USA (2000) 97: 5633-5638.

Wouters et al., "5-Substituted Pyrimidine 1,5-Anhydrohexitols: Conformational Analysis and Interaction with Viral Thymidine Kinase" Bioorg. Med. Chem. Lett. (1999) 9:1563-1566.

Zhou et al., "Double sugar and phosphate backbone-constrained nucleotides: synthesis, structure, stability and their incorporation into oligodeoxynucleotides" J. Org. Chem. (2009) 74(1):3248-3265.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

International Search Report for application PCT/US2010/044549 dated Mar. 30, 2011.

* cited by examiner

SEQUENCE LISTING

<160> NUMBER OF SEQ ID NOS: 5

<210> SEQ ID NO 1
<211> LENGTH: 3160
<212> TYPE: DNA
<213> ORGANISM: Homo sapiens

<400> SEQUENCE: 1

```
cctcccctcg cccggcgcgg tcccgtccgc ctctcgctcg cctcccgcct ccccctcggtc    60 ttccgaggcg cccgggctcc cggcgcggcg gcggaggggg cgggcaggcc ggcggcggt    120 gatgtggcag gactctttat gcgctgcggc aggatacgcg ctcggcgctg ggacgcgact    180
gcgctcagtt ctctcctctc ggaagctgca gccatgatgg aagtttgaga gttgagccgc    240
tgtgaggcga ggcgggctc aggcgaggga gatgagagac ggcggcggcc gcggcccgga    300
```

```
gccectctca gcgcctgtga gcagccgcgg gggcagcgcc ctcggggagc cggccggcct      360
gcggcggcgg cagcggcggc gtttctcgcc tcctcttcgt cttttctaac cgtgcagcct      420
cttcctcggc ttctcctgaa agggaaggtg aagccgtgg gctcgggcgg gagccggctg      480
aggcgcggcg gcgcggcgg cggcacctcc cgctcctgga gcggggggga gaagcggcgg      540
cggcggcggc cgcggcggct gcagctccag ggaggggtc tgagtcgcct gtcaccattt      600
ccagggctgg gaacgccgga gagttggtct ctcccttct actgcctcca acacggcggc      660
ggcggcggcg gcacatccag ggacccgggc cggttttaaa cctcccgtcc gccgccgccg      720
cacccccgt ggcccgggct ccggaggccg ccggcggagg cagccgttcg gaggattatt      780
cgtcttctcc ccattccgct gccgccgctg ccaggcctct ggctgctgag gagaagcagg      840
cccagtcgct gcaaccatcc agcagccgcc gcagcagcca ttacccggct gcggtccaga      900
gccaagcggc ggcagagcga ggggcatcag ctaccgccaa gtccagagcc atttccatcc      960
tgcagaagaa gccccgccac cagcagcttc tgccatctct ctcctccttt ttcttcagcc     1020
acaggctccc agacatgaca gccatcatca agagatcgt tagcagaaac aaaaggagat     1080
atcaagagga tggattcgac ttagacttga cctatattta tccaaacatt attgctatgg     1140
gatttcctgc agaaagactt gaaggcgtat acaggaacaa tattgatgat gtagtaaggt     1200
ttttggattc aaagcataaa accattaca agatatacaa tctttgtgct gaaagacatt     1260
atgacaccgc caaatttaat tgcagagttg cacaatatcc ttttgaagac ataacccac     1320
cacagctaga acttatcaaa ccctttgtg aagatcttga ccaatggcta agtgaagatg     1380
acaatcatgt tgcagcaatt cactgtaaag ctggaaaggg acgaactggt gtaatgatat     1440
gtgcatattt attacatcgg ggcaaatttt taaaggcaca gaggcccta gatttctatg     1500
gggaagtaag gaccagagac aaaaagggag taactattcc cagtcagagg cgctatgtgt     1560
attattatag ctacctgtta aagaatcatc tggattatag accagtggca ctgttgtttc     1620
acaagatgat gtttgaaact attccaatgt tcagtggcgg aacttgcaat cctcagtttg     1680
tggtctgcca gctaaaggtg aagatatatt cctccaattc aggacccaca cgacgggaag     1740
acaagttcat gtactttgag ttccctcagc cgttacctgt gtgtggtgat atcaaagtag     1800
agttcttcca caaacagaac aagatgctaa aaaaggacaa aatgttttcac ttttgggtaa     1860
atacattctt cataccagga ccagaggaaa cctcagaaaa agtagaaaat ggaagtctat     1920
gtgatcaaga aatcgatagc atttgcagta tagagcgtgc agataatgac aaggaatatc     1980
tagtacttac tttaacaaaa aatgatcttg acaaagcaaa taaagacaaa gccaaccgat     2040
acttttctcc aaatttaag gtgaagctgt acttcacaaa aacagtagag gagccgtcaa     2100
atccagaggc tagcagttca acttctgtaa caccagatgt tagtgacaat gaacctgatc     2160
attatagata ttctgacacc actgactctg atccagagaa tgaacctttt gatgaagatc     2220
agcatacaca aattacaaaa gtctgaattt tttttatca agagggataa acaccatga     2280
aaataaactt gaataaactg aaaatggacc ttttttttt taatggcaat aggacattgt     2340
gtcagattac cagttatagg aacaattctc ttttcctgac caatcttgtt ttaccctata     2400
catccacagg gttttgacac ttgttgtcca gttgaaaaaa ggttgtgtag ctgtgtcatg     2460
tatatacctt tttgtgtcaa aaggacattt aaaattcaat taggattaat aaagatggca     2520
ctttcccgtt ttattccagt tttataaaaa gtgggagacag actgatgtgt atacgtagga     2580
attttttcct tttgtgttct gtcaccaact gaagtggcta aagagctttg tgatatactg     2640
gttcacatcc tacccctttg cacttgtggc aacagataag tttgcagttg gctaagagag     2700
```

-continued

```
gtttccgaaa ggttttgcta ccattctaat gcatgtattc gggttagggc aatggagggg    2760
aatgctcaga aaggaaataa ttttatgctg gactctggac catataccat ctccagctat    2820
ttacacacac ctttctttag catgctacag ttattaatct ggacattcga ggaattggcc    2880
gctgtcactg cttgttgttt gcgcattttt ttttaaagca tattggtgct agaaaaggca    2940
gctaaaggaa gtgaatctgt attggggtac aggaatgaac cttctgcaac atcttaagat    3000
ccacaaatga agggatataa aaataatgtc ataggtaaga aacacagcaa caatgactta    3060
accatataaa tgtggaggct atcaacaaag aatgggcttg aaacattata aaaattgaca    3120
atgatttatt aaatatgttt tctcaattgt aaaaaaaaaa                         3160
```

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2

```
aatggctaag tgaagatgac aatcat                                         26
```

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3

```
tgcacatatc attacaccag ttcgt                                          25
```

<210> SEQ ID NO 4
<211> LENGTH: 30
<212> TYPE: DNA
<213> ORGANISM: Artificial Sequence
<220> FEATURE:
<223> OTHER INFORMATION: Probe

<400> SEQUENCE: 4

```
ttgcagcaat tcactgtaaa gctggaaagg                                     30
```

<210> SEQ ID NO 5
<211> LENGTH: 14
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: 1, 2, 13, 14
<223> OTHER INFORMATION: bases at these positions are RNA

<400> SEQUENCE: 5

```
cutagcactg gccu                                                      14
```

BICYCLIC CYCLOHEXOSE NUCLEIC ACID ANALOGS

CROSS REFERENCED TO RELATED APPLICATIONS

This application is a U.S. National Phase filing under 35 U.S.C. §371 claiming priority to International Application No. PCT/US2010/044549 filed Aug. 5, 2010, which claims priority to U.S. Provisional Application 61/231,885, filed Aug. 6, 2009, each of which is incorporated herein by reference in its entirety.

FIELD OF THE INVENTION

Provided herein are novel bicyclic nucleoside analogs and oligomeric compounds and compositions prepared therefrom. More particularly, bicyclic nucleoside analogs are provided wherein the naturally occurring pentofuranose ring is replaced with a cyclohexyl ring that comprises one ring heteroatom and a bridge making the ring system bicyclic. In certain embodiments, the oligomeric compounds and compositions of the present invention are expected to hybridize to a portion of a target RNA resulting in loss of normal function of the target RNA. The oligomeric compounds provided herein are also expected to be useful as primers and probes in diagnostic applications.

SEQUENCE LISTING

The present application is being filed along with a Sequence Listing in electronic format. The Sequence Listing is provided as a file entitled CHEM0030USASEQ.TXT, created on Jan. 27, 2012 which is 8 Kb in size. The information in the electronic format of the sequence listing is incorporated herein by reference in its entirety.

BACKGROUND OF THE INVENTION

Antisense technology is an effective means for reducing the expression of one or more specific gene products and can therefore prove to be uniquely useful in a number of therapeutic, diagnostic, and research applications. Chemically modified nucleosides are routinely used for incorporation into antisense sequences to enhance one or more properties such as for example nuclease resistance. One such group of chemical modifications includes bicyclic nucleosides wherein the furanose portion of the nucleoside includes a bridge connecting two atoms on the furanose ring thereby forming a bicyclic ring system. Such bicyclic nucleosides have various names including BNA's and LNA's for bicyclic nucleic acids or locked nucleic acids respectively.

Various BNA's have been prepared and reported in the patent literature as well as in scientific literature, see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Wengel et al., PCT International Application WO 98-DK393 19980914; Singh et al., J. Org. Chem., 1998, 63, 10035-10039, the text of each is incorporated by reference herein, in their entirety. Examples of issued US patents and published applications include for example: U.S. Pat. Nos. 7,053,207, 6,770,748, 6,268,490 and 6,794,499 and published U.S. applications 20040219565, 20040014959, 20030207841, 20040192918, 20030224377, 20040143114 and 20030082807; the text of each is incorporated by reference herein, in their entirety.

Many BNA's are toxic. See, e.g., Swayze, E. E.; Siwkowski, A. M.; Wancewicz, E. V.; Migawa, M. T.; Wyrzykiewicz, T. K.; Hung, G.; Monia, B. P.; Bennett, C. F., Antisense oligonucleotides containing locked nucleic acid improve potency but cause significant hepatotoxicity in animals. Nucl. Acids Res., doi: 10.1093/nar/gk11071 (December 2006, advanced online publication).

Many alternative chemically modified nucleosides have been prepared, for instance nucleosides comprising 2' modifications, nucleosides comprising 5' modifications, and nucleosides utilizing non-natural bases. Anhydrohexitol nucleic acids have been prepared (but not as the bicyclic analog, see Wouters and Herdewijn, Bioorg. Med. Chem. Lett., 1999, 9, 1563-1566).

There remains a long-felt need for new agents that specifically regulate gene expression via antisense mechanisms. Disclosed herein are bicyclic cyclohexose nucleic acids and antisense compounds prepared therefrom useful for modulating gene expression pathways, including those relying on mechanisms of action such as RNaseH, RNAi and dsRNA enzymes, as well as other antisense mechanisms based on target degradation or target occupancy. One having skill in the art, once armed with this disclosure will be able, without undue experimentation, to identify, prepare and exploit antisense compounds for these uses.

BRIEF SUMMARY OF THE INVENTION

Provided herein are novel bicyclic nucleoside analogs and oligomeric compounds prepared therefrom. More particularly, the bicyclic nucleoside analogs provided herein have a core structure comprising a cyclohexyl ring wherein one of the ring carbons is replaced with a heteroatom. The cyclohexyl core also includes a bridge connecting two of the ring carbon atoms wherein the two bridging ring carbon atoms have at least one ring carbon atom separating them. In certain embodiments, the oligomeric compounds are expected to hybridize to a portion of a target RNA resulting in loss of normal function of the target RNA. The oligomeric compounds are also expected to be useful as primers and probes in diagnostic applications.

The variables are defined individually in further detail herein. It is to be understood that the bicyclic nucleoside analogs and oligomeric compounds provided herein include all combinations of the embodiments disclosed and variables defined herein.

In certain embodiments, bicyclic nucleoside analogs are provided herein having formula I:

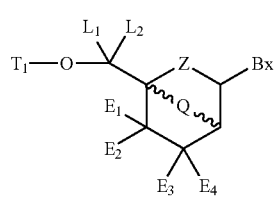

wherein:
Bx is a heterocyclic base moiety;
Z is O or S;
Q is a bridge group comprising 1 or from 2 to 8 linked biradical groups independently selected from O, S, N(R$_1$), $C(R_1)(R_2)$, $C(R_1)=C(R_2)$, $C(R_1)=N$, $C(=NR_1)$, $Si(R_1)_2$, $S(O)_2$, $S(O)$, $C(=O)$ and $C(=S)$;

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$ $NJ_1J_2$, $SJ_1N_3$, $COOJ_1$, acyl (C(=O)—H), substituted acyl, CN, $S(=O)_2$-$J_1$ or $S(=O)$-$J_1$;

$L_1$ and $L_2$ are each, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group;

one of $E_1$ and $E_2$ is H and the other of $E_1$ and $E_2$ is O-$T_2$ or one of $E_3$ and $E_4$ is H and the other of $E_3$ and $E_4$ is O-$T_2$ and the remaining two of $E_1$, $E_2$, $E_3$ and $E_4$ are each, independently, H, halogen, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, $OJ_3$, $NJ_3J_4$, $SJ_3$, $N_3$, $COOJ_3$, acyl (C(=O)—H), substituted acyl, CN, $S(=O)_2$-$J_3$ or $S(=O)$-$J_3$;

one of $T_1$ and $T_2$ is H, a hydroxyl protecting group or a phosphorus moiety and the other of $T_1$ and $T_2$ is H, a hydroxyl protecting group or a reactive phosphorus group;

each substituted group comprises one or more optionally protected substituent groups independently selected from halogen, $OJ_5$, $N(J_5)(J_6)$, $=NJ_5$, $SJ_5$, $N_3$, CN, $OC(=L)J_5$, $OC(=L)N(J_5)(J_6)$ and $C(=L)N(J_5)(J_6)$;

L is O, S or $NJ_7$; and each $J_1$, $J_2$, $J_3$, $J_4$, $J_5$, $J_6$ and $J_7$ is, independently, H, $C_1$-$C_{12}$ alkyl, $C_2$-$C_{12}$ alkenyl, substituted $C_2$-$C_{12}$ alkenyl, $C_2$-$C_{12}$ alkynyl, $C_5$-$C_{20}$ aryl or $C_1$-$C_{12}$ aminoalkyl.

In certain embodiments, each $J_1$, $J_2$, $J_3$, $J_4$, $J_5$, $J_6$ and $J_7$ is, independently, H, $C_1$-$C_{12}$ alkyl, $C_2$-$C_{12}$ alkenyl, $C_2$-$C_{12}$ alkynyl, $C_5$-$C_{20}$ aryl or $C_1$-$C_{12}$ aminoalkyl.

In certain embodiments, each substituted group comprises one or more substituent groups independently selected from halogen, $OJ_5$, $N(J_5)(J_6)$, $=NJ_5$, $SJ_5$, $N_3$, CN, $OC(=L)J_5$, $OC(=L)N(J_5)(J_6)$ and $C(=L)N(J_5)(J_6)$;

L is O, S or $NJ_7$; and each $J_1$, $J_2$, $J_3$, $J_4$, $J_5$, $J_6$ and $J_7$ is, independently, H, $C_1$-$C_6$ alkyl, $C_2$-$C_6$ alkenyl, $C_2$-$C_6$ alkynyl, or $C_1$-$C_6$ aminoalkyl.

In certain embodiments, Bx is uracil, thymine, cytosine, 5-methylcytosine, adenine or guanine.

In certain embodiments, Z is O.

In certain embodiments, one of $E_1$, $E_2$, $E_3$ and $E_4$ is $OT_2$ and the remaining three of $E_1$, $E_2$, $E_3$ and $E_4$ are H. In certain embodiments, one of $E_1$, $E_2$, $E_3$ and $E_4$ is $OT_2$, one of $E_1$, $E_2$, $E_3$ and $E_4$ is H and the remaining two of $E_1$, $E_2$, $E_3$ and $E_4$ are, independently, halogen, $C_1$-$C_6$ alkyl or substituted $C_1$-$C_6$ alkyl. In certain embodiments, one of $E_1$, $E_2$, $E_3$ and $E_4$ is $OT_2$, two of $E_1$, $E_2$, $E_3$ and $E_4$ are H and the remaining one of $E_1$, $E_2$, $E_3$ and $E_4$ is halogen, $C_1$-$C_6$ alkyl or substituted $C_1$-$C_6$ alkyl. In certain embodiments, the remaining of $E_1$, $E_2$, $E_3$ and $E_4$ is, independently, fluoro, methyl or substituted methyl.

In certain embodiments, $L_1$ and $L_2$ are each H. In certain embodiments, one of $L_1$ and $L_2$ is H and the other of $L_1$ and $L_2$ is other than H. In certain embodiments, $L_1$ and $L_2$ are each other than H. In certain embodiments, one of $L_1$ and $L_2$ is substituted $C_1$-$C_6$ alkyl. In certain embodiments, the substituted $C_1$-$C_6$ alkyl comprises at least one substituent group selected from halogen, $C_2$-$C_6$ alkenyl, $OJ_5$, $NJ_5J_6$ and CN, wherein each $J_5$ and $J_6$ is, independently, H or $C_1$-$C_6$ alkyl. In certain embodiments, the substituted $C_1$-$C_6$ alkyl comprises at least one substituent group selected from fluoro and $OCH_3$. In certain embodiments, at least one of $L_1$ and $L_2$ is $C_1$-$C_6$ alkyl. In certain embodiments, one of $L_1$ and $L_2$ is methyl.

In certain embodiments, $T_1$ is selected from acetyl, benzyl, t-butyldimethylsilyl, t-butyldiphenylsilyl and dimethoxytrityl. In certain embodiments, $T_1$ is 4,4'-dimethoxytrityl. In certain embodiments, $T_1$ is a phosphorus moiety. In certain embodiments, $T_2$ is a reactive phosphorus group. In certain embodiments, $T_2$ is a reactive phosphorus group selected from diisopropylcyanoethoxy phosphoramidite and H-phosphonate. In certain embodiments, $T_1$ is 4,4'-dimethoxytrityl and $T_2$ is diisopropylcyanoethoxy phosphoramidite.

In certain embodiments, Q comprises from 2 to 4 of the linked biradical groups. In certain embodiments, Q comprises 2 or 3 of the linked biradical groups. In certain embodiments, Q comprises 1 of the biradical groups. In certain embodiments, Q is $C(R_1)(R_2)$, $C(R_1)(R_2)$—$C(R_1)(R_2)$ or O—$C(R_1)(R_2)$. In certain embodiments, Q is $CH_2$, $(CH_2)_2$ or O—$CH_2$. In certain embodiments, Q is 2'-O—$CH_2$-5'.

In certain embodiments, further bicyclic nucleoside analogs are provided having formula I wherein:

Q is 5'-$CR_3R_4$—O-2', 5'-$CR_3R_4$—S-2', 5'-$CR_3R_4$—N($R_5$)-2', 5'-$(CR_3R_4)_2$-2', 5'-$(CR_3R_4)_3$-2', 5'-$CR_3$=$CR_4$-2', 5'-C(=$CR_3R_4$)—$CR_3R_4$-2', 5'-$CR_3R_4$—C(=$CR_3R_4$)-2', 5'-$CR_3R_4$—$CR_3$=$CR_4$-2', 5'-$CR_3$=$CR_4$—$CR_3R_4$-2', 5'-C(=$CR_3R_4$)—$(CR_3R_4)_2$-2', 5'-$CR_3R_4$—C(=$CR_3R_4$)—$CR_3R_4$-2', 5'-$(CR_3R_4)_2$—C(=$CR_3R_4$)-2', 5'-$CR_3R_4$—O—N($R_5$)-2' or 5'-$CR_3R_4$—N($R_5$)—O-2';

each $R_3$ and $R_4$ is, independently, H, $C_1$-$C_6$ alkyl, substituted $C_1$-$C_6$ alkyl, $C_1$-$C_6$ alkoxy, substituted $C_1$-$C_6$ alkoxy or halogen;

$R_5$ is H, $C_1$-$C_6$ alkyl, substituted $C_1$-$C_6$ alkyl, $C_1$-$C_6$ alkoxy or substituted $C_1$-$C_6$ alkoxy;

$L_1$ and $L_2$ are each, independently, H, $C_1$-$C_6$ alkyl, substituted $C_1$-$C_6$ alkyl, $C_2$-$C_6$ alkenyl or substituted $C_2$-$C_6$ alkenyl;

one of $E_1$ and $E_2$ is H and the other of $E_1$ and $E_2$ is O-$T_2$ or one of $E_3$ and $E_4$ is H and the other of $E_3$ and $E_4$ is O-$T_2$ and the remaining two of $E_1$, $E_2$, $E_3$ and $E_4$ are each, independently, H, $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy or halogen;

one of $T_1$ and $T_2$ is H, a hydroxyl protecting group or a reactive phosphorus group selected from a phosphoramidite, H-phosphonate, phosphate triester and a phosphorus containing chiral auxiliary and the other of $T_1$ and $T_2$ is H, a hydroxyl protecting group or a phosphorus moiety having the formula:

$$R_b = \underset{\underset{R_c}{|}}{\overset{\overset{R_a}{|}}{P}} -$$

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S; and wherein each substituted group comprises one or more optionally protected substituent groups independently selected from $C_1$-$C_6$ alkyl, $C_1$-$C_6$ alkoxy, halogen, hydroxyl, thiol, amino and $C_1$-$C_6$ aminoalkyl.

In certain embodiments, the further bicyclic nucleoside analogs having formula I are provided wherein Bx is uracil, thymine, cytosine, 5-methylcytosine, adenine or guanine.

In certain embodiments, the further bicyclic nucleoside analogs having formula I are provided wherein Z is O.

In certain embodiments, the further bicyclic nucleoside analogs having formula I are provided wherein the remaining two of $E_1$, $E_2$, $E_3$ and $E_4$ are each H. In certain embodiments, one of the remaining two of $E_1$, $E_2$, $E_3$ and $E_4$ is H and the other one of the remaining two of $E_1$, $E_2$, $E_3$ and $E_4$ is $CH_3$, $CH_2CH_3$, $OCH_3$ or F.

In certain embodiments, the further bicyclic nucleoside analogs having formula I are provided wherein $L_1$ and $L_2$ are each H. In certain embodiments, one of $L_1$ and $L_2$ is H and the other of $L_1$ and $L_2$ is $CH_3$ or $OCH_3$.

In certain embodiments, the further bicyclic nucleoside analogs having formula I are provided wherein $T_1$ is a phosphorus moiety. In certain embodiments, $T_1$ is 4,4'-dimethoxytrityl. In certain embodiments, $T_2$ is diisopropylcyanoethoxy phosphoramidite. In certain embodiments, $T_1$ is 4,4'-dimethoxytrityl and $T_2$ is diisopropylcyanoethoxy phosphoramidite.

In certain embodiments, the further bicyclic nucleoside analogs having formula I are provided wherein Q is 5'-$CR_3R_4$—O-2', 5'-$(CR_3R_4)_2$-2', 5'-$CR_3$=$CR_4$-2', 5'-$CR_3R_4$—O—$N(R_5)$-2' or 5'-$CR_3R_4$—$N(R_5)$—O-2'. In certain embodiments, Q is 5'-$CH_2$—O-2'.

In certain embodiments, bicyclic nucleoside analogs having formula I are provided having the configuration:

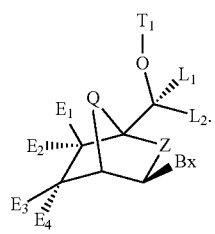

In certain embodiments, bicyclic nucleoside analogs having formula I are provided having the configuration:

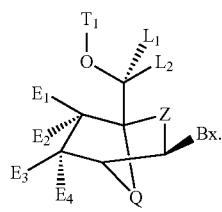

In certain embodiments, bicyclic nucleoside analogs are provided wherein one of $E_1$ and $E_2$ is H and the other of $E_1$ and $E_2$ is O-$T_2$ and the resultant bicyclic nucleoside analog has the configuration:

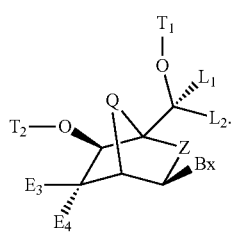

In certain embodiments, bicyclic nucleoside analogs are provided wherein one of $E_1$ and $E_2$ is H and the other of $E_1$ and $E_2$ is O-$T_2$ and the resultant bicyclic nucleoside analog has the configuration:

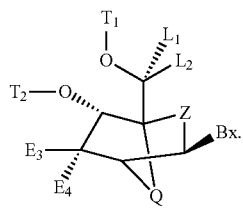

In certain embodiments, bicyclic nucleoside analogs are provided wherein one of $E_3$ and $E_4$ is H and the other of $E_3$ and $E_4$ is O-$T_2$ and the resultant bicyclic nucleoside analog has the configuration:

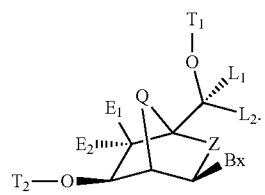

In certain embodiments, bicyclic nucleoside analogs are provided wherein one of $E_3$ and $E_4$ is H and the other of $E_3$ and $E_4$ is O-$T_2$ and the resultant bicyclic nucleoside analog has the configuration:

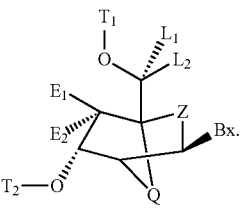

Further provided herein are oligomeric compounds that each comprise at least one bicyclic nucleoside analog of formula II:

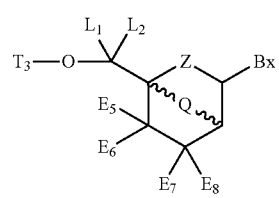

II wherein independently for each bicyclic nucleoside analog of formula II:
Bx is a heterocyclic base moiety;
Z is O or S;
Q is a bridge group comprising 1 or from 2 to 8 linked biradical groups independently selected from O, S, $N(R_1)$, $C(R_1)(R_2)$, $C(R_1)$=$C(R_2)$, $C$(=$NR_1$), $Si(R_1)_2$, $S(O)_2$, $S(O)$, $C$(=O) and $C$(=S);
each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$ $NJ_1J_2$, $SJ_1N_3$, $COOJ_1$, acyl (C(=O)—H), substituted acyl, CN, S(=O)$_2$-$J_1$ or S(=O)-$J_1$;

$L_1$ and $L_2$ are each, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group;

one of $E_5$ and $E_6$ is H and the other of $E_5$ and $E_6$ is O-$T_4$ or one of $E_7$ and $E_8$ is H and the other of $E_7$ and $E_8$ is O-$T_4$ and the remaining two of $E_5$, $E_6$, $E_7$ and $E_8$ are each, independently, H, halogen, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, $OJ_3$, $NJ_3J_4$, $SJ_3$, $N_3$, $COOJ_3$, acyl (C(=O)—H), substituted acyl, CN, S(=O)$_2$-$J_3$ or S(=O)-$J_3$;

one of $T_3$ and $T_4$ is an internucleoside linking group linking the bicyclic nucleoside analog to the oligomeric compound and the other of $T_3$ and $T_4$ is H, a protecting group, a phosphorus moiety, a 5' or 3'-terminal group or an internucleoside linking group linking the bicyclic nucleoside analog to the oligomeric compound;

each substituted group comprises one or more optionally protected substituent groups independently selected from halogen, $OJ_5$, $N(J_5)(J_6)$, =$NJ_5$, $SJ_5$, $N_3$, CN, OC(=L)$J_5$, OC(=L)N($J_5$)($J_6$) and C(=L)N($J_5$)($J_6$);

L is O, S or $NJ_7$; and each $J_1$, $J_2$, $J_3$, $J_4$, $J_5$, and $J_7$ is, independently, H, $C_1$-$C_{12}$ alkyl, $C_2$-$C_{12}$ alkenyl, substituted $C_2$-$C_{12}$ alkenyl $C_2$-$C_{12}$ alkynyl, $C_5$-$C_{20}$ aryl or $C_1$-$C_{12}$ aminoalkyl.

In certain embodiments, each $J_1$, $J_2$, $J_3$, $J_4$, $J_5$, $J_6$ and $J_7$ is, independently, H, $C_1$-$C_{12}$ alkyl, $C_2$-$C_{12}$ alkenyl, $C_2$-$C_{12}$ alkynyl, $C_5$-$C_{20}$ aryl or $C_1$-$C_{12}$ aminoalkyl.

In certain embodiments, each substituted group comprises one or more substituent groups independently selected from halogen, $OJ_5$, $N(J_5)(J_6)$, =$NJ_5$, $SJ_5$, $N_3$, CN, OC(=L)$J_5$, OC(=L)N($J_5$)($J_6$) and C(=L)N($J_5$)($J_6$);

L is O, S or $NJ_7$; and each $J_1$, $J_2$, $J_3$, $J_4$, $J_5$, $J_6$ and $J_7$ is, independently, H, $C_1$-$C_6$ alkyl, $C_2$-$C_6$ alkenyl, $C_2$-$C_6$ alkynyl, or $C_1$-$C_6$ aminoalkyl.

In certain embodiments, oligomeric compounds are provided wherein independently for each bicyclic nucleoside analog of formula II, Bx is uracil, thymine, cytosine, 5-methylcytosine, adenine or guanine.

In certain embodiments, oligomeric compounds are provided wherein independently for each bicyclic nucleoside analog of formula II Z is O.

In certain embodiments, oligomeric compounds are provided wherein independently for each bicyclic nucleoside analog of formula II one of $E_5$, $E_6$, $E_7$ and $E_8$ is $OT_4$ and the remaining three of $E_5$, $E_6$, $E_7$ and $E_8$ are H. In certain embodiments, oligomeric compounds are provided wherein independently for each bicyclic nucleoside analog of formula II one of $E_5$, $E_6$, $E_7$ and $E_8$ is $OT_4$, one of $E_5$, $E_6$, $E_7$ and $E_8$ is H and the remaining two of $E_5$, $E_6$, $E_7$ and $E_8$ are, independently, halogen, $C_1$-$C_6$ alkyl or substituted $C_1$-$C_6$ alkyl. In certain embodiments, oligomeric compounds are provided wherein independently for each bicyclic nucleoside analog of formula II one of $E_5$, $E_6$, $E_7$ and $E_8$ is $OT_4$, two of $E_5$, $E_6$, $E_7$ and $E_8$ are H and the remaining one of $E_5$, $E_6$, $E_7$ and $E_8$ is halogen, $C_1$-$C_6$ alkyl or substituted $C_1$-$C_6$ alkyl. In certain embodiments, oligomeric compounds are provided wherein independently for each bicyclic nucleoside analog of formula II the remaining of $E_5$, $E_6$, $E_7$ and $E_8$ is, independently, fluoro, methyl or substituted methyl.

In certain embodiments, oligomeric compounds are provided wherein independently for each bicyclic nucleoside analog of formula II $L_1$ and $L_2$ are each H. In certain embodiments, oligomeric compounds are provided wherein independently for each bicyclic nucleoside analog of formula II one of $L_1$ and $L_2$ is H and the other of $L_1$ and $L_2$ is other than H. In certain embodiments, oligomeric compounds are provided wherein independently for each bicyclic nucleoside analog of formula II $L_1$ and $L_2$ are each other than H. In certain embodiments, oligomeric compounds are provided wherein independently for each bicyclic nucleoside analog of formula II one of $L_1$ and $L_2$ is substituted $C_1$-$C_6$ alkyl. In certain embodiments, oligomeric compounds are provided wherein independently for each bicyclic nucleoside analog of formula II the substituted $C_1$-$C_6$ alkyl comprises at least one substituent group selected from halogen, $C_2$-$C_6$ alkenyl, $OJ_5$, $NJ_5J_6$ and CN, wherein each $J_5$ and $J_6$ is, independently, H or $C_1$-$C_6$ alkyl. In certain embodiments, oligomeric compounds are provided wherein independently for each bicyclic nucleoside analog of formula II the substituted $C_1$-$C_6$ alkyl comprises at least one substituent group selected from fluoro and $OCH_3$. In certain embodiments, oligomeric compounds are provided wherein independently for each bicyclic nucleoside analog of formula II at least one of $L_1$ and $L_2$ is $C_1$-$C_6$ alkyl. In certain embodiments, oligomeric compounds are provided wherein independently for each bicyclic nucleoside analog of formula II one of $L_1$ and $L_2$ is methyl.

In certain embodiments, oligomeric compounds are provided wherein at least one of $T_3$ and $T_4$ is a 5' or 3'-terminal group. In certain embodiments, oligomeric compounds are provided wherein one $T_3$ is a phosphorus moiety. In certain embodiments, the phosphorus moiety has the formula:

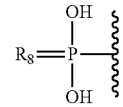

wherein $R_8$ is O or S.

In certain embodiments, oligomeric compounds are provided wherein one $T_3$ is H and one $T_4$ is H.

In certain embodiments, oligomeric compounds are provided wherein independently for each bicyclic nucleoside analog of formula II Q comprises from 2 to 4 of said linked biradical groups. In certain embodiments, oligomeric compounds are provided wherein independently for each bicyclic nucleoside analog of formula II Q comprises 2 or 3 of said linked biradical groups. In certain embodiments, oligomeric compounds are provided wherein independently for each bicyclic nucleoside analog of formula II Q comprises 1 of said biradical groups. In certain embodiments, oligomeric compounds are provided wherein independently for each bicyclic nucleoside analog of formula II Q is C($R_1$)($R_2$), C($R_1$)($R_2$)—C($R_1$)($R_2$) or O—C($R_1$)($R_2$). In certain embodiments, oligomeric compounds are provided wherein independently for each bicyclic nucleoside analog of formula II Q is $CH_2$, $(CH_2)_2$ or O—$CH_2$. In certain embodiments, oligomeric compounds are provided wherein independently for each bicyclic nucleoside analog of formula II Q is 2'-O—$CH_2$-5'.

In certain embodiments, further oligomeric compounds comprising at least one bicyclic nucleoside analog of formula II are provided wherein independently for each bicyclic nucleoside analog of formula II:

Q is 5'-$CR_3R_4$—O-2', 5'-$CR_3R_4$—S-2', 5'-$CR_3R_4$—N($R_5$)-2', 5'-$(CR_3R_4)_2$-2', 5'-$(CR_3R_4)_3$-2', 5'-$CR_3$=$CR_4$-2', 5'-C(=$CR_3R_4$)—$CR_3R_4$-2', 5'-$CR_3R_4$—C(=$CR_3R_4$)-2', 5'-$CR_3R_4$—$CR_3$=$CR_4$-2', 5'-$CR_3$=$CR_4$—$CR_3R_4$-2', 5'-C(=$CR_3R_4$)—$(CR_3R_4)_2$-2', 5'-$CR_3R_4$—C(=$CR_3R_4$)—$CR_3R_4$-2', 5'-$(CR_3R_4)_2$—C(=$CR_3R_4$)-2', 5'-$CR_3R_4$—O—N($R_5$)-2' or 5'-$CR_3R_4$—N($R_5$)—O-2;

each $R_3$ and $R_4$ is, independently, H, $C_1$-$C_6$ alkyl, substituted $C_1$-$C_6$ alkyl, $C_1$-$C_6$ alkoxy, substituted $C_1$-$C_6$ alkoxy or halogen;

$R_5$ is H, $C_1$-$C_6$ alkyl, substituted $C_1$-$C_6$ alkyl, $C_1$-$C_6$ alkoxy or substituted $C_1$-$C_6$ alkoxy;

$L_1$ and $L_2$ are each, independently, H, $C_1$-$C_6$ alkyl, substituted $C_1$-$C_6$ alkyl, $C_2$-$C_6$ alkenyl or substituted $C_2$-$C_6$ alkenyl;

one of $E_5$ and $E_6$ is H and the other of $E_5$ and $E_6$ is O-$T_4$ or one of $E_7$ and $E_8$ is H and the other of $E_7$ and $E_8$ is O-$T_4$ and the remaining two of $E_5$, $E_6$, $E_7$ and $E_8$ are each, independently, H, $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy or halogen; and wherein each substituted group comprises one or more optionally protected substituent groups independently selected from $C_1$-$C_6$ alkyl, $C_1$-$C_6$ alkoxy, halogen, hydroxyl, thiol, amino and $C_1$-$C_6$ aminoalkyl.

In certain embodiments, the further oligomeric compounds are provided wherein independently for each bicyclic nucleoside analog of formula II Bx uracil, thymine, cytosine, 5-methylcytosine, adenine or guanine.

In certain embodiments, the further oligomeric compounds are provided wherein independently for each bicyclic nucleoside analog of formula II Z is O.

In certain embodiments, the further oligomeric compounds are provided wherein independently for each bicyclic nucleoside analog of formula II the remaining two of $E_5$, $E_6$, $E_7$ and $E_8$ are each H for each bicyclic nucleoside of formula II. In certain embodiments, the further oligomeric compounds are provided wherein independently for each bicyclic nucleoside analog of formula II one of the remaining two of $E_1$, $E_2$, $E_3$ and $E_4$ is H and the other one of the remaining two of $E_1$, $E_2$, $E_3$ and $E_4$ is $CH_3$, $CH_2CH_3$, $OCH_3$ or F.

In certain embodiments, the further oligomeric compounds are provided wherein independently for each bicyclic nucleoside analog of formula II $L_1$ and $L_2$ are each H.

In certain embodiments, the further oligomeric compounds are provided wherein independently for each bicyclic nucleoside analog of formula II one of $L_1$ and $L_2$ is H and the other of $L_1$ and $L_2$ is $CH_3$ or $OCH_3$.

In certain embodiments, the further oligomeric compounds are provided wherein one $T_3$ is a phosphorus moiety.

In certain embodiments, the further oligomeric compounds are provided wherein independently for each bicyclic nucleoside analog of formula II Q is 5'-$CR_3R_4$—O-2', 5'-$(CR_3R_4)_2$-2', 5'-$CR_3$=$CR_4$-2', 5'-$CR_3R_4$—O—N($R_5$)-2' or 5'-$CR_3R_4$—N($R_5$)—O-2'. In certain embodiments, the further oligomeric compounds are provided wherein for each bicyclic nucleoside analog of formula II Q is 5'-$CH_2$—O-2'.

In certain embodiments, each of the further oligomeric compounds are provided comprising one phosphorus moiety having the formula:

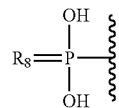

wherein $R_8$ is O or S.

In certain embodiments, oligomeric compounds comprising at least one bicyclic nucleoside analog of formula II are provided wherein each bicyclic nucleoside analog of formula II has the configuration:

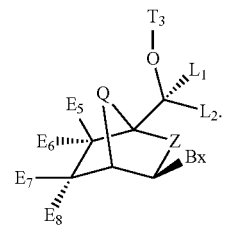

In certain embodiments, oligomeric compounds comprising at least one bicyclic nucleoside analog of formula II are provided wherein each bicyclic nucleoside analog of formula II has the configuration:

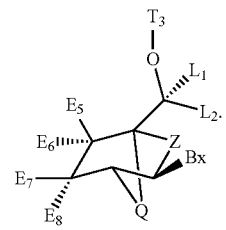

In certain embodiments, oligomeric compounds are provided wherein independently for each bicyclic nucleoside analog of formula II one of $E_5$ and $E_6$ is H and the other of $E_5$ and $E_6$ is O-$T_4$ having the configuration:

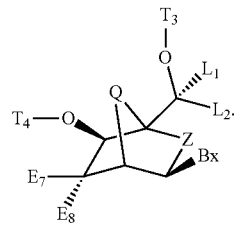

In certain embodiments, oligomeric compounds are provided wherein independently for each bicyclic nucleoside analog of formula II one of $E_5$ and $E_6$ is H and the other of $E_5$ and $E_6$ is O-$T_4$ having the configuration:

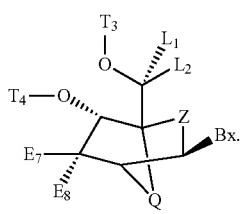

In certain embodiments, oligomeric compounds are provided wherein independently for each bicyclic nucleoside analog of formula II one of $E_7$ and $E_8$ is H and the other of $E_7$ and $E_8$ is O-$T_4$ having the configuration:

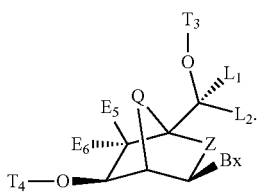

In certain embodiments, oligomeric compounds are provided wherein independently for each bicyclic nucleoside analog of formula II one of $E_7$ and $E_8$ is H and the other of $E_7$ and $E_8$ is O-$T_4$ having the configuration:

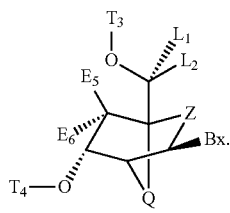

In certain embodiments, oligomeric compounds are provided wherein at least one bicyclic nucleoside analog of formula II is located at the 5' end.

In certain embodiments, oligomeric compounds are provided comprising at least one region having at least 2 contiguous bicyclic nucleoside analogs of formula II. In certain embodiments, the at least one region comprises from 2 to 5 contiguous bicyclic nucleoside analogs of formula II.

In certain embodiments, oligomeric compounds are provided comprising at least two regions wherein each region independently comprises from 1 to about 5 contiguous bicyclic nucleoside analogs of formula II and wherein each region is separated by at least one monomer subunit that is different from the bicyclic nucleoside analogs of formula II and is independently selected from nucleosides and modified nucleosides. In certain embodiments, oligomeric compounds are provided comprising a gapped oligomeric compound wherein one region of contiguous bicyclic nucleoside analogs of formula II is located at the 5'-end and a second region of contiguous bicyclic nucleoside analogs of Formula II is located at the 3'-end, wherein the two regions are separated by an internal region comprising from about 6 to about 18 monomer subunits independently selected from nucleosides and modified nucleosides that are different from the bicyclic nucleoside analogs of formula II. In certain embodiments, the internal region comprises from about 8 to about 14 contiguous β-D-2'-deoxyribofuranosyl nucleosides. In certain embodiments, the internal region comprises from about 9 to about 12 contiguous β-D-2'-deoxyribofuranosyl nucleosides.

In certain embodiments, oligomeric compounds are provided comprising one region of from 2 to 3 contiguous bicyclic nucleoside analogs of formula II, an optional second region of from 1 to 3 contiguous bicyclic nucleoside analogs of formula II and a third region of from 8 to 14 β-D-2'-deoxyribofuranosyl nucleosides wherein said third region is located between said first and said second regions.

In certain embodiments, oligomeric compounds are provided wherein each internucleoside linking group is, independently, a phosphodiester internucleoside linking group or a phosphorothioate internucleoside linking group. In certain embodiments, oligomeric compounds are provided wherein essentially each internucleoside linking group is a phosphorothioate internucleoside linking group.

In certain embodiments, oligomeric compounds are provided comprising from about 8 to about 40 monomer subunits in length. In certain embodiments, oligomeric compounds are provided comprising from about 8 to about 20 monomer subunits in length. In certain embodiments, oligomeric compounds are provided comprising from about 10 to about 16 monomer subunits in length. In certain embodiments, oligomeric compounds are provided comprising from about 0 to about 14 monomer subunits in length.

Also provided herein are bicyclic nucleoside analogs wherein each bicyclic nucleoside analog comprises a 6 membered ring having 5 carbon atoms and one heteroatom selected from oxygen, sulfur or substituted amino, wherein a first ring carbon flanking the ring heteroatom is substituted with a nucleobase and the opposite flanking ring carbon is substituted with a first group that can form an internucleoside linkage; one additional ring carbon is substituted with a second group that can form an internucleoside linkage; and wherein said 6 membered ring comprises a bridge connecting two ring carbon atoms of said six membered ring wherein the two ring atoms are separated by at least one additional ring atom. In certain embodiments, each of the groups that can form an internucleoside linkage is, independently, hydroxyl, protected hydroxyl, hydroxymethylene, protected hydroxymethylene or a reactive phosphorus group. In certain embodiments, the bridge comprises a single atom between said two ring carbons thereby having a 2.2.1. bicyclic ring structure. In certain embodiments, the bridge comprises two atoms between said two ring carbons thereby having a 2.2.2. bicyclic ring structure. In certain embodiments, oligomeric compounds are provided comprising at least one of these bicyclic nucleoside analogs.

Also provided herein are methods of inhibiting gene expression comprising contacting one or more cells, a tissue or an animal with an oligomeric compound as provided herein.

In certain embodiments, oligomeric compounds are provided herein for use in an in vivo method of inhibiting gene expression said method comprising contacting one or more cells, a tissue or an animal with an oligomeric compound as provided herein.

In certain embodiments, oligomeric compounds as provided herein are used in medical therapy.

DETAILED DESCRIPTION OF THE INVENTION

Provided herein are novel bicyclic nucleosides and oligomeric compounds prepared therefrom. More particularly, the bicyclic nucleosides each have a core structure comprising a cyclohexyl ring wherein one of the ring carbons is replaced with a heteroatom. Attached to one of the two carbon atoms flanking the heteroatom is a heterocyclic base moiety and attached to the other flanking carbon atom is a first group capable of forming an internucleoside linkage. A second group capable of forming an internucleoside linkage is adjacent to or one atom removed from the first group capable of forming an internucleoside linkage. The core six membered ring system further comprises a bridge connecting two of the ring carbon atoms wherein the two bridging ring carbon atoms have at least one ring carbon atom separating them.

The bridge forming the second ring is variable comprising a single biradical group such as for example a methylene or substituted methylene group or up to about 8 biradical groups linked together. Biradical groups that can be used individually or linked together to form larger bridging groups include, but are not limited to: O, S, $N(R_1)$, $C(R_1)(R_2)$, $C(R_1)=C(R_2)$, $C(R_1)=N$, $C(=NR_1)$, $Si(R_1)_2$, $SO_2$, SO, $C(=O)$ and $C(=S)$ where $R_1$ and $R_2$ are as listed above. The conformation (α or β) of the bicyclic nucleosides can also be varied by choosing the route of synthesis to place the bridge above the plane of the 6 membered ring system or below it.

The groups capable of forming internucleoside linkages can be variable. Preferred groups capable of forming internucleoside linkages include optionally protected primary and secondary alcohols and reactive phosphorus groups such as phosphoramidites and H-phosphonates. In one preferred embodiment one of the groups capable of forming an internucleoside linkage is an optionally protected hydroxymethylene and the other group is an optionally protected hydroxyl or reactive phosphorus group.

In certain embodiments, the bicyclic nucleosides are expected to be useful for enhancing desired properties of oligomeric compounds in which they are incorporated such as for example nuclease resistance. In certain embodiments, the oligomeric compounds provided herein are expected to hybridize to a portion of a target RNA resulting in loss of normal function of the target RNA. The oligomeric compounds provided herein are also expected to be useful as primers and probes in diagnostic applications. In certain embodiments, bicyclic nucleosides of the present invention have formula I shown below:

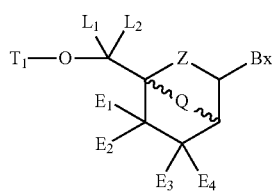

wherein:
Bx is a heterocyclic base moiety;
Z is O or S;
Q is a bridge group comprising 1 or from 2 to 8 linked biradical groups independently selected from O, S, $N(R_1)$, $C(R_1)(R_2)$, $C(R_1)=C(R_2)$, $C(R_1)=N$, $C(=NR_1)$, $Si(R_1)_2$, $S(O)_2$, S(O), $C(=O)$ and $C(=S)$;
each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $SJ_1$, $N_3$, $COOJ_1$, acyl ($C(=O)$—H), substituted acyl, CN, $S(=O)_2$-$J_1$ or $S(=O)$-$J_1$;

$L_1$ and $L_2$ are each, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl ($C(=O)$—H), substituted acyl, a heterocycle radical, a substituted heterocycle radical, $C_1$-$C_{12}$ aminoalkyl, substituted $C_1$-$C_{12}$ aminoalkyl or a protecting group;

one of $E_1$ and $E_2$ is H and the other of $E_1$ and $E_2$ is $O$-$T_2$ or one of $E_3$ and $E_4$ is H and the other of $E_3$ and $E_4$ is $O$-$T_2$ and the remaining two of $E_1$, $E_2$, $E_3$ and $E_4$ are each, independently, H, halogen, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, $OJ_3$, $NJ_3J_4$, $SJ_3$, $N_3$, $COOJ_3$, acyl ($C(=O)$—H), substituted acyl, CN, $S(=O)_2$-$J_3$ or $S(=O)$-$J_3$;

one of $T_1$ and $T_2$ is H, a hydroxyl protecting group or a phosphorus moiety and the other of $T_1$ and $T_2$ is H, a hydroxyl protecting group or a reactive phosphorus group;

each substituted group comprises one or more optionally protected substituent groups independently selected from halogen, $OJ_5$, $N(J_5)(J_6)$, $=NJ_5$, $SJ_5$, $N_3$, CN, $OC(=L)J_5$, $OC(=L)N(J_5)(J_6)$ and $C(=L)N(J_5)(J_6)$;

L is O, S or $NJ_7$; and each $J_1$, $J_2$, $J_3$, $J_4$, $J_5$, $J_6$ and $J_7$ is, independently, H, $C_1$-$C_{12}$ alkyl, $C_2$-$C_{12}$ alkenyl, substituted $C_2$-$C_{12}$ alkenyl, $C_2$-$C_{12}$ alkynyl, $C_5$-$C_{20}$ aryl or $C_1$-$C_{12}$ aminoalkyl.

In certain embodiments, further bicyclic nucleoside analogs are provided having formula I wherein:

Q is 5'-$CR_3R_4$—O-2', 5'-$CR_3R_4$—S-2', 5'-$CR_3R_4$—$N(R_5)$-2', 5'-$(CR_3R_4)_2$-2', 5'-$(CR_3R_4)_3$-2', 5'-$CR_3$=$CR_4$-2', 5'-C($=CR_3R_4$)—$CR_3R_4$-2', 5'-$CR_3R_4$—C($=CR_3R_4$)-2', 5'-$CR_3R_4$—$CR_3$=$CR_4$-2', 5'-$CR_3$=$CR_4$—$CR_3R_4$-2', 5'-C($=CR_3R_4$)—$(CR_3R_4)_2$-2', 5'-$CR_3R_4$—C($=CR_3R_4$)—$CR_3R_4$-2', 5'-$(CR_3R_4)_2$—C($=CR_3R_4$)-2', 5'-$CR_3R_4$—O—N($R_5$)-2' or 5'-$CR_3R_4$—N($R_5$)—O-2;

each $R_3$ and $R_4$ is, independently, H, $C_1$-$C_6$ alkyl, substituted $C_1$-$C_6$ alkyl, $C_1$-$C_6$ alkoxy, substituted $C_1$-$C_6$ alkoxy or halogen;

$R_5$ is H, $C_1$-$C_6$ alkyl, substituted $C_1$-$C_6$ alkyl, $C_1$-$C_6$ alkoxy or substituted $C_1$-$C_6$ alkoxy;

$L_1$ and $L_2$ are each, independently, H, $C_1$-$C_6$ alkyl, substituted $C_1$-$C_6$ alkyl, $C_2$-$C_6$ alkenyl or substituted $C_2$-$C_6$ alkenyl;

one of $E_1$ and $E_2$ is H and the other of $E_1$ and $E_2$ is $O$-$T_2$ or one of $E_3$ and $E_4$ is H and the other of $E_3$ and $E_4$ is $O$-$T_2$ and the remaining two of $E_1$, $E_2$, $E_3$ and $E_4$ are each, independently, H, $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy or halogen;

one of $T_1$ and $T_2$ is H, a hydroxyl protecting group or a reactive phosphorus group selected from a phosphoramidite, H-phosphonate, phosphate triester and a phosphorus containing chiral auxiliary and the other of $T_1$ and $T_2$ is H, a hydroxyl protecting group or a phosphorus moiety having the formula:

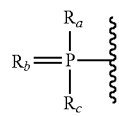

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S; and wherein each substituted group comprises one or more optionally protected substituent groups independently selected from $C_1$-$C_6$ alkyl, $C_1$-$C_6$ alkoxy, halogen, hydroxyl, thiol, amino and $C_1$-$C_6$ aminoalkyl.

In certain embodiments, oligomeric compounds are provided comprising at least one bicyclic nucleoside analog of formula II:

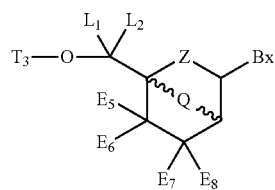

II wherein independently for each bicyclic nucleoside analog of formula II:

Bx is a heterocyclic base moiety;

Z is O or S;

Q is a bridge group comprising 1 or from 2 to 8 linked biradical groups independently selected from O, S, N($R_1$), C($R_1$)($R_2$), C($R_1$)=C($R_2$), C($R_1$)=N, C(=$NR_1$), Si($R_1$)$_2$, S(O)$_2$, S(O), C(=O) and C(=S);

each $R_1$ and $R_2$ is, independently, H, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, S(=O)$_2$-$J_1$ or S(=O)-$J_1$;

$L_1$ and $L_2$ are each, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group;

one of $E_5$ and $E_6$ is H and the other of $E_5$ and $E_6$ is O-$T_4$ or one of $E_7$ and $E_8$ is H and the other of $E_7$ and $E_8$ is O-$T_4$ and the remaining two of $E_5$, $E_6$, $E_7$ and $E_8$ are each, independently, H, halogen, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, a heterocycle radical, a substituted heterocycle radical, heteroaryl, substituted heteroaryl, $C_5$-$C_7$ alicyclic radical, substituted $C_5$-$C_7$ alicyclic radical, $OJ_3$, $NJ_3J_4$, $SJ_3$, $N_3$, $COOJ_3$, acyl (C(=O)—H), substituted acyl, CN, S(=O)$_2$-$J_3$ or S(=O)-$J_3$;

one of $T_3$ and $T_4$ is an internucleoside linking group linking the bicyclic nucleoside analog to the oligomeric compound and the other of $T_3$ and $T_4$ is H, a protecting group, a phosphorus moiety, a 5' or 3'-terminal group or an internucleoside linking group linking the bicyclic nucleoside analog to the oligomeric compound;

each substituted group comprises one or more optionally protected substituent groups independently selected from halogen, $OJ_5$, $N(J_5)(J_6)$, =$NJ_5$, $SJ_5$, $N_3$, CN, OC(=L)$J_5$, OC(=L)N($J_5$)($J_6$) and C(=L)N($J_5$)($J_6$);

L is O, S or $NJ_7$; and each $J_1$, $J_2$, $J_3$, $J_4$, $J_5$, $J_6$ and $J_7$ is, independently, H, $C_1$-$C_{12}$ alkyl, $C_2$-$C_{12}$ alkenyl, substituted $C_2$-$C_{12}$ alkenyl, $C_2$-$C_{12}$ alkynyl, $C_5$-$C_{20}$ aryl or $C_1$-$C_{12}$ aminoalkyl. In certain embodiments, further oligomeric compounds comprising at least one bicyclic nucleoside analog of formula II are provided wherein independently for each bicyclic nucleoside analog of formula II:

Q is 5'-$CR_3R_4$—O-2', 5'-$CR_3R_4$—S-2', 5'-$CR_3R_4$—N($R_5$)-2', 5'-($CR_3R_4$)$_2$-2', 5'-($CR_3R_4$)$_3$-2', 5'-$CR_3$=$CR_4$-2', 5'-C(=$CR_3R_4$)—$CR_3R_4$-2', 5'-$CR_3R_4$—C(=$CR_3R_4$)-2', 5'-$CR_3R_4$—$CR_3$=$CR_4$-2', 5'-$CR_3$=$CR_4$—$CR_3R_4$-2', 5'-C(=$CR_3R_4$)—($CR_3R_4$)$_2$-2', 5'-$CR_3R_4$—C(=$CR_3R_4$)—$CR_3R_4$-2', 5'-($CR_3R_4$)$_2$—C(=$CR_3R_4$)-2', 5'-$CR_3R_4$—O—N($R_5$)-2' or 5'-$CR_3R_4$—N($R_5$)—O-2;

each $R_3$ and $R_4$ is, independently, H, $C_1$-$C_6$ alkyl, substituted $C_1$-$C_6$ alkyl, $C_1$-$C_6$ alkoxy, substituted $C_1$-$C_6$ alkoxy or halogen;

$R_5$ is H, $C_1$-$C_6$ alkyl, substituted $C_1$-$C_6$ alkyl, $C_1$-$C_6$ alkoxy or substituted $C_1$-$C_6$ alkoxy;

$L_1$ and $L_2$ are each, independently, H, $C_1$-$C_6$ alkyl, substituted $C_1$-$C_6$ alkyl, $C_2$-$C_6$ alkenyl or substituted $C_2$-$C_6$ alkenyl;

one of $E_5$ and $E_6$ is H and the other of $E_5$ and $E_6$ is O-$T_4$ or one of $E_7$ and $E_8$ is H and the other of $E_7$ and $E_8$ is O-$T_4$ and the remaining two of $E_5$, $E_6$, $E_7$ and $E_8$ are each, independently, H, $C_1$-$C_6$ alkyl, substituted $C_1$-$C_6$ alkyl, $C_2$-$C_6$ alkenyl, substituted $C_2$-$C_6$ alkenyl, $C_1$-$C_6$ alkoxy, substituted $C_1$-$C_6$ alkoxy or halogen; and wherein each substituted group comprises one or more optionally protected substituent groups independently selected from $C_1$-$C_6$ alkyl, $C_1$-$C_6$ alkoxy, halogen, hydroxyl, thiol, amino and $C_1$-$C_6$ aminoalkyl.

In certain embodiments, oligomeric compounds comprising at least one bicyclic nucleoside analog of formula II are provided wherein each bicyclic nucleoside analog of formula II has the configuration:

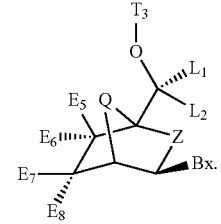

In certain embodiments, oligomeric compounds comprising at least one bicyclic nucleoside analog of formula II are provided wherein each bicyclic nucleoside analog of formula II has the configuration:

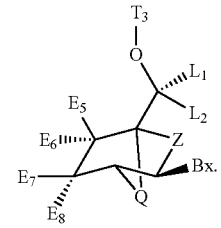

Incorporation of one or more of the bicyclic nucleosides, as provided herein, into an oligomeric compound is expected to enhance one or more desired properties of the resulting oligomeric compound. Such properties include without limitation stability, nuclease resistance, binding affinity, specificity, absorption, cellular distribution, cellular uptake, charge, clearance and pharmacodynamics and pharmacokinetics in general.

In certain embodiments, the bicyclic nucleosides provided herein are incorporated into oligomeric compounds such that a motif results. The placement of bicyclic nucleosides into oligomeric compounds to provide particular motifs can enhance the desired properties of the resulting oligomeric compounds for activity using a particular mechanism such as RNaseH or RNAi. Such motifs include without limitation, gapped motifs, hemimer motifs, blockmer motifs, uniformly fully modified motifs, positionally modified motifs and alternating motifs. In conjunction with these motifs a wide variety of internucleoside linkages can also be used including but not limited to phosphodiester and phosphorothioate internucleoside linkages which can be incorporated uniformly or in various combinations. The oligomeric compounds can further include at least one 5' or 3' terminal group such as for example a conjugate or reporter group. The positioning of the bicyclic nucleosides provided herein, the use of linkage strategies and 5' or 3' terminal groups can be easily optimized to enhance a desired activity for a selected target.

As used herein the term "motif" refers to the pattern created by the relative positioning of monomer subunits within an oligomeric compound wherein the pattern is determined by comparing the sugar groups. The only determinant for the motif of an oligomeric compound is the differences or lack of differences between the sugar groups. The internucleoside linkage, heterocyclic base and further groups such as terminal groups are not considered when determining the motif of an oligomeric compound. As used herein the term "sugar group" as it applies to motifs includes naturally occurring sugars having a furanose ring, sugars having a modified furanose ring and sugar surrogates wherein the furanose ring has been replaced with another ring system such as for example a morpholino or hexitol ring system. When each sugar group is the same (either modified furanose or surrogate ring system) the motif is termed uniformly fully modified. When two or more types of sugar groups are present the motif is defined by the pattern created from the positioning of monomer subunits having one type of sugar group relative to the positioning of monomer subunits having different types of sugar groups within an oligomeric compound.

Illustrative examples of some different types of sugar groups useful in the preparation of oligomeric compounds having motifs include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose), bicyclic modified sugars (such as the 2'-O—CH$_2$-4' or 2'-O—(CH$_2$)$_2$-4' bridged ribose derived bicyclic sugars) and sugar surrogates (such as when the ribose ring has been replaced with a morpholino or a hexitol ring system). The type of heterocyclic base and internucleoside linkage used at each position is variable and is not a factor in determining the motif. The presence of one or more other groups including but not limited to capping groups, conjugate groups and other 5' or 3'-terminal groups is also not a factor in determining the motif.

Representative U.S. patents that teach the preparation of motifs include without limitation, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety. Motifs are also disclosed in International Applications PCT/US2005/019219, filed Jun. 2, 2005 and published as WO 2005/121371 on Dec. 22, 2005 and PCT/US2005/019220, filed Jun. 2, 2005 and published as WO 2005/121372 on Dec. 22, 2005; each of which is incorporated by reference herein in its entirety.

As used herein the term "alternating motif" refers to a an oligomeric compound comprising a contiguous sequence of linked monomer subunits wherein the monomer subunits have two different types of sugar groups that alternate for essentially the entire sequence of the oligomeric compound. Oligomeric compounds having an alternating motif can be described by the formula: 5'-A(-L-B-L-A)$_n$(-L-B)$_{nn}$-3' where A and B are monomer subunits that have different sugar groups, each L is, independently, an internucleoside linking group, n is from about 4 to about 12 and nn is 0 or 1. The heterocyclic base and internucleoside linkage is independently variable at each position. The motif further optionally includes the use of one or more other groups including but not limited to capping groups, conjugate groups and other 5' or 3'-terminal groups. This permits alternating oligomeric compounds from about 9 to about 26 monomer subunits in length. This length range is not meant to be limiting as longer and shorter oligomeric compounds are also amenable to oligomeric compounds provided herein. In certain embodiments, each A or each B comprise bicyclic nucleosides as provided herein.

As used herein the term "uniformly fully modified motif" refers to an oligomeric compound comprising a contiguous sequence of linked monomer subunits that each have the same type of sugar group. The heterocyclic base and internucleoside linkage is independently variable at each position. The motif further optionally includes the use of one or more other groups including but not limited to capping groups, conjugate groups and other 5' or 3'-terminal groups. In certain embodiments, the uniformly fully modified motif includes a contiguous sequence of bicyclic nucleosides. In certain embodiments, one or both of the 5' and 3'-ends of the contiguous sequence of bicyclic nucleosides, comprise 5' or 3'-terminal groups such as one or more unmodified nucleosides.

As used herein the term "hemimer motif" refers to an oligomeric compound comprising a contiguous sequence of monomer subunits that each have the same type of sugar group with a further short contiguous sequence of monomer subunits located at the 5' or the 3' end that have a different type of sugar group. The heterocyclic base and internucleoside linkage is independently variable at each position. The motif further optionally includes the use of one or more other groups including but not limited to capping groups, conjugate groups and other 5' or 3'-terminal groups. In general, a hemimer is an oligomeric compound of uniform sugar groups further comprising a short region (1, 2, 3, 4 or about 5 monomer subunits) having uniform but different sugar groups located on either the 3' or the 5' end of the oligomeric compound.

In certain embodiments, the hemimer motif comprises a contiguous sequence of from about 10 to about 28 monomer subunits having one type of sugar group with from 1 to 5 or from 2 to about 5 monomer subunits having a second type of sugar group located at one of the termini. In certain embodiments, the hemimer is a contiguous sequence of from about 8 to about 20 β-D-2'-deoxyribonucleosides having from 1-12 contiguous bicyclic nucleosides located at one of the termini. In certain embodiments, the hemimer is a contiguous sequence of from about 8 to about 20 β-D-2'-deoxyribonucleosides having from 1-5 contiguous bicyclic nucleosides located at one of the termini. In certain embodiments, the hemimer is a contiguous sequence of from about 12 to about 18 β-D-2'-deoxyribonucleosides having from 1-3 contiguous bicyclic nucleosides located at one of the termini. In certain embodiments, the hemimer is a contiguous sequence of from about 10 to about 14 β-D-2'-deoxyribonucleosides having from 1-3 contiguous bicyclic nucleosides located at one of the termini.

As used herein the terms "blockmer motif" and "blockmer" refer to an oligomeric compound comprising an otherwise contiguous sequence of monomer subunits wherein the sugar groups of each monomer subunit is the same except for an interrupting internal block of contiguous monomer subunits having a different type of sugar group. The heterocyclic base and internucleoside linkage is independently variable at each position of a blockmer. The motif further optionally includes the use of one or more other groups including but not limited to capping groups, conjugate groups and other 5' or 3'-terminal groups. A blockmer overlaps somewhat with a gapmer in the definition but typically only the monomer subunits in the block have non-naturally occurring sugar groups in a blockmer and only the monomer subunits in the external regions have non-naturally occurring sugar groups in a gapmer with the remainder of monomer subunits in the blockmer or gapmer being β-D-2'-deoxyribonucleosides or β-D-ribonucleosides. In certain embodiments, blockmers are provided herein wherein all of the monomer subunits comprise non-naturally occurring sugar groups.

As used herein the term "positionally modified motif" is meant to include an otherwise contiguous sequence of monomer subunits having one type of sugar group that is interrupted with two or more regions of from 1 to about 5 contiguous monomer subunits having another type of sugar group. Each of the two or more regions of from 1 to about 5 contiguous monomer subunits are independently uniformly modified with respect to the type of sugar group. In certain embodiments, each of the two or more regions have the same type of sugar group. In certain embodiments, each of the two or more regions have a different type of sugar group. In certain embodiments, each of the two or more regions, independently, have the same or a different type of sugar group. The heterocyclic base and internucleoside linkage is independently variable at each position of a positionally modified oligomeric compound. The motif further optionally includes the use of one or more other groups including but not limited to capping groups, conjugate groups and other 5' or 3'-terminal groups. In certain embodiments, positionally modified oligomeric compounds are provided comprising a sequence of from 8 to 20 β-D-2'-deoxyribonucleosides that further includes two or three regions of from 2 to about 5 contiguous bicyclic nucleosides each. Positionally modified oligomeric compounds are distinguished from gapped motifs, hemimer motifs, blockmer motifs and alternating motifs because the pattern of regional substitution defined by any positional motif does not fit into the definition provided herein for one of these other motifs. The term positionally modified oligomeric compound includes many different specific substitution patterns.

As used herein the term "gapmer" or "gapped oligomeric compound" refers to an oligomeric compound having two external regions or wings and an internal region or gap. The three regions form a contiguous sequence of monomer subunits with the sugar groups of the external regions being different than the sugar groups of the internal region and wherein the sugar group of each monomer subunit within a particular region is essentially the same. In certain embodiments, each monomer subunit within a particular region has the same sugar group. When the sugar groups of the external regions are the same the gapmer is a symmetric gapmer and when the sugar group used in the 5'-external region is different from the sugar group used in the 3'-external region, the gapmer is an asymmetric gapmer. In certain embodiments, the external regions are small (each independently 1, 2, 3, 4 or about 5 monomer subunits) and the monomer subunits comprise non-naturally occurring sugar groups with the internal region comprising β-D-2'-deoxyribonucleosides. In certain embodiments, the external regions each, independently, comprise from 1 to about 5 monomer subunits having non-naturally occurring sugar groups and the internal region comprises from 6 to 18 unmodified nucleosides. The internal region or the gap generally comprises β-D-2'-deoxyribonucleosides but can comprise non-naturally occurring sugar groups. The heterocyclic base and internucleoside linkage is independently variable at each position of a gapped oligomeric compound. The motif further optionally includes the use of one or more other groups including but not limited to capping groups, conjugate groups and other 5' or 3'-terminal groups.

In certain embodiments, the gapped oligomeric compounds comprise an internal region of β-D-2'-deoxyribonucleosides with one of the external regions comprising bicyclic nucleosides as disclosed herein. In certain embodiments, the gapped oligomeric compounds comprise an internal region of β-D-2'-deoxyribonucleosides with both of the external regions comprising bicyclic nucleosides as provided herein. In certain embodiments, gapped oligomeric compounds are provided herein wherein all of the monomer subunits comprise non-naturally occurring sugar groups.

In certain embodiments, gapped oligomeric compounds are provided comprising one or two bicyclic nucleosides at the 5'-end, two or three bicyclic nucleosides at the 3'-end and an internal region of from 10 to 16 β-D-2'-deoxyribonucleosides. In certain embodiments, gapped oligomeric compounds are provided comprising one bicyclic nucleoside at the 5'-end, two bicyclic nucleosides at the 3'-end and an internal region of from 10 to 16 β-D-2'-deoxyribonucleosides. In certain embodiments, gapped oligomeric compounds are provided comprising one bicyclic nucleosides at the 5'-end, two bicyclic nucleosides at the 3'-end and an internal region of from 10 to 14 β-D-2'-deoxyribonucleosides.

In certain embodiments, gapped oligomeric compounds are provided that are from about 10 to about 21 monomer subunits in length. In certain embodiments, gapped oligomeric compounds are provided that are from about 12 to about 16 monomer subunits in length. In certain embodiments, gapped oligomeric compounds are provided that are from about 12 to about 14 monomer subunits in length.

The terms "substituent" and "substituent group," as used herein, are meant to include groups that are typically added to other groups or parent compounds to enhance desired properties or provide other desired effects. Substituent groups can be protected or unprotected and can be added to one available site or to many available sites in a parent compound. Substituent groups may also be further substituted with other substituent groups and may be attached directly or via a linking group such as an alkyl or hydrocarbyl group to a parent compound.

Substituent groups amenable herein include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$)

or —N($R_{bb}$)C(O)O$R_{aa}$), ureido (—N($R_{bb}$)C(O)—N($R_{bb}$)($R_{cc}$)), thioureido (—N($R_{bb}$)C(S)N($R_{bb}$)($R_{cc}$)), guanidinyl (—N($R_{bb}$)C(=N$R_{bb}$ON($R_{bb}$)($R_{cc}$)), amidinyl (—C(=N$R_{bb}$)N($R_{bb}$)($R_{cc}$) or —N($R_{bb}$)C(=N$R_{bb}$)($R_{aa}$)), thiol (—S$R_{bb}$), sulfinyl (—S(O)$R_{bb}$), sulfonyl (—S(O)$_2R_{bb}$) and sulfonamidyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

In this context, "recursive substituent" means that a substituent may recite another instance of itself. Because of the recursive nature of such substituents, theoretically, a large number may be present in any given claim. One of ordinary skill in the art of medicinal chemistry and organic chemistry understands that the total number of such substituents is reasonably limited by the desired properties of the compound intended. Such properties include, by way of example and not limitation, physical properties such as molecular weight, solubility or log P, application properties such as activity against the intended target and practical properties such as ease of synthesis.

Recursive substituents are an intended aspect of the invention. One of ordinary skill in the art of medicinal and organic chemistry understands the versatility of such substituents. To the degree that recursive substituents are present in a claim of the invention, the total number will be determined as set forth above.

The terms "stable compound" and "stable structure" as used herein are meant to indicate a compound that is sufficiently robust to survive isolation to a useful degree of purity from a reaction mixture, and formulation into an efficacious therapeutic agent. Only stable compounds are contemplated herein.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

The term "heterocyclic radical" as used herein, refers to a radical mono-, or poly-cyclic ring system that includes at least one heteroatom and is unsaturated, partially saturated or fully saturated, thereby including heteroaryl groups. Heterocyclic is also meant to include fused ring systems wherein one or more of the fused rings contain at least one heteroatom and the other rings can contain one or more heteroatoms or optionally contain no heteroatoms. A heterocyclic radical typically includes at least one atom selected from sulfur, nitrogen or oxygen. Examples of heterocyclic radicals include, [1,3]dioxolanyl, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, tetrahydrofuryl and the like. Heterocyclic groups as used herein may optionally include further substituent groups.

The term "hydrocarbyl" includes radical groups that comprise C, O and H. Included are straight, branched and cyclic groups having any degree of saturation. Such hydrocarbyl groups can include one or more heteroatoms selected from N, O and S and can be further mono or poly substituted with one or more substituent groups.

The term "mono or poly cyclic structure" as used herein includes all ring systems selected from single or polycyclic radical ring systems wherein the rings are fused or linked and is meant to be inclusive of single and mixed ring systems individually selected from aliphatic, alicyclic, aryl, heteroaryl, aralkyl, arylalkyl, heterocyclic, heteroaryl, heteroaromatic and heteroarylalkyl. Such mono and poly cyclic structures can contain rings that each have the same level of saturation or each, independently, have varying degrees of saturation including fully saturated, partially saturated or fully unsaturated. Each ring can comprise ring atoms selected from C, N, O and S to give rise to heterocyclic rings as well as rings comprising only C ring atoms which can be present in a mixed motif such as for example benzimidazole wherein one ring has only carbon ring atoms and the fused ring has two nitrogen atoms. The mono or poly cyclic structures can be further substituted with substituent groups such as for example phthalimide which has two =O groups attached to one of the rings. Mono or poly cyclic structures can be attached to parent molecules using various strategies such as directly through a ring atom, through a substituent group or through a bifunctional linking moiety.

The term "oxo" refers to the group (=O).

Linking groups or bifunctional linking moieties such as those known in the art are useful for attachment of chemical functional groups, conjugate groups, reporter groups and other groups to selective sites in a parent compound such as for example an oligomeric compound. In general, a bifunctional linking moiety comprises a hydrocarbyl moiety having two functional groups. One of the functional groups is selected to bind to a parent molecule or compound of interest and the other is selected to bind to essentially any selected group such as a chemical functional group or a conjugate group. In some embodiments, the linker comprises a chain structure or a polymer of repeating units such as ethylene glycols or amino acid units. Examples of functional groups that are routinely used in bifunctional linking moieties include without limitation, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like. Some nonlimiting examples of bifunctional linking moieties include 8-amino-3,6-dioxaoctanoic acid (ADO), succinimidyl 4-(N-maleimidomethyl)cyclohexane-1-carboxylate (SMCC) and 6-aminohexanoic acid (AHEX or AHA). Other linking groups include without limitation, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

In certain embodiments, the oligomeric compounds as provided herein can be modified by covalent attachment of one or more conjugate groups. In general, conjugate groups modify one or more properties of the oligomeric compounds they are attached to. Such oligonucleotide properties include without limitation, pharmacodynamics, pharmacokinetics, binding, absorption, cellular distribution, cellular uptake, charge and clearance. Conjugate groups are routinely used in the chemical arts and are linked directly or via an optional linking moiety or linking group to a parent compound such as an oligomeric compound. A preferred list of conjugate groups includes without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes.

In certain embodiments, the oligomeric compounds as provided herein can be modified by covalent attachment of one or more 5' or 3'-terminal groups. The terms "5' or 3'-terminal groups", "5-terminal group" and "3'-terminal group" as used herein are meant to include useful groups known to the art skilled that can be placed on one or both of the 5' and 3'-ends of an oligomeric compound respectively, for various purposes such as enabling the tracking of the oligomeric compound (a fluorescent label or other reporter group), improving the pharmacokinetics or pharmacodynamics of the oligomeric compound (such as for example: uptake and/or delivery) or enhancing one or more other desirable properties of the oligomeric compound (a group for improving nuclease stability or binding affinity). In certain embodiments, 5' and 3'-terminal groups include without limitation, modified or unmodified nucleosides; two or more linked nucleosides that are independently, modified or unmodified; conjugate groups; capping groups; phosphate moieties; and protecting groups.

The term "phosphate moiety" as used herein, refers to a terminal phosphate group that includes phosphates as well as modified phosphates. The phosphate moiety can be located at either terminus but is preferred at the 5'-terminal nucleoside. In one aspect, the terminal phosphate is unmodified having the formula —O—P(=O)(OH)OH. In another aspect, the terminal phosphate is modified such that one or more of the O and OH groups are replaced with H, O, S, N(R) or alkyl where R is H, an amino protecting group or unsubstituted or substituted alkyl. In certain embodiments, the 5' and or 3' terminal group can comprise from 1 to 3 phosphate moieties that are each, independently, unmodified (di or tri-phosphates) or modified.

As used herein, the term "phosphorus moiety" refers to a group having the formula:

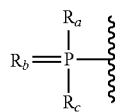

wherein:
$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
$R_b$ is O or S.

Phosphorus moieties included herein can be attached to a monomer, which can be used in the preparation of oligomeric compounds, wherein the monomer may be attached using O, S, $NR_d$ or $CR_eR_f$, wherein $R_d$ includes without limitation H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl or substituted acyl, and $R_e$ and $R_f$ each, independently, include without limitation H, halogen, $C_1$-$C_6$ alkyl, substituted $C_1$-$C_6$ alkyl, $C_1$-$C_6$ alkoxy or substituted $C_1$-$C_6$ alkoxy. Such linked phosphorus moieties include without limitation, phosphates, modified phosphates, thiophosphates, modified thiophosphates, phosphonates, modified phosphonates, phosphoramidates and modified phosphoramidates.

The term "protecting group," as used herein, refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy)methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl)xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenyl)ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. No. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

In certain embodiments, compounds having reactive phosphorus groups are provided that are useful for forming internucleoside linkages including for example phosphodiester and phosphorothioate internucleoside linkages. Such reactive phosphorus groups are known in the art and contain phosphorus atoms in $P^{III}$ or $P^V$ valence state including, but not limited to, phosphoramidite, H-phosphonate, phosphate triesters and phosphorus containing chiral auxiliaries. In certain embodiments, reactive phosphorus groups are selected from diisopropylcyanoethoxy phosphoramidite (—O*—P[N[(CH($CH_3$)$_2$]$_1$]O(CH$_2$)$_2$CN) and H-phosphonate (—O*—P(=O)(H)OH), wherein the O* is provided from the Markush group for the monomer. A preferred synthetic solid phase synthesis utilizes phosphoramidites ($P^{III}$ chemistry) as reactive phosphites. The intermediate phosphite compounds are subsequently oxidized to the phosphate or thiophosphate ($P^V$ chemistry) using known methods to yield, phosphodiester or phosphorothioate internucleoside linkages. Additional reactive phosphates and phosphites are disclosed in Tetrahedron Report Number 309 (Beaucage and Iyer, *Tetrahedron,* 1992, 48, 2223-2311).

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216, 141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein the phrase "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

The bicyclic nucleosides provided herein can be prepared by any of the applicable techniques of organic synthesis, as, for example, illustrated in the examples below. Many such techniques are well known in the art. However, many of the known techniques are elaborated in *Compendium of Organic Synthetic Methods*, John Wiley & Sons, New York: Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade Jr., 1980; Vol. 5, Leroy G. Wade Jr., 1984; and Vol. 6, Michael B. Smith; as well as March, J., *Advanced Organic Chemistry,* 3rd Edition, John Wiley & Sons, New York, 1985; *Comprehensive Organic Synthesis. Selectivity, Strategy & Efficiency in Modern Organic Chemistry,* in 9 Volumes, Barry M. Trost, Editor-in-Chief, Pergamon Press, New York, 1993; *Advanced Organic Chemistry, Part B: Reactions and Synthesis,* 4th Edition; Carey and Sundberg, Kluwer Academic/Plenum Publishers, New York, 2001; *Advanced Organic Chemistry, Reactions, Mechanisms, and Structure,* 2nd Edition, March, McGraw Hill, 1977; Greene, T. W., and Wutz, P. G. M., *Protecting Groups in Organic Synthesis,* 4th Edition, John Wiley & Sons, New York, 1991; and Larock, R. C., *Comprehensive Organic Transformations,* 2nd Edition, John Wiley & Sons, New York, 1999.

The compounds described herein contain one or more asymmetric centers and thus give rise to enantiomers, diastereomers, and other stereoisomeric forms that may be defined, in terms of absolute stereochemistry, as (R)- or (S)-, α or β, or as (D)- or (L)-such as for amino acids. Included herein are all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions*, John Wiley & Sons, 1981. When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to limit a particular configuration unless the text so states.

As is known in the art, a nucleoside is a base-sugar combination. The base portion of the nucleoside is normally a heterocyclic base moiety. The two most common classes of such heterocyclic bases are purines and pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. The respective ends of this linear polymeric structure can be joined to form a circular structure by hybridization or by formation of a covalent bond. However, open linear structures are generally desired. Within the oligonucleotide structure, the phosphate groups are commonly referred to as forming the internucleoside linkages of the oligonucleotide. The normal internucleoside linkage of RNA and DNA is a 3' to 5' phosphodiester linkage.

The term "nucleotide mimetic" as used herein is meant to include monomers that incorporate into oligomeric compounds with sugar and linkage surrogate groups, such as for example peptide nucleic acids (PNA) or morpholinos (linked by —N(H)—C(=O)—O—). In general, the heterocyclic base at each position is maintained for hybridization to a nucleic acid target but the sugar and linkage is replaced with surrogate groups that are expected to function similar to native groups but have one or more enhanced properties.

As used herein the term "nucleoside mimetic" is intended to include those structures used to replace the sugar and the base at one or more positions of an oligomeric compound. Examples of nucleoside mimetics include without limitation replacement of the heterocyclic base moiety with a mimetic thereof such as a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar group with a group such as for example a morpholino, a cyclohexenyl or a bicyclo[3.1.0]hexyl.

As used herein the term "modified nucleoside" is meant to include all manner of modified nucleosides that can be incorporated into an oligomeric compound using oligomer synthesis. The term is intended to include modifications made to a nucleoside such as modified stereochemical configurations, one or more substitutions, and deletion of groups as opposed to the use of surrogate groups which are described elsewhere herein. The term includes nucleosides having a furanose sugar (or 4'-S analog) portion and can include a heterocyclic base or can include an abasic site. One group of representative modified nucleosides includes without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as for example, bicyclic nucleosides wherein the sugar group has a 2'-O—CHR$_a$-4' bridging group, wherein R$_a$ is H, alkyl or substituted alkyl) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as a base and sugar modified nucleosides. These modifications are meant to be illustrative and not exhaustive as other modifications are known in the art and are also envisioned as possible modifications for the modified nucleosides described herein.

As used herein the term "monomer subunit" is meant to include all manner of monomer units that are amenable to oligomer synthesis with one preferred list including monomer subunits such as β-D-ribonucleosides, β-D-2'-deoxyribnucleosides, modified nucleosides, including substituted nucleosides (such as 2', 5' and bis substituted nucleosides), 4'-S-modified nucleosides, (such as 4'-S-ribonucleosides, 4'-S-2'-deoxyribonucleosides and 4'-S-2'-substituted ribonucleosides), bicyclic modified nucleosides (such as bicyclic nucleosides wherein the sugar group has a 2'-O—CHR$_a$-4' bridging group, wherein R$_a$ is H, alkyl or substituted alkyl), other modified nucleosides, nucleoside mimetics, nucleosides having sugar surrogates and the bicyclic nucleosides as provided herein.

The term "oligonucleotide" refers to an oligomer or polymer of ribonucleic acid (RNA) or deoxyribonucleic acid (DNA). This term includes oligonucleotides composed of naturally-occurring nucleobases, sugars and covalent internucleoside linkages. The term "oligonucleotide analog" refers to oligonucleotides that have one or more non-naturally occurring portions. Such non-naturally occurring oligonucleotides are often desired over naturally occurring forms because of desirable properties such as, for example, enhanced cellular uptake, enhanced affinity for nucleic acid target and/or increased stability in the presence of nucleases.

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkeneyl, sulfamate, methyleneimino, methylenehydrazino, sulfonate, sulfonamide, amide and others having mixed N, O, S and CH$_2$ component parts.

The terms "heterocyclic base moiety" and "nucleobase" as used herein, include unmodified or naturally occurring nucleobases, modified or non-naturally occurring nucleobases as well as synthetic mimetics thereof (such as for example phenoxazines). In general, a heterocyclic base moiety is heterocyclic system that contains one or more atoms or groups of atoms capable of hydrogen bonding to a base of a nucleic acid.

As used herein the terms, "unmodified nucleobase" and "naturally occurring nucleobase" include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine ([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering*, Kroschwitz, J. I., Ed., John Wiley & Sons, 1990, 858-859; those disclosed by Englisch et al., *Angewandte Chemie*, International Edition, 1991, 30, 613; and those disclosed by Sanghvi, Y. S., Chapter 15, *Antisense Research and Applications*, Crooke, S. T. and Lebleu, B., Eds., CRC Press, 1993, 273-288.

The heterocyclic base moiety of each of the bicyclic nucleosides can be modified with one or more substituent groups to enhance one or more properties such as affinity for a target strand or affect some other property in an advantageous manner. Modified nucleobases include without limitation, universal bases, hydrophobic bases, promiscuous bases, size-expanded bases, and fluorinated bases as defined herein. Certain of these nucleobases are particularly useful for increasing the binding affinity of the oligomeric compounds as provided herein. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (*Antisense Research and Applications*, Sanghvi, Y. S., Crooke, S. T. and Lebleu, B., Eds., CRC Press, Boca Raton, 1993, 276-278).

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

In general, the term "oligomeric compound" refers to a contiguous sequence of linked monomer subunits. In general, each linked monomer subunit is directly or indirectly attached to a heterocyclic base moiety but abasic sites are also possible. At least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having a plurality of non-naturally occurring nucleoside mimetics and or nucleosides having sugar surrogate groups. In certain embodiments, oligomeric compounds comprise a plurality of monomer subunits independently selected from naturally occurring nucleosides, non-naturally occurring nucleosides, modified nucleosides, nucleoside mimetics, and nucleosides having sugar surrogate groups.

When preparing oligomeric compounds having specific motifs as disclosed herein it can be advantageous to mix non-naturally occurring monomer subunits such as the bicyclic nucleosides as provided herein with other non-naturally occurring monomer subunits, naturally occurring monomer subunits (nucleosides) or mixtures thereof. In certain embodiments, oligomeric compounds are provided herein comprising a contiguous sequence of linked monomer subunits wherein at least one monomer subunit is a bicyclic nucleoside as provided herein. In certain embodiments, oligomeric compounds are provided comprising a plurality of bicyclic nucleosides as provided herein.

Oligomeric compounds are routinely prepared linearly but can also be joined or otherwise prepared to be circular and/or can be prepared to include branching. Oligomeric compounds can form double stranded constructs such as for example two strands hybridized to form a double stranded composition. Double stranded compositions can be linked or separate and can include various other groups such as conjugates and/or overhangs on the ends.

Oligomeric compounds provided herein can optionally contain one or more nucleosides wherein the sugar group has been modified. Such sugar modified nucleosides may impart enhanced nuclease stability, increased binding affinity or some other beneficial biological property to the oligomeric compounds. As used herein the term "modified sugar" refers to modifications that can be made to the furanose sugar portion of otherwise unmodified or modified nucleosides useful herein. Such modified sugars include without limitation substitution with one or more substituent groups, bridging of two non-geminal ring carbon atoms to form a bicyclic nucleoside or substitution of the 4'-O atom with a disubstituted methylene group [$C(R)_2$] or a heteroatom or substituted heteroatom (NR). Modified sugar moieties can also comprise mixtures of these modifications such as for example putting a 5'-substituent group on a bicyclic nucleoside.

Examples of substituent groups useful for modifying sugar moieties of nucleosides include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-O—CH$_3$, OCF$_3$, 2'-O—CH$_2$CH$_3$, 2'-O—(CH$_2$)$_2$CH$_3$, 2'-O—(CH$_2$)$_2$—O—CH$_3$, 2'-O(CH$_2$)$_2$SCH$_3$, 2'-O—CH$_2$—CH=CH$_2$ (MOE), 2'-O—(CH$_2$)$_3$—N(R$_m$)(R$_n$), 2'-O—(CH$_2$)$_2$—O—N(R$_m$)(R$_n$), 2'-O—(CH$_2$)$_2$—O—(CH$_2$)$_2$—N(R$_m$)(R$_n$), 2'-O—CH$_2$C(=O)—N(R$_m$)(R$_n$), 2'-O—CH$_2$C(=O)—N(H)—(CH$_2$)$_2$—N(R$_m$)(R$_n$) and 2'-O—CH$_2$—N(H)—C(=NR$_m$)[N(R$_m$)(R$_n$)], 5'-vinyl, 5'-methyl (R or S) and 4'-S wherein each R$_m$ and R$_n$ is, independently, H, substituted or unsubstituted C$_1$-C$_{10}$ alkyl or a protecting group. Further examples of modified sugar moieties include without limitation bicyclic sugars (e.g. bicyclic nucleic acids or bicyclic nucleosides discussed below).

Combinations of these modifications are also provided for herein without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-CH$_2$—O-2' bicyclic nucleoside is further substituted at the 5' position with a 5'-methyl or a 5'-vinyl group).

As used herein the terms "bicyclic nucleic acid" and "bicyclic nucleoside" refer to nucleosides wherein the sugar portion of the nucleoside is bicyclic (e.g. bicyclic sugar). In certain embodiments, a bicyclic nucleic acid comprises a nucleoside wherein the furanose ring comprises a bridge between two non-geminal ring carbon atoms. Examples of bicyclic nucleosides include without limitation nucleosides comprising a bridge between the 4' and the 2' ribosyl ring atoms. In certain embodiments, oligomeric compounds provided herein include one or more bicyclic nucleosides wherein the bridge comprises one of the formulae: 4'-(CH$_2$)—O-2' (LNA); 4'-(CH$_2$)—S-2; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., *J. Org. Chem.,* 2009, 74, 118-134); and 4'-CH$_2$—C(=CH$_2$)-2' (and analogs thereof see published International Application WO 2008/154401, published on Dec. 8, 2008). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated as is the case with the non-ring system used in peptide nucleic acid. The term is meant to include replacement of the sugar group with all manner of sugar surrogates know in the art and includes without limitation sugar surrogate groups such as morpholinos, cyclohexenyls and cyclohexitols. In most monomer subunits having a sugar surrogate group the heterocyclic base moiety is generally maintained to permit hybridization.

In certain embodiments, nucleosides having sugar surrogate groups include without limitation, replacement of the ribosyl ring with a surrogate ring system such as a tetrahydropyranyl ring system (also referred to as hexitol) as illustrated below:

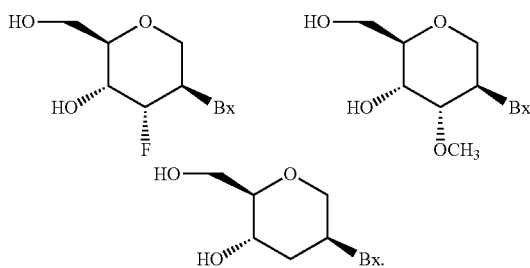

Many other monocyclic, bicyclic and tricyclic ring systems are known in the art and are suitable as sugar surrogates that can be used to modify nucleosides for incorporation into oligomeric compounds as provided herein (see for example review article: Leumann, Christian J.). Such ring systems can undergo various additional substitutions to further enhance their activity.

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

Those skilled in the art, having possession of the present disclosure will be able to prepare oligomeric compounds, comprising a contiguous sequence of linked monomer subunits, of essentially any viable length to practice the methods disclosed herein. Such oligomeric compounds will include at least one and preferably a plurality of the bicyclic nucleosides provided herein and may also include other monomer subunits including but not limited to nucleosides, modified nucleosides, nucleosides comprising sugar surrogate groups and nucleoside mimetics.

In certain embodiments, oligomeric compounds provided herein comprise from about 8 to about 80 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 monomer subunits in length, or any range therewithin.

In certain embodiments, oligomeric compounds provided herein comprise from about 8 to 40 monomer subunits in length. One having ordinary skill in the art will appreciate that this embodies oligomeric compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 monomer subunits in length, or any range therewithin.

In certain embodiments, oligomeric compounds provided herein comprise from about 8 to 20 monomer subunits in length. One having ordinary skill in the art will appreciate that this embodies oligomeric compounds of 8, 9, 10, 11, 12, 13, 14, 15, 16, 17, 18, 19 or 20 monomer subunits in length, or any range therewithin.

In certain embodiments, oligomeric compounds provided herein comprise from about 8 to 16 monomer subunits in length. One having ordinary skill in the art will appreciate that this embodies oligomeric compounds of 8, 9, 10, 11, 12, 13, 14, 15 or 16 monomer subunits in length, or any range therewithin.

In certain embodiments, oligomeric compounds provided herein comprise from about 10 to 14 monomer subunits in length. One having ordinary skill in the art will appreciate that this embodies oligomeric compounds of 10, 11, 12, 13 or 14 monomer subunits in length, or any range therewithin.

In certain embodiments, oligomeric compounds provided herein comprise from about 10 to 18 monomer subunits in length. One having ordinary skill in the art will appreciate that this embodies oligomeric compounds of 10, 11, 12, 13, 14, 15, 16, 17 or 18 monomer subunits in length, or any range therewithin.

In certain embodiments, oligomeric compounds provided herein comprise from about 10 to 21 monomer subunits in length. One having ordinary skill in the art will appreciate that this embodies oligomeric compounds of 10, 11, 12, 13, 14, 15, 16, 17, 18, 19, 20 or 21 monomer subunits in length, or any range therewithin.

In certain embodiments, oligomeric compounds provided herein comprise from about 12 to 14 monomer subunits in length. One having ordinary skill in the art will appreciate that this embodies oligomeric compounds of 12, 13 or 14 monomer subunits in length, or any range therewithin.

In certain embodiments, oligomeric compounds provided herein comprise from about 12 to 18 monomer subunits in length. One having ordinary skill in the art will appreciate that this embodies oligomeric compounds of 12, 13, 14, 15, 16, 17 or 18 monomer subunits in length, or any range therewithin.

In certain embodiments, oligomeric compounds provided herein comprise from about 12 to 21 monomer subunits in length. One having ordinary skill in the art will appreciate that this embodies oligomeric compounds of 12, 13, 14, 15, 16, 17, 18, 19, 20 or 21 monomer subunits in length, or any range therewithin.

In certain embodiments, oligomeric compounds provided herein comprise from about 14 to 18 monomer subunits in length. One having ordinary skill in the art will appreciate that this embodies oligomeric compounds of 14, 15, 16, 17 or 18 monomer subunits in length, or any range therewithin.

In certain embodiments, oligomeric compounds of any of a variety of ranges of lengths of linked monomer subunits are provided. In certain embodiments, oligomeric compounds are provided consisting of X—Y linked monomer subunits, where X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X<Y. For example, in certain embodiments, this provides oligomeric compounds comprising: 8-9, 8-10, 8-11, 8-12, 8-13, 8-14, 8-15, 8-16, 8-17, 8-18, 8-19, 8-20, 8-21, 8-22, 8-23, 8-24, 8-25, 8-26, 8-27, 8-28, 8-29, 8-30, 9-10, 9-11, 9-12, 9-13, 9-14, 9-15, 9-16, 9-17, 9-18, 9-19, 9-20, 9-21, 9-22, 9-23, 9-24, 9-25, 9-26, 9-27, 9-28, 9-29, 9-30, 10-11, 10-12, 10-13, 10-14, 10-15, 10-16, 10-17, 10-18, 10-19, 10-20, 10-21, 10-22, 10-23, 10-24, 10-25, 10-26, 10-27, 10-28, 10-29, 10-30, 11-12, 11-13, 11-14, 11-15, 11-16, 11-17, 11-18, 11-19, 11-20, 11-21, 11-22, 11-23, 11-24, 11-25, 11-26, 11-27, 11-28, 11-29, 11-30, 12-13, 12-14, 12-15, 12-16, 12-17, 12-18, 12-19, 12-20, 12-21, 12-22, 12-23, 12-24, 12-25, 12-26, 12-27, 12-28, 12-29, 12-30, 13-14, 13-15, 13-16, 13-17, 13-18, 13-19, 13-20, 13-21, 13-22, 13-23, 13-24, 13-25, 13-26, 13-27, 13-28, 13-29, 13-30, 14-15, 14-16, 14-17, 14-18, 14-19, 14-20, 14-21, 14-22, 14-23, 14-24, 14-25, 14-26, 14-27, 14-28, 14-29, 14-30, 15-16, 15-17, 15-18, 15-19, 15-20, 15-21, 15-22, 15-23, 15-24, 15-25, 15-26, 15-27, 15-28, 15-29, 15-30, 16-17, 16-18, 16-19, 16-20, 16-21, 16-22, 16-23, 16-24, 16-25, 16-26, 16-27, 16-28, 16-29, 16-30, 17-18, 17-19, 17-20, 17-21, 17-22, 17-23, 17-24, 17-25, 17-26, 17-27, 17-28, 17-29, 17-30, 18-19, 18-20, 18-21, 18-22, 18-23, 18-24, 18-25, 18-26, 18-27, 18-28, 18-29, 18-30, 19-20, 19-21, 19-22, 19-23, 19-24, 19-25, 19-26, 19-27, 19-28, 19-29, 19-30, 20-21, 20-22, 20-23, 20-24, 20-25, 20-26, 20-27, 20-28, 20-29, 20-30, 21-22, 21-23, 21-24, 21-25, 21-26, 21-27, 21-28, 21-29, 21-30, 22-23, 22-24, 22-25, 22-26, 22-27, 22-28, 22-29, 22-30, 23-24, 23-25, 23-26, 23-27, 23-28, 23-29, 23-30, 24-25, 24-26, 24-27, 24-28, 24-29, 24-30, 25-26, 25-27, 25-28, 25-29, 25-30, 26-27, 26-28, 26-29, 26-30, 27-28, 27-29, 27-30, 28-29, 28-30, or 29-30 linked monomer subunits.

In certain embodiments, the ranges for the oligomeric compounds listed herein are meant to limit the number of monomer subunits in the oligomeric compounds, however such oligomeric compounds may further include 5' and/or 3'-terminal groups including but not limited to protecting groups such as hydroxyl protecting groups, optionally linked conjugate groups and/or other substituent groups.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods,* 2001, 23, 206-217; Gait et al., *Applications of Chemically synthesized RNA in RNA:Protein Interactions*, Smith, Ed., 1998, 1-36; Gallo et al., *Tetrahedron,* 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. No. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-[1(2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

As used herein the term "hybridization" includes the pairing of complementary strands of oligomeric compounds such as including the binding of an oligomeric compound as provided herein to a target nucleic acid. In certain embodiments, the mechanism of pairing involves hydrogen bonding, which may be Watson-Crick, Hoogsteen or reversed Hoogsteen hydrogen bonding, between complementary heterocyclic base moieties of nucleosides (or monomer subunits) that are in close enough proximity to hydrogen bond. For example, adenine and thymine are complementary nucleobases which pair through the formation of hydrogen bonds. Hybridization can occur under varying circumstances.

An oligomeric compound is specifically hybridizable when binding of the compound to the target nucleic acid interferes with the normal function of the target nucleic acid resulting in a loss of activity. To be specifically hybridizable also requires a sufficient degree of complementarity to avoid non-specific binding of the oligomeric compound to non-target nucleic acid sequences under the conditions in which specific binding is desired, i.e., under physiological conditions (for in vivo assays or therapeutic treatment) or other diagnostic conditions (for performing in vitro assays).

As used herein the term "complementary," refers to the capacity for precise pairing of two nucleobases regardless of where the two nucleobases are located. For example, if a nucleobase at a certain position of an oligomeric compound is capable of hydrogen bonding with a nucleobase at a certain position of a target nucleic acid, the target nucleic acid being a DNA, RNA, or oligonucleotide molecule, then the position of hydrogen bonding between the oligonucleotide and the target nucleic acid is considered to be a complementary position. The oligomeric compound and the further DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between an oligomeric compound and its target nucleic acid.

It is understood in the art that the sequence of an oligomeric compound need not be 100% complementary to that of its target nucleic acid to be specifically hybridizable. Moreover, an oligomeric compound may hybridize over one or more segments such that intervening or adjacent segments are not involved in the hybridization event (e.g., a loop structure or hairpin structure). In certain embodiments, oligomeric compounds can comprise at least about 70%, at least about 80%, at least about 90%, at least about 95%, or at least about 99% sequence complementarity to a target region within the target nucleic acid sequence to which they are targeted. For example, an oligomeric compound in which 18 of 20 nucleobases of the oligomeric compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an oligomeric compound which is 18 nucleobases in length having 4 (four) noncomplementary nucleobases which are flanked by two regions of complete complementarity with the target nucleic acid would have 77.8% overall complementarity with the target nucleic acid and would thus fall within this scope. Percent complementarity of an oligomeric compound with a region of a target nucleic acid can be determined routinely using BLAST programs (basic local alignment search tools) and PowerBLAST programs known in the art (Altschul et al., *J. Mol. Biol.,* 1990, 215, 403-410; Zhang and Madden, Genome Res., 1997, 7, 649-656).

Further included herein are oligomeric compounds such as antisense oligomeric compounds, antisense oligonucleotides, ribozymes, external guide sequence (EGS) oligonucleotides, alternate splicers, primers, probes, and other oligomeric compounds which hybridize to at least a portion of the target nucleic acid. As such, these oligomeric compounds may be introduced in the form of single-stranded, double-stranded, circular or hairpin oligomeric compounds and may contain structural elements such as internal or terminal bulges or loops. Once introduced to a system, the oligomeric compounds provided herein may elicit the action of one or more enzymes or structural proteins to effect modification of the target nucleic acid. Alternatively, the oligomeric compound may inhibit the activity the target nucleic acid through an occupancy-based method, thus interfering with the activity of the target nucleic acid.

One non-limiting example of such an enzyme is RNAse H, a cellular endonuclease which cleaves the RNA strand of an RNA:DNA duplex. It is known in the art that single-stranded oligomeric compounds which are "DNA-like" elicit RNAse H. Activation of RNase H, therefore, results in cleavage of the RNA target, thereby greatly enhancing the efficiency of oligonucleotide-mediated inhibition of gene expression. Similar roles have been postulated for other ribonucleases such as those in the RNase III and ribonuclease L family of enzymes.

While one form of oligomeric compound is a single-stranded antisense oligonucleotide, in many species the introduction of double-stranded structures, such as double-stranded RNA (d5RNA) molecules, has been shown to induce potent and specific antisense-mediated reduction of the function of a gene or its associated gene products. This phenomenon occurs in both plants and animals and is believed to have an evolutionary connection to viral defense and transposon silencing.

In some embodiments, "suitable target segments" may be employed in a screen for additional oligomeric compounds that modulate the expression of a selected protein. "Modulators" are those oligomeric compounds that decrease or increase the expression of a nucleic acid molecule encoding a protein and which comprise at least an 8-nucleobase portion which is complementary to a suitable target segment. The screening method comprises the steps of contacting a suitable target segment of a nucleic acid molecule encoding a protein with one or more candidate modulators, and selecting for one or more candidate modulators which decrease or increase the expression of a nucleic acid molecule encoding a protein. Once it is shown that the candidate modulator or modulators are capable of modulating (e.g. either decreasing or increasing) the expression of a nucleic acid molecule encoding a peptide, the modulator may then be employed herein in further investigative studies of the function of the peptide, or for use as a research, diagnostic, or therapeutic agent. In the case of oligomeric compounds targeted to microRNA, candidate modulators may be evaluated by the extent to which they increase the expression of a microRNA target RNA or protein (as interference with the activity of a microRNA will result in the increased expression of one or more targets of the microRNA).

Suitable target segments may also be combined with their respective complementary oligomeric compounds provided herein to form stabilized double-stranded (duplexed) oligonucleotides. Such double stranded oligonucleotide moieties have been shown in the art to modulate target expression and regulate translation as well as RNA processing via an antisense mechanism. Moreover, the double-stranded moieties may be subject to chemical modifications (Fire et al., *Nature,* 1998, 391, 806-811; Timmons and Fire, *Nature,* 1998, 395, 854; Timmons et al., *Gene,* 2001, 263, 103-112; Tabara et al., *Science,* 1998, 282, 430-431; Montgomery et al., *Proc. Natl. Acad. Sci. USA,* 1998, 95, 15502-15507; Tuschl et al., *Genes Dev.,* 1999, 13, 3191-3197; Elbashir et al., *Nature,* 2001, 411, 494-498; Elbashir et al., *Genes Dev.,* 2001, 15, 188-200). For example, such double-stranded moieties have been shown to inhibit the target by the classical hybridization of antisense strand of the duplex to the target, thereby triggering enzymatic degradation of the target (Tijsterman et al., *Science,* 2002, 295, 694-697).

The oligomeric compounds provided herein can also be applied in the areas of drug discovery and target validation. In certain embodiments, provided herein is the use of the oligomeric compounds and targets identified herein in drug discovery efforts to elucidate relationships that exist between proteins and a disease state, phenotype, or condition. These methods include detecting or modulating a target peptide comprising contacting a sample, tissue, cell, or organism with one or more oligomeric compounds provided herein, measuring the nucleic acid or protein level of the target and/or a related phenotypic or chemical endpoint at some time after treatment, and optionally comparing the measured value to a non-treated sample or sample treated with a further oligomeric compound as provided herein. These methods can also be performed in parallel or in combination with other experiments to determine the function of unknown genes for the process of target validation or to determine the validity of a particular gene product as a target for treatment or prevention of a particular disease, condition, or phenotype. In certain embodiments, oligomeric compounds are provided for use in therapy. In certain embodiments, the therapy is reducing target messenger RNA.

As used herein, the term "dose" refers to a specified quantity of a pharmaceutical agent provided in a single administration. In certain embodiments, a dose may be administered in two or more boluses, tablets, or injections. For example, in certain embodiments, where subcutaneous administration is desired, the desired dose requires a volume not easily accommodated by a single injection. In such embodiments, two or more injections may be used to achieve the desired dose. In certain embodiments, a dose may be administered in two or more injections to minimize injection site reaction in an individual.

In certain embodiments, chemically-modified oligomeric compounds are provided herein that may have a higher affinity for target RNAs than does non-modified DNA. In certain such embodiments, higher affinity in turn provides increased potency allowing for the administration of lower doses of such compounds, reduced potential for toxicity, improvement in therapeutic index and decreased overall cost of therapy.

Effect of nucleoside modifications on RNAi activity is evaluated according to existing literature (Elbashir et al., *Nature*, 2001, 411, 494-498; Nishikura et al., *Cell*, 2001, 107, 415-416; and Bass et al., *Cell*, 2000, 101, 235-238.)

In certain embodiments, oligomeric compounds provided herein can be utilized for diagnostics, therapeutics, prophylaxis and as research reagents and kits. Furthermore, antisense oligonucleotides, which are able to inhibit gene expression with exquisite specificity, are often used by those of ordinary skill to elucidate the function of particular genes or to distinguish between functions of various members of a biological pathway. In certain embodiments, oligomeric compounds provided herein can be utilized either alone or in combination with other oligomeric compounds or other therapeutics as tools in differential and/or combinatorial analyses to elucidate expression patterns of a portion or the entire complement of genes expressed within cells and tissues. Oligomeric compounds can also be effectively used as primers and probes under conditions favoring gene amplification or detection, respectively. These primers and probes are useful in methods requiring the specific detection of nucleic acid molecules encoding proteins and in the amplification of the nucleic acid molecules for detection or for use in further studies. Hybridization of oligomeric compounds as provided herein, particularly the primers and probes, with a nucleic acid can be detected by means known in the art. Such means may include conjugation of an enzyme to the oligonucleotide, radiolabelling of the oligonucleotide or any other suitable detection means. Kits using such detection means for detecting the level of selected proteins in a sample may also be prepared.

As one nonlimiting example, expression patterns within cells or tissues treated with one or more of the oligomeric compounds provided herein are compared to control cells or tissues not treated with oligomeric compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds and or oligomeric compounds which affect expression patterns.

Examples of methods of gene expression analysis known in the art include DNA arrays or microarrays (Brazma and Vilo, *FEBS Lett.*, 2000, 480, 17-24; Celis, et al., *FEBS Lett.*, 2000, 480, 2-16), SAGE (serial analysis of gene expression) (Madden, et al., *Drug Discov. Today*, 2000, 5, 415-425), READS (restriction enzyme amplification of digested cDNAs) (Prashar and Weissman, *Methods Enzymol.*, 1999, 303, 258-72), TOGA (total gene expression analysis) (Sutcliffe, et al., *Proc. Natl. Acad. Sci. USA*, 2000, 97, 1976-81), protein arrays and proteomics (Celis, et al., *FEBS Lett.*, 2000, 480, 2-16; Jungblut, et al., *Electrophoresis*, 1999, 20, 2100-10), expressed sequence tag (EST) sequencing (Celis, et al., *FEBS Lett.*, 2000, 480, 2-16; Larsson, et al., *J. Biotechnol.*, 2000, 80, 143-57), subtractive RNA fingerprinting (SuRF) (Fuchs, et al., *Anal. Biochem.*, 2000, 286, 91-98; Larson, et al., *Cytometry*, 2000, 41, 203-208), subtractive cloning, differential display (DD) (Jurecic and Belmont, *Curr. Opin. Microbiol.*, 2000, 3, 316-21), comparative genomic hybridization (Carulli, et al., *J. Cell Biochem. Suppl.*, 1998, 31, 286-96), FISH (fluorescent in situ hybridization) techniques (Going and Gusterson, *Eur. J. Cancer*, 1999, 35, 1895-904) and mass spectrometry methods (To, *Comb. Chem. High Throughput Screen*, 2000, 3, 235-41).

While in certain embodiments, oligomeric compounds provided herein can be utilized as described, the following examples serve only to illustrate and are not intended to be limiting.

EXAMPLES

General $^1$H and $^{13}$C NMR spectra were recorded on a 300 MHz and 75 MHz Bruker spectrometer, respectively. Silica gel 60 from EM Science was used for purification.

Example 1

Preparation of (1R,3R,4R,7S)-7-(2-cyanoethoxy (diisopropylamino)phosphin oxy)-1-(4,4'-dimethoxytrityloxymethyl)-3-(N-Bz-(Cytidin-1-yl)-2,5-dioxabicyclo[2.2.2]octane (14 U, 16 C)

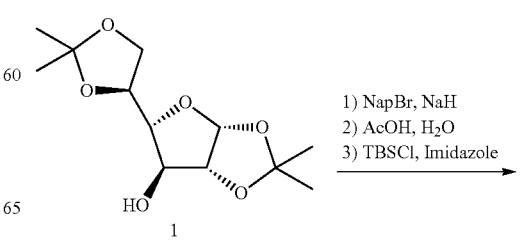

-continued

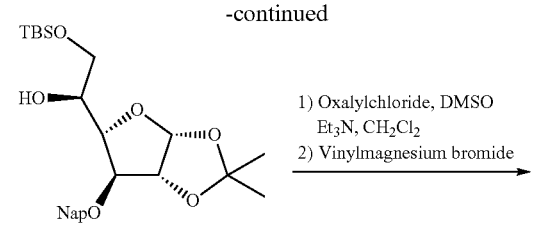

1) Oxalylchloride, DMSO Et₃N, CH₂Cl₂
2) Vinylmagnesium bromide

2

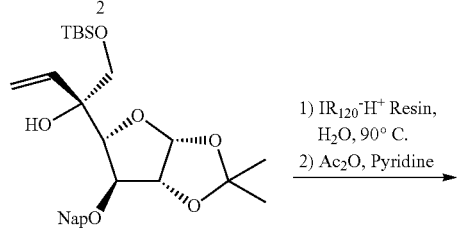

1) IR₁₂₀⁻H⁺ Resin, H₂O, 90° C.
2) Ac₂O, Pyridine

3

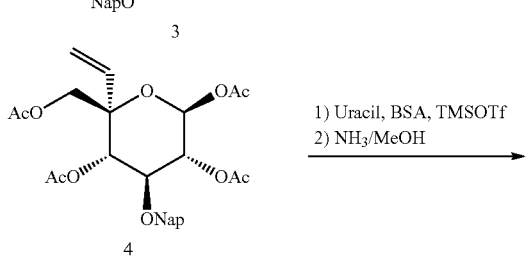

1) Uracil, BSA, TMSOTf
2) NH₃/MeOH

4

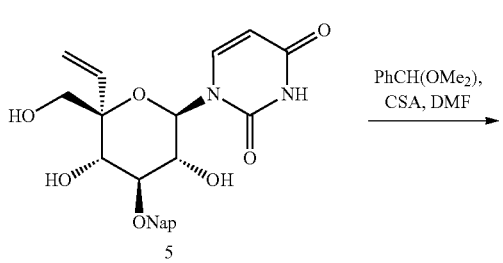

PhCH(OMe₂), CSA, DMF

5

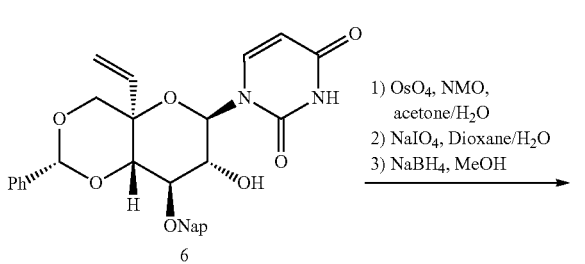

1) OsO₄, NMO, acetone/H₂O
2) NaIO₄, Dioxane/H₂O
3) NaBH₄, MeOH

6

-continued

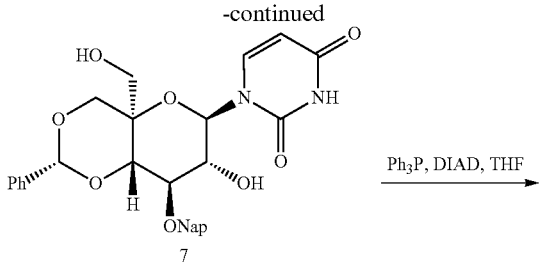

Ph₃P, DIAD, THF

7

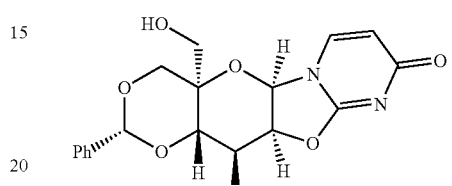

NaH, DMF. rt, 2 hours

8

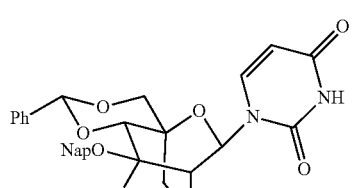  

+ (9:1)

9

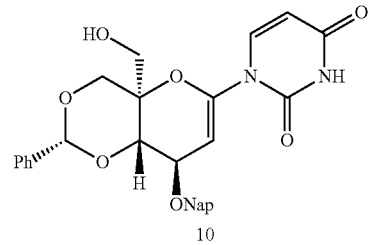

10

Note: Compound 4 was prepared from compound 1 by a slightly modified version of the procedures found in *Tetrahedron Lett.*, 1993, 1653 and *Tetrahedron*, 2004, 6813.

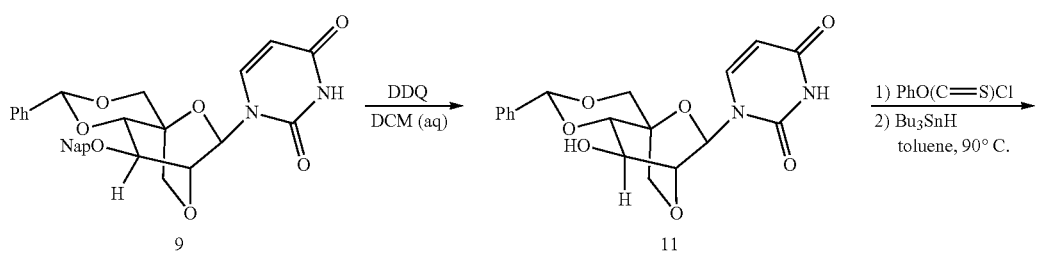

9  →(DDQ / DCM (aq))→  11  →(1) PhO(C=S)Cl  2) Bu₃SnH toluene, 90° C.)→

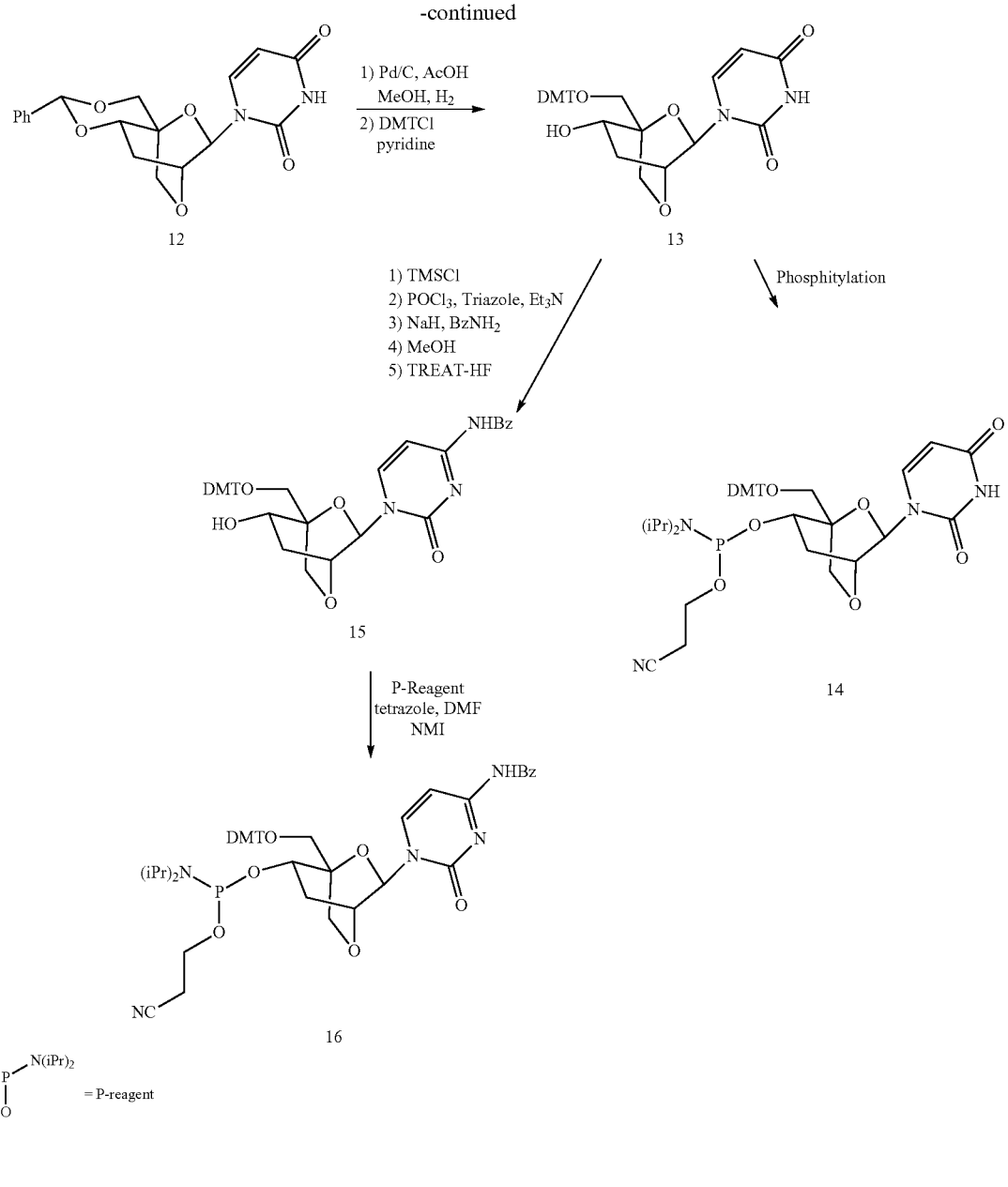

Compound 1

The starting material, Compound 1, is prepared according to the procedure of Moffatt et al, *J. Org. Chem.*, 1979, 44, 1301. Compound 1 is also commercially available from a number of vendors.

Compound 2

Alkylation of Diacetone Glucose

NaH (60% in Mineral oil, 49.2 g, 1.6 equivalents) was added to a 2 L round bottom flask flushed with nitrogen, and the NaH was washed with hexanes (2×1.0 L) to remove the mineral oil. After decanting the hexanes, DMF (700 mL) was added and the mixture was cooled in an ice bath. Diacetone glucose (1, 200 g, 0.77 moles) was then added over a period of 30 minutes. The ice-bath was removed and the mixture was stirred for 1 hour at room temperature. The reaction was then cooled in an ice-bath for second time, and 1-bromomethyl-napthylene (187 g, 1.1 equiv) in DMF (100 mL) was added drop-wise over a 30-minute period. Upon complete addition, the ice-bath was stirred over night while the ice was allowed to melt, thereby allowing the reaction to proceed to room temperature. After 16 hours, the reaction was complete, as determined by tlc (Rf=0.45, 20% EtOAc/hexanes and visualized by charring after treatment with anisaldehyde spray reagent). The mixture was then poured onto cold water (1.5 L) that was placed in an ice bath. The aqueous layer was extracted with EtOAc (250 mL×2) and then washed successively with saturated NaHCO$_3$ (1 L), brine (1 L) and the organic layer was evaporated under reduced pressure to give a dark brown oil. This oil was dissolved in minimal DCM and passed through a plug of silica gel eluting with 100% Hexanes (3.0 L) to remove minor upper impurities, then 20% EtOAc/ Hexanes to collect the major spot. Concentration of the solvent provided the alkylated product (269 g, 87%) as a brown oil which was used without further purification.

Selective Cleavage of the Isopropylidine

The crude oil (269 g, 0.67 moles), was dissolved in acetic acid (2.2 L) and water (900 mL). The reaction was allowed to proceed for 16 hours at room temperature. The reaction was follow by tlc (20% EtOAc/Hexanes). After completion of the reaction, most of the acetic acid was evaporated under reduced pressure and then the remaining solution was poured into a stirred mixture of EtOAc (1 L)/NaHCO$_3$ (1 L, aq. sat.) in small portions followed by NaHCO$_3$ (s) until gas evolution ceased. The organic layer was washed with water (1 L×2), brine (1 L), dried Na$_2$SO$_4$, filtered and removed under reduced pressure to give a crude yellow oil. The oil was then dissolved in minimal DCM and passed through a plug of silica gel eluting with 20% EtOAc/Hexanes (3.0 L) to remove the upper spot impurities, and then eluted with 80% EtOAc/Hexanes to give the major compound. Evaporation of the solvent gave the crude product (201 g, 82%) as a light yellow oil. (Rf=0.22, 20% EtOAc/hexanes).

Selective Silylation of the Primary Hydroxy Group

The crude compound (105 g, 0.293 moles), was dissolved in anhydrous DMF (1 L) followed by the addition of imidazole (39.9 g, 0.58 moles). The resulting yellow solution was cooled to 0° C. in ice-bath while stirring under nitrogen. tert-Butyldimethylsilyl chloride (TBDMSCl, 48.5 ml, 0.322 moles) dissolved in a minimal amount of DMF was added drop-wise over a 40-minute period. The ice-bath, initially at 0° C. upon complete addition, was allowed to come to room temperature and stirring continued for an additional 16 hours. The reaction was complete at this time, as determined by tlc (Rf=0.56, 20% EtOAc/hexanes). The reaction was then quenched by addition of MeOH (50 mL). Water (1 L) and EtOAc (500 mL) were then added and the organic was washed with, saturated NaHCO$_3$ (1 L) and brine (1 L) and then dried (Na$_2$SO$_4$), filtered and the solvent removed under reduced pressure to give compound 2 (139.0 g), as a yellow oil. $^1$H NMR (300 MHz, CDCl$_3$+2% D$_2$O): δ 7.7 and 7.4 (m, 7H, Nap), 5.86 (d, 1H, J=3.6 Hz), 4.7 (m, 2H), 4.54 (d, 1H, J=5.7 Hz), 4.08 (s, 2H), 3.9-4.0 (m, 1H), 3.7-3.8 (m, 2H), 1.39 (s, 1H, CH$_3$), 1.24 (s, 1H, CH$_3$), 0.82 (s, 9H, tBu), 0.02 (s, 6H, SiMe$_2$). $^{13}$C NMR (75 MHz, CDCl$_3$+2% D$_2$O): δ 135.1, 133.3, 133.1, 128.3, 128.0, 127.7, 126.6, 126.2, 126.0, 125.7, 111.7, 105.2, 82.6, 81.9, 79.6, 72.6, 68.6, 64.5, 26.7, 26.3, 25.9, 18.3, −5.4. LCMS (Method CN$_1$), retention time=1.8 min, m/z=497.1 (M+Na), >98% purity.

Compound 3

Oxalyl chloride (12.2 mL, 145 mmoles) and CH$_2$Cl$_2$ (280 mL) were added to a 2 L round bottom flask fitted with two addition funnels. One addition funnel contained DMSO (20.5 mL, 289 mmoles) in CH$_2$Cl$_2$ (30 mL), while the other funnel contained compound 2 (45.75 g, 96.4 mmoles) dissolved in CH$_2$Cl$_2$ (380 mL). The round bottom was then cooled to −78° C. under nitrogen, and the DMSO solution was added dropwise over 15 minutes. After stirring an additional 50 minutes, the solution of compound 2 was added dropwise over 15 min. After stirring an additional 30 minutes, Et$_3$N (60 mL, 434 mmoles) was added over 10 minutes and the reaction was allowed to proceed at room temperature for 30 minutes. The reaction was then quenched with NH$_4$Cl (sat, 150 mL), and the organic layer was washed successively with 10% citric acid (1 L), sodium bicarbonate (sat, 1 L), and brine (1 L). The organic layer was then dried over Na$_2$SO$_4$, concentrated and filtered thru silica gel (20% EtOAc/hexanes) to give 42.4 g (93%) of the crude ketone, which was used directly in the next step without further purification. tlc, (Rf=0.55, 20% EtOAc/hexanes); LCMS (Method CN$_1$), retention time=2.1 min, m/z=473.1 (M+H), 495.1 (M+Na), 967.3 (2M+Na). The crude ketone (39 g, 82.5 mmoles) in THF (240 mL) was added to a 1 L round bottom flask equipped with an addition funnel containing 1.0 M vinyl magnesiumbromide in THF (125 mL). The flask was cooled in an ice bath and the Grignard reagent was then added dropwise over 10 minutes. The reaction was then allowed to proceed at room temperature for 1.5 h, and quenched with NH$_4$Cl (sat, 150 mL). Et$_2$O (400 mL) was added and the organic layer was washed with brine (1 L). The organic layer was then passed through a plug of silica gel (eluting with Et$_2$O as necessary) and then concentrated to give a quantitative yield of compound 3, which was about 90% pure, and used directly in the next step. Rf=0.55, 20% EtOAc/hexanes; $^1$H NMR (300 MHz, CDCl$_3$): −7.79-7.90 and 7.47-7.56 (m, 7H, Nap), 6.11 (dd, 1H, J=16.2, 9.6 Hz, =CH—), 6.08 (d, 1H, J=3.9 Hz, H-1), 5.49 (dd, 1H, J=17.4, 1.5 Hz, =CH$_2$); 5.22 (dd, 1H, J=12.3, 1.5 Hz, =CH$_2$), 4.91 and 4.72 (ABq, 2H, CH$_2$), 4.71 (d, 1H, J=4.2 Hz, H-2), 4.38 (d, 1H, J=3.0 Hz, H-4), 4.24 (d, 1H, J=2.7 Hz, H-3), 3.92 (s, 1H, OH), 3.63 (d, 1H, J=9.6 Hz, 6a), 3.47 (d, 1H, J=9.6 Hz, 6b), 1.53 (s, 3H, CH$_3$), 1.38 (s, 3H, CH$_3$), 0.86 (s, 9H, C(CH$_3$)$_3$), −0.0 (s, 3H, SiMe), −0.08 (s, 3H, SiMe). $^1$H NMR matched closely with the OBn derivative from *Tetrahedron Lett.*, 1993, 1653. LCMS (Method DR1), m/z=501.1 (M+H), 523.2 (M+Na).

Compound 4

Hydrolysis of TBS and Isopropylidine

To the mostly pure compound 3 (41.3 g, 82.5 mmoles) and Amberlite (IR-120 H$^{30}$ Strongly Acidic ion-exchange resin, 80 g), was added 1,4-dioxane (275 mL) and H$_2$O (230 mL). This was heated at 90° C. for 36 hours, and then filtered hot through celite and evaporated to dryness. The resultant crude solid was then dried for 12 hours at 50° C. over P$_2$O$_5$.

Acetylation of the Hydrolyzed Material

The crude white solid was treated with pyridine (290 mL) and Ac$_2$O (78 mL, 10 equiv) was then added dropwise followed by DMAP (120 mg). The reaction proceeded at room temperature for 16 hours and then the solvent was evaporated and coevaporated with toluene (3×100 mL). The major product was purified by silica gel chromatography (25% EtOAc/hexanes to 35% EtOAc/hexanes) to give the crude tetraacetate, compound 4 (31.4 g, 74%) as a clear white foam. TLC (Rf=0.27, 40% EtOAc/hexanes). $^1$H NMR (300 MHz, CDCl$_3$): −7.83-7.79, 7.68, 7.5-7.4, 7.35 and 7.32 (m, 7H, Nap), 5.95-5.87 (m, 3H, CH=CH and H1), 5.63 (dd, 1H, J=8.7, 3.3 Hz, =CH), 5.46 (d, 1H, J=9.9 Hz, H4), 5.25 (dd, 1H, J=9.3, 8.4 Hz, H2), 4.76 (s, 2H, CH$_2$Nap), 4.14 and 3.71 (d, J=12.4 Hz, H6), 3.79 (dd, 1H, J=9.8, 9.8 Hz, H3), 2.10 (s, 6H, Ac×2), 1.95 (s, 3H, Ac), 1.90 (s, 3H, Ac). $^{13}$C NMR (75 MHz, CDCl$_3$+2% D$_2$O): δ 170.7, 169.5, 169.1, 169.0, 135.2, 133.2, 133.0, 129.8, 128.3, 127.9, 127.7, 126.3 (2C), 126.1, 125.5, 122.03, 88.9, 78.5, 78.1, 74.6, 72.6, 69.5, 65.2, 20.9 (3C), 20.8. LCMS (Method CN1), retention time=1.47 min, m/z=537.1 (M+Na), purity=99%.

Compound 5

Vorbruggen Coupling and Deacetylation

N,O-Bis(trimethylsilyl)acetamide (BSA, 54.7 mL, 224 mmol) was added to a stirred suspension of uracil (10.2 g, 90.7 mmol) and compound 4 (31.1 g, 60.4 mmoles) in dry acetonitrile (300 mL). After stirring at rt for 30 min a clear solution was observed, and the reaction was cooled to 0° C. under nitrogen. Trimethylsilyfluoromethanesulfonate (TMSOTf, 21.9 mL, 121 mmol) was added and after the reaction was stirred at rt for 15 min, it was transferred to a preheated oil bath at 80° C. After stirring for 4 h at 80° C., the reaction was cooled to rt and MeOH (20 mL), EtOAc (250 mL) and H$_2$O (400 mL) were added. The organic phase was then sequentially washed with sat. NaHCO$_3$, brine, dried (Na$_2$SO$_4$) and concentrated to provide the crude triacetate. TLC(Rf=0.60, 80% EtOAc/hexanes). LCMS (Method DRHI), m/z=567.1 (M+H). The crude nucleoside was treated with 7N MeOH/NH$_3$ (300 mL) at 50° C. overnight and then evaporated to dryness. The major product was purified by silica gel chromatography (2% MeOH/CH$_2$Cl$_2$ to 6% MeOH/CH$_2$Cl$_2$) to give the triol compound 5 (17.75 g, 67%) as a white solid. TLC(Rf=0.25, 8% MeOH/CH$_2$Cl$_2$). $^1$H NMR (300 MHz, DMSO-d$_6$/2% D$_2$O): δ 7.9-7.8 (m, 5H, Nap and H6), 7.62, 7.59, and 7.53-7.46 (m, 3H, Nap), 6.07 (dd, 1H, J=11.9, 17.3 Hz, C=CH), 5.68 (d, 1H, J=3.0 Hz, H5), 5.66 (s, 1H, H1'), 5.45-5.39 (m, 2H, C=CH$_2$), 4.99 (s, 2H, CH$_2$ONap), 3.93 (d, 1H, J=9.6 Hz, H4'), 3.67 (dd, 1H, J=8.9, 8.9 Hz, H2'), 3.43 (dd, 1H, J=9.6, 12.0 Hz, H3'), 3.16 and 3.42 (d, 2H, J=8.9 Hz, 6'-CH$_2$). $^{13}$C NMR (75 MHz, DMSO-d$_6$/2% D$_2$O): δ 162.8 (C4), 150.6 (C2), 141.4 (C6), 136.8 (quat), 132.6 (quat), 132.5 (=CH—), 132.0 (quat), 127.3, 127.2, 127.1, 125.8, 125.7, 125.3, * 117.9 (=CH$_2$), 101.6 (C5), 82.3 (C3'), 81.3 (C5'), 77.8 (C1'), 73.5 (CH$_2$ONap), 71.1 (C2'), 68.4 (C4'), 64.8 (6'-CH$_2$). *Between 127.3 and 125.3 lies one additional carbon that overlaps one of the others. LCMS (Method G1), retention time=2.09 min, m/z=463.1 (M+Na), purity >99%.

Compound 6

Benzylidine Formation

To a stirred mixture of triol compound 5 (16.1 g, 36.5 mmoles) in dry DMF (180 mL) was added camphorsulphonic acid (CSA, 850 mg) followed by benzaldehyde dimethylacetal (BDMA, 22 mL, 146 mmoles). This was stirred at 50° C., and after two hours additional CSA (600 mg) and BDMA (6 mL) were added. After an additional 2 h, the reaction mixture was cooled to rt and partitioned between EtOAc (300 mL) and a NaHCO$_3$ (sat)/H$_2$O (500 mL, 3:2). The organic layer was then washed with brine twice, and the aqueous layers were back-extracted with additional portions of EtOAc. The combined organic layers were dried over Na$_2$SO$_4$, and evaporated to give the crude benzylidine. The crude product was purified by silica gel chromatography (2% MeOH/CH$_2$Cl$_2$ to 5% MeOH/CH$_2$Cl$_2$) to give the benzylidine compound 6 (18.6 g, 96%) as a white solid. The final compound contained some DMF as determined by $^1$H NMR and did not interfere the subsequent step. TLC (Rf=0.45, 8% MeOH/CH$_2$Cl$_2$). $^1$H NMR (300 MHz, DMSO-d$_6$/2% D$_2$O): δ 7.9-7.8 (m, 5H, Nap and H6), 7.71-7.78 and 7.51-7.41 (m, 8H, Nap, Ph), 6.32 (dd, 3H, J=11.1, 18.2 Hz, C=CH), 5.84 (d, 1H, J=9.3 Hz, H1'), 5.77 (s, 1H, benzylidine CH), 5.72 (d, 1H, J=7.8 Hz, H5), 5.61-5.56 (m, 2H, C=CH$_2$), 4.96 (s, 2H, CH$_2$ONap), 4.06 (d, 1H, J=10.5 Hz, H4'), 4.0-3.7 (m, 4H, H2', H3', and 6'-CH$_2$). $^{13}$C NMR (75 MHz, DMSO-d$_6$/2% D$_2$O): δ 162.8 (C4), 150.4 (C2), 140.8 (C6), 136.9 (quat), 136.0 (quat), 134.5 (=CH—), 132.2 (quat), 131.9 (quat), 128.5, 127.7, 127.1, 127.0, 125.7, 125.5, 125.3, 125.2, 125.1*, 118.0 (=CH$_2$), 101.8 (benzylidine CH), 101.2 (C5), 80.8 (CH), 78.6 (C1'), 77.9 (CH), 75.5 (6'-CH$_2$), 72.9 (CH$_2$ONap), 71.5 (CH), 70.6 (quat). *Between 128.5 and 125.1 lies one additional carbon that overlaps one of the others. LCMS (Method G1), retention time=3.70 min, m/z=529.1 (M+H), 551.1 (M+Na), purity >99%.

Compound 7

Dihydroxylation, Periodate Cleavage and Reduction to the Alcohol

To as stirred solution of compound 6 (45 g, 85 mmoles) in 95% acetone (aq, 350 mL) was added N-methylmorpholine oxide (48 g, 409 mmoles) and 2.5% OsO$_4$ in isopropanol (70 mg OsO$_4$), and the reaction was allowed to stir at room temperature for 4 days. At that time, the reaction was filtered thru celite and silica gel, and eluted thoroughly with acetone. The resultant crude product was purified by column chromatography (2.5% to 5% methanol/DCM) to give 19.74 g of the diol, which was immediately treated with THF (175 mL), H$_2$O (175 mL) and NaIO$_4$ (15 g, 70 mmoles). After 1 hour, water and EtOAc were added and the organic was washed with, saturated NaHCO$_3$ and brine and then dried (Na$_2$SO$_4$), filtered and the solvent removed under reduced pressure to give the crude aldehyde. This compound was immediately treated with 4 equivalents of NaBH$_4$ in methanol at 0° C. for 1 hour, and then water and EtOAc were added and the organic was washed with, 10% citric acid (aq) and brine and then dried (Na$_2$SO$_4$), filtered and the solvent removed under reduced pressure to give the crude alcohol. The reaction was purified by silica gel chromatography, eluting with methanol/DCM to give compound 7 (40% overall yield). $^1$H NMR and LCMS was consistent with structure.

Compound 8

Anhydro Formation

To a stirred 0° C. mixture of compound 7 (1.28 g, 2.4 mmoles) and triphenyl phosphine (2.2 g, 8.4 mmoles) in dry THF (20 mL) was added DIAD (1.6 mL, 8.4 mmoles) dropwise. After stirring at room temp for 18 hours, water and DCM were added and the organic was washed with brine and then dried (Na$_2$SO$_4$), filtered and the solvent removed under reduced pressure to give the crude bicyclic product. This was purified by silica gel chromatography (2% methanol/DCM to 10% methanol/DCM) to give the pure compound 8 (1.11 g, 90%). $^1$H NMR and LCMS was consistent with structure.

Compound 9 and 10

Ring Closure to the bicyclo[2.2.2]octane Ring System

Compound 8 (1.1 g, 2.15 mmoles) was dissolved in DMF (15 mL) and treated with NaH (60% in mineral oil, 6.4 mmoles) for 15 minutes. At that time, NH$_4$Cl and EtOAc were added and the organic was washed with, water and brine and then dried (Na$_2$SO$_4$), filtered and the solvent removed under reduced pressure to give the crude compound. This was purified by silica gel chromatography (3% methanol/DCM) to give the pure compound 9 (866 mg, 79%) and 10 (68 mg), individually. $^1$H NMR and LCMS was consistent with structure.

Compound 11

Removal of Nap

Compound 9 (800 mg, 1.6 mmoles) was dissolved in DCM (15 mL) and treated with water (1.5 mL) and DDQ (529 mg, 2.3 mmoles). After stirring for 16 hours, water and DCM were added and the organic was washed with, saturated NaHCO$_3$ and brine and then dried (Na$_2$SO$_4$), filtered and the solvent removed under reduced pressure to give the crude alcohol. The organics were back-extracted several times with DCM. The crude compound was co-evaporated with methanol/DCM (10 mL) and silica gel (1 g). After drying, this was applied directly to a silica gel column, and purified by silica gel chromatography (2% to 6% methanol/DCM) to give compound 11 (409 mg, 70%). $^1$H NMR and LCMS was consistent with structure.

Compound 12

The Barton-Macombie Deoxygenation

A stirred mixture of compound 11 (388 mg, 1.04 mmoles) and DMAP (343 mg, 2.8 mmoles) in CH$_3$CN (14 mL) at 0° C. was added phenylchlorothioformate (196 μL, 1.45 mmoles). After stirring for 4 hours, the reaction mixture was evaporated to dryness. Toluene (13 mL), Bu$_4$SnH (1.65 mL, 6.24 mmoles) and AIBN (15 mg) were heated at 90° C. for 4 hours. The reaction was then evaporated to dryness, and purified by silica gel chromatography (1.5% to 3% methanol/DCM) to give compound 12 (254 mg, 68%). $^1$H NMR and LCMS was consistent with structure.

49

Compound 13
Removal of the benzylidine and DMT Protection

A stirred mixture of compound 12 (230 mg, 0.64 mmoles) was hydrogenated over 10% Pd/C (20 mg) at 40 psi for 10 hours. The reaction was filtered and evaporated and co-evaporated with toluene. After drying under reduced pressure for 16 hours, pyridine (3 mL) and DMTCl (187 mg, 0.55 mmoles) was added. The reaction was allowed to stir at room temperature for 4 hours, and water and EtOAc were added and the organic was washed with, saturated $NaHCO_3$ and brine and then dried ($Na_2SO_4$), filtered and the solvent removed under reduced pressure. The resultant foam was purified by silica gel chromatography (10% to 40% acetone/$CH_2Cl_2$) to give compound 13 (171 mg, 47%). $^1$H NMR and LCMS was consistent with structure.

Compound 14
Preparation of U-Amidite

2-Cyanoethyl N,N'-tetraisopropylphosphoramidite (0.75 μL, 0.24 mmol) was added to a solution of compound 13 (90 mg, 0.157 mmol), tetrazole (8 mg), N-methylimidazole (3 μL) in DMF (1 mL). After stirring for 8 hours at room temperature, the reaction was poured into EtOAc and the organic phase was washed with 90% brine, brine, dried ($Na_2SO_4$) and concentrated under vacuum. Purification by column chromatography ($SiO_2$, eluting with 60% to 90% EtOAc/hexanes) gave Compound 14 (99 mg, 92%) as a white solid. $^1$H NMR and LCMS was consistent with structure.

Compound 15
Conversion of U to CBz

A solution of compound 13 (114 mg, 0.20 mmoles), in $CH_3CN$ (2 mL) was treated with $Et_3N$ (1.1 mL, 7.96 mmoles) and cooled to 0° C. TMSCl (76 μL, 0.6 mmoles) was added and after 1 hour, 1,2,4-triazole (330 mg, 4.8 mmoles) was added followed by $POCl_3$ (146 μL, 1.6 mmoles). The reaction was then allowed to proceed for 4 hours at room temperature. Water and EtOAc were added and the organic was washed with, saturated $NaHCO_3$ and brine and then dried ($Na_2SO_4$), filtered and the solvent removed under reduced pressure to give the crude triazole. A prestirred mixture of NaH (48 mg, 1.2 μmoles) and benzamide (145 mg, 1.2 μmoles) was then added. After 1 hour, water and EtOAc were added and the organic was washed with, saturated $NaHCO_3$ and brine and then dried ($Na_2SO_4$), filtered and the solvent removed under reduced pressure. Triethylamine trihydroflouride (166 μL, 1.0 mmol) was added to a solution of the crude compound and triethylamine (0.06 mL, 0.4 mmol) in THF (1 mL). After stirring at room temperature for 12 hours, the reaction was poured into EtOAc and the organic layer was washed with $H_2O$, saturated $NaHCO_3$, brine, dried ($Na_2SO_4$) and concentrated. Purification by column chromatography ($SiO_2$, eluting with 20% to 40% acetone in chloroform) gave Compound 15 (73 mg, 54% overall).

Compound 16
Preparation of CBz Amidite

2-Cyanoethyl N,N'-tetraisopropylphosphoramidite (0.50 mL, 0.156 mmol) was added to a solution of compound 15 (70 mg, 1.0 μmol, tetrazole (7 mg), N-methylimidazole (3 μL) in DMF (1 mL). After stirring for 8 hours at room temperature, the reaction was poured into EtOAc and the organic phase was washed with 90% brine, brine, dried ($Na_2SO_4$) and concentrated under vacuum. Purification by column chromatography ($SiO_2$, eluting with 60% to 90% EtOAc/hexanes) gave Compound 16 (62 mg, 68%) as a white solid. $^1$H NMR and LCMS was consistent with structure.

50

Example 2

Preparation of (1S,3R,4S,7R)-7-(2-cyanoethoxy(diisopropylamino)phosphin oxy)-1-(4,4'-dimethoxytriyloxymethyl)-3-(heterocyclic base radical)-2,5-dioxa-bicyclo[2.2.2]octane (27)

Route 1:

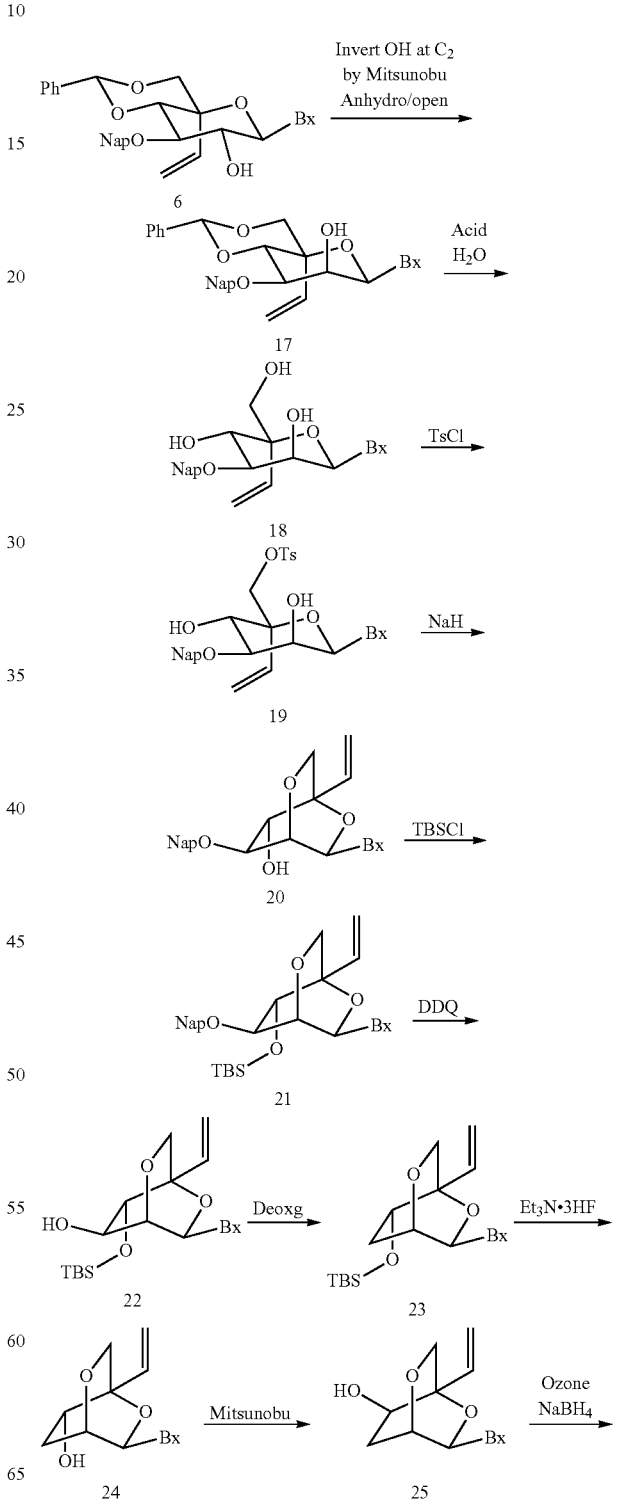

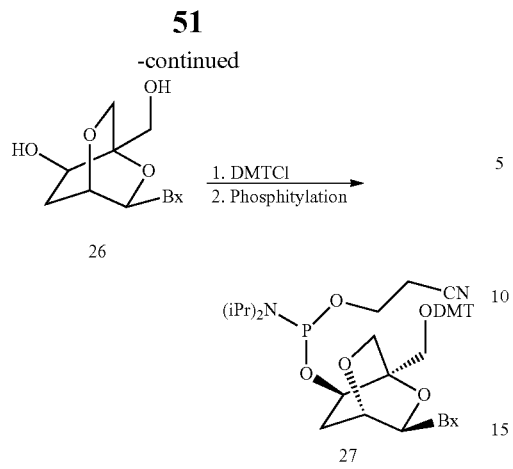
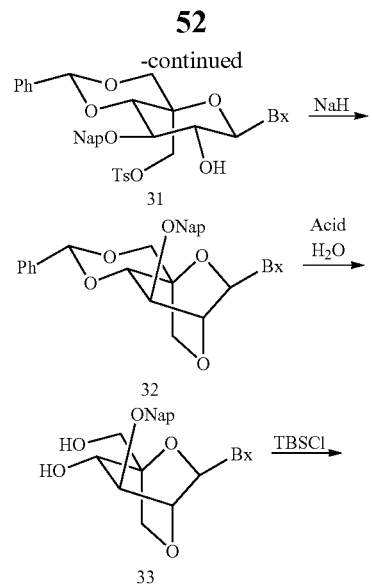
Route 2: Alternative Procedures to Prepare Compound 20
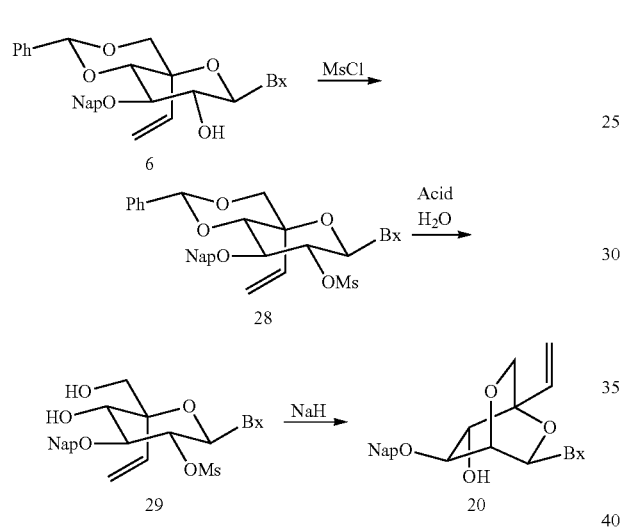
Compound 6 is prepared as per the procedures illustrated in Example 1.
Example 3
Preparation of (1R,3R,4R,8R)-8-(2-cyanoethoxy (diisopropylamino)phosphin oxy)-1-(4,4'-dimethoxytrityloxymethyl)-3-(heterocyclic base radical)-2,5-dioxa-bicyclo[2.2.2]octane (39)
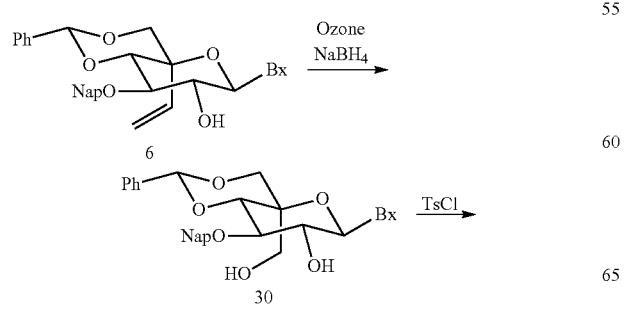
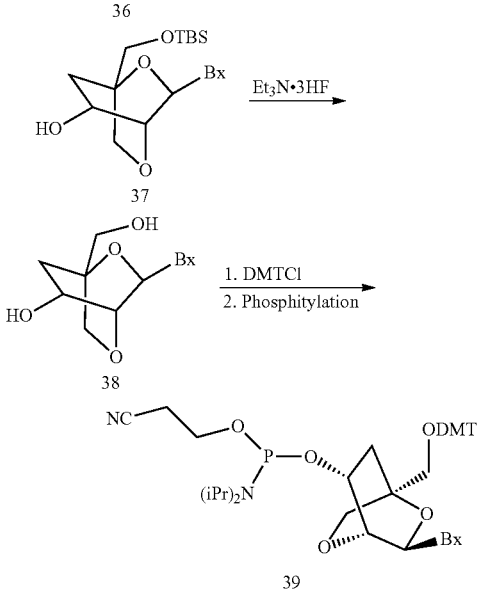
Compound 6 is prepared as per the procedures illustrated in Example 1.

Example 4
Preparation of (1S,3R,4S,8S)-8-(2-cyanoethoxy(diisopropylamino)phosphin oxy)-1-(4,4'-dimethoxytrityloxymethyl)-3-(heterocyclic base radical)-2,5-dioxa-bicyclo[2.2.2]octane (47 U, 49 C)
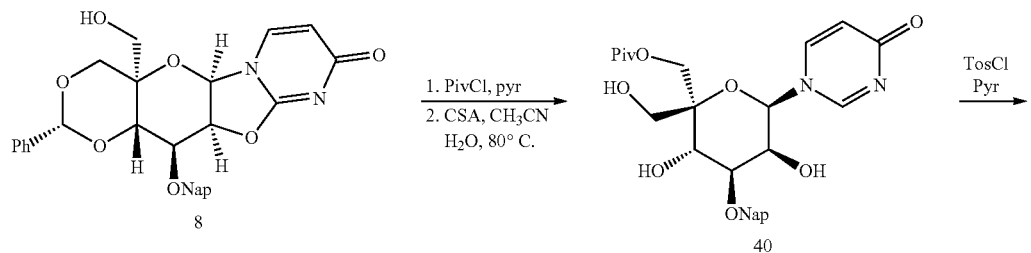
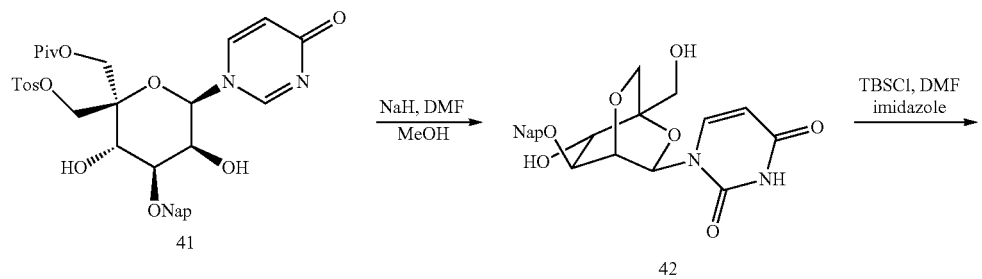
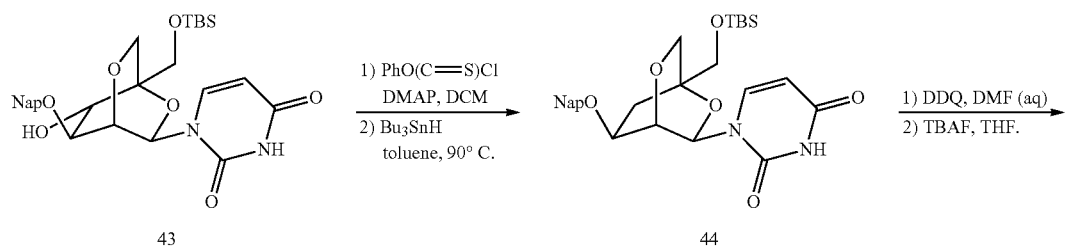
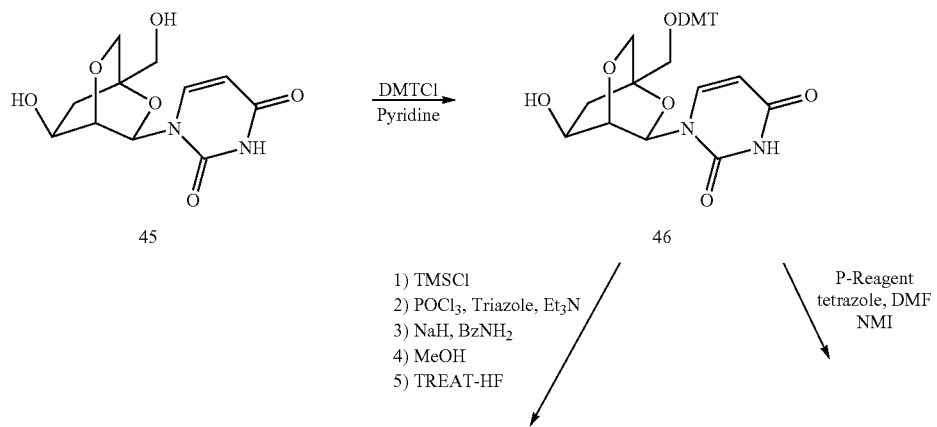

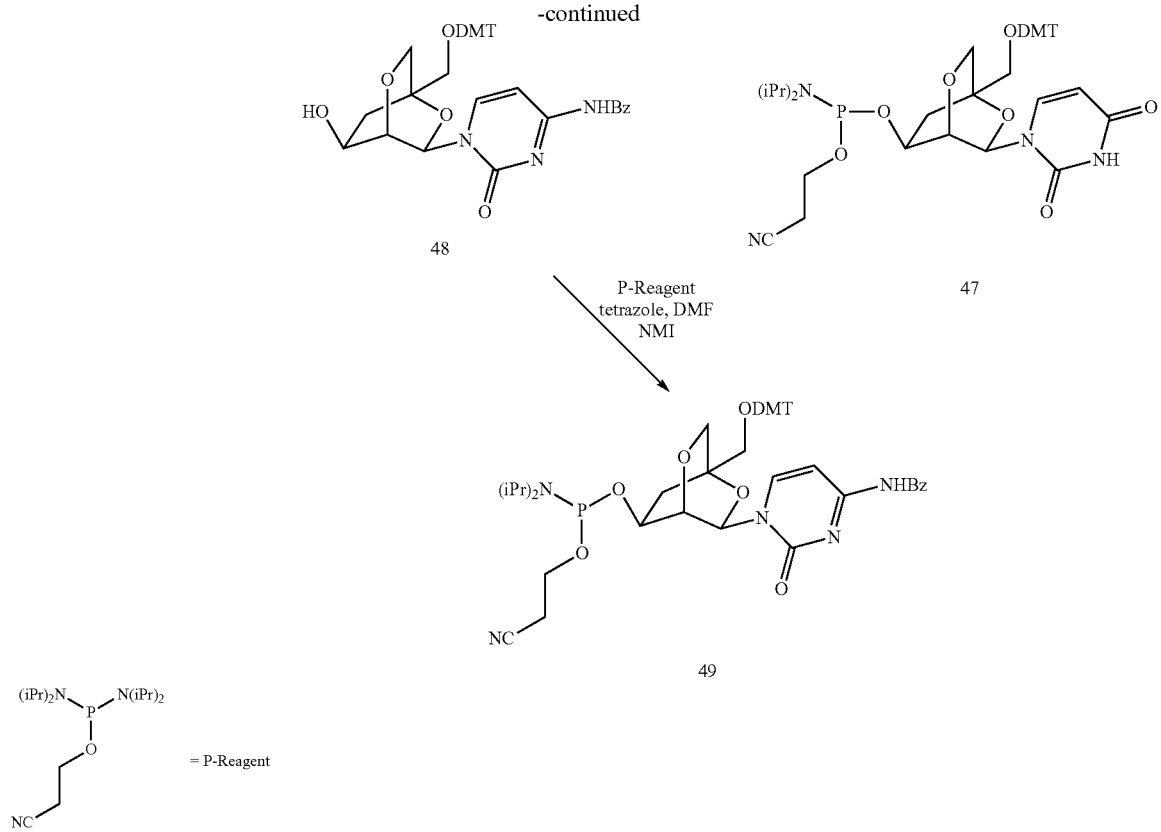

Compound 8 was prepared as per the procedures illustrated in Example 1.

Compound 40
Protection of the Primary Hydroxyl and Hydrolysis of the Anyhdro Nucleoside To a stirred solution of compound 8 (5.56 g, 10.8 mmoles) in $CH_2Cl_2$ (80 mL) was added DMAP (800 mg), Hunig's Base (3.8 mL, 21.6 mmoles), and pivaloyl chloride (PivCl, 2.0 mL, 16.2 mmoles) at 0° C. The reaction was then stirred at room temperature for 3 hours, at which time $NaHCO_3$ (sat) and EtOAc were added and the organic was washed with, saturated $NaHCO_3$ and brine and then dried ($Na_2SO_4$), filtered and the solvent removed under reduced pressure to give the crude compound. Purification by column chromatography ($SiO_2$, eluting with 3% $MeOH/CH_2Cl_2$) gave (3.34 g, 52%) as a white solid. $^1H$ NMR and LCMS was consistent with structure. To a stirred solution of the crude ester (3.28 g) in $CH_3CN/H_2O$ (90 mL, 7:2) was added camphorsuphonic acid (CSA, 500 mg). This was heated at 70° C. for 5 hours, at which time the solvent was removed under reduced pressure to give the crude compound. Purification by column chromatography ($SiO_2$, eluting with 4 to 6% $MeOH/CH_2Cl_2$) gave Compound 40 (2.43 g, 84%) as a white solid. $^1H$ NMR and LCMS were consistent with structure.

Compound 41
Tosylation of the Primary Hydroxy Group

To a stirred solution of compound 40 (2.36 g, 4.46 mmoles) in pyridine (50 mL) was added tosyl chloride (1.3 g, 6.7 mmoles). The reaction was then stirred at room temperature for 24 hours, at which time $NaHCO_3$ (sat) and $H_2O$ were added and the organic was washed with, saturated $NaHCO_3$ and brine and then dried ($Na_2SO_4$), filtered and the solvent removed under reduced pressure to give the crude compound. Purification by column chromatography ($SiO_2$, eluting with 3 to 10% $MeOH/CH_2Cl_2$) gave compound 41 (1.92 g, 63%) as a white solid. $^1H$ NMR and LCMS were consistent with structure.

Compound 42
Ring Closure to the bicyclo[2.2.2]octane Ring System

Compound 41 (1.7 g, 2.5 mmoles) was dissolved in DMF (14 mL) and treated with NaH (60% in mineral oil, 200 mg, 5.0 mmoles) for 15 minutes. At that time, $NH_4Cl$ and EtOAc were added and the organic was washed with, water and brine and then dried ($Na_2SO_4$), filtered and the solvent removed under reduced pressure to give the crude compound. This was purified by precipitating from $CH_2Cl_2$/hexanes to give pure compound 42 (464 mg). $^1H$ NMR and LCMS were consistent with structure.

Compound 43
TBS Protection

Compound 42 (416 mg, 0.98 mmoles) was dissolved in anhydrous DMF (5 mL) followed by the addition of imidazole (133 g, 2.0 mmoles). The resulting yellow solution was cooled to 0° C. in ice-bath while stirring under nitrogen. tert-butyldimethylsilyl chloride (TBSCl, 191 mg, 1.3 mmoles) was added and stirring continued for an additional 16 hours at room temperature. The reaction was then quenched by addition of MeOH. Water and EtOAc were then added and the organic was washed with, saturated $NaHCO_3$ and brine and then dried ($Na_2SO_4$), filtered and the solvent removed under reduced pressure to give crude compound 43. Purification by column chromatography ($SiO_2$, eluting with 4 to 6% $MeOH/CH_2Cl_2$) gave compound 43 (600 mg, 94%) as a white solid. $^1H$ NMR and LCMS were consistent with structure.

Compound 44
The Barton-Macombie Deoxygenation.

Compound 42 (1.25 g, 2.3 mmoles) was deoxygenated as in the procedure for compound 12 to give compound 44 (792 mg). $^1$H NMR and LCMS were consistent with structure.

Compound 45
Removal of Nap and TBS Groups.

Compound 44 (743 mg, 1.42 mmoles) was dissolved in DCM (13 mL) and treated with water (1 mL) and DDQ (341 mg, 2.1 mmoles). After stirring for 6 hours, water and DCM were added and the organic was washed with, saturated NaHCO$_3$ and brine and then dried (Na$_2$SO$_4$), filtered and the solvent removed under reduced pressure to give the crude alcohol. The organics were back-extracted several times with DCM. The combined organics were evaporated and used in the next step. The crude alcohol was deprotected according to (Kaburagi, Y.; Kishi, Y. Operationally Simple and Efficient Workup Procedure for TBAF-Mediated Desilylation: Application to Halichondrin Synthesis. *Org. Lett.* 2007, 9, 723-726) to give compound 45 (328 mg).

Compound 46
DMT Protection

To a stirred mixture of compound 45 (190 mg, 0.70 mmoles) in pyridine (5 mL) was added DMTCl (286 mg, 0.84 mmoles). The reaction was allowed to stir at room temperature for 4 hours, and water and EtOAc were added and the organic was washed with, saturated NaHCO$_3$ and brine and then dried (Na$_2$SO$_4$), filtered and the solvent removed under reduced pressure. Purification by column chromatography (SiO$_2$, eluting with 4 to 10% MeOH/CH$_2$Cl$_2$) gave compound 46 (298 mg, 74%) as a white solid. $^1$H NMR and LCMS were consistent with structure.

Compound 47
Preparation of U-Amidite

2-Cyanoethyl N,N'-tetraisopropylphosphoramidite (104 μL, 0.33 mmol) was added to a solution of compound 46 (125 mg, 0.218 mmol), tetrazole (12 mg), N-methylimidazole (4 μL) in DMF (1 mL). After stirring for 4 hours at room temperature, the reaction was poured into EtOAc and the organic phase was washed with 90% brine, brine, dried (Na$_2$SO$_4$) and concentrated under vacuum. Purification by column chromatography (SiO$_2$, eluting with 60% EtOAc/hexanes) gave Compound 47 (140 mg) as a white solid. $^{31}$P NMR was consistent with structure.

Compound 48
Conversion of U to CBz

Compound 46 (124 mg, 180 μmoles) was converted into compound 48 (104 mg, 73%) using the procedure for compound 15, except TBSCl was used instead of TMSCl.

Compound 49
Preparation of CBz Amidite

2-Cyanoethyl N,N'-tetraisopropylphosphoramidite (0.53 mL, 0.15 mmol) was added to a solution of compound 48 (75 mg, 0.11 mmol), tetrazole (6 mg), N-methylimidazole (1 drop) in DMF (1 mL). After stirring for 4 hours at room temperature, the reaction was poured into EtOAc and the organic phase was washed with 90% brine, brine, dried (Na$_2$SO$_4$) and concentrated under vacuum. Purification by column chromatography (SiO$_2$, eluting with 60% EtOAc/hexanes) gave Compound 49 (80 mg) as a white solid. $^{31}$P NMR was consistent with structure.

Example 5

Synthesis of Nucleoside Phosphoramidites

The preparation of nucleoside phosphoramidites is performed following procedures that are illustrated herein and in the art such as but not limited to U.S. Pat. No. 6,426,220 and published PCT WO 02/36743.

Example 6

Synthesis of Oligomeric Compounds

The oligomeric compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as alkylated derivatives and those having phosphorothioate linkages.

Oligomeric compounds: Unsubstituted and substituted phosphodiester (P=O) oligomeric compounds, including without limitation, oligonucleotides can be synthesized on an automated DNA synthesizer (Applied Biosystems model 394) using standard phosphoramidite chemistry with oxidation by iodine.

In certain embodiments, phosphorothioate internucleoside linkages (P=S) are synthesized similar to phosphodiester internucleoside linkages with the following exceptions: thiation is effected by utilizing a 10% w/v solution of 3,H-1,2-benzodithiole-3-one 1,1-dioxide in acetonitrile for the oxidation of the phosphite linkages. The thiation reaction step time is increased to 180 sec and preceded by the normal capping step. After cleavage from the CPG column and deblocking in concentrated ammonium hydroxide at 55° C. (12-16 hr), the oligomeric compounds are recovered by precipitating with greater than 3 volumes of ethanol from a 1 M NH$_4$OAc solution. Phosphinate internucleoside linkages can be prepared as described in U.S. Pat. No. 5,508,270.

Alkyl phosphonate internucleoside linkages can be prepared as described in U.S. Pat. No. 4,469,863.

3'-Deoxy-3'-methylene phosphonate internucleoside linkages can be prepared as described in U.S. Pat. No. 5,610,289 or 5,625,050.

Phosphoramidite internucleoside linkages can be prepared as described in U.S. Pat. No. 5,256,775 or U.S. Pat. No. 5,366,878.

Alkylphosphonothioate internucleoside linkages can be prepared as described in published PCT applications PCT/US94/00902 and PCT/US93/06976 (published as WO 94/17093 and WO 94/02499, respectively).

3'-Deoxy-3'-amino phosphoramidate internucleoside linkages can be prepared as described in U.S. Pat. No. 5,476,925.

Phosphotriester internucleoside linkages can be prepared as described in U.S. Pat. No. 5,023,243.

Borano phosphate internucleoside linkages can be prepared as described in U.S. Pat. Nos. 5,130,302 and 5,177,198.

Oligomeric compounds having one or more non-phosphorus containing internucleoside linkages including without limitation methylenemethylimino linked oligonucleosides, also identified as MMI linked oligonucleosides, methylenedimethylhydrazo linked oligonucleosides, also identified as MDH linked oligonucleosides, methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone oligomeric compounds having, for instance, alternating MMI and P=O or P=S linkages can be prepared as described in U.S. Pat. Nos. 5,378,825, 5,386,023, 5,489,677, 5,602,240 and 5,610,289.

Formacetal and thioformacetal internucleoside linkages can be prepared as described in U.S. Pat. Nos. 5,264,562 and 5,264,564.

Ethylene oxide internucleoside linkages can be prepared as described in U.S. Pat. No. 5,223,618.

Example 7

Isolation and Purification of Oligomeric Compounds

After cleavage from the controlled pore glass solid support or other support medium and deblocking in concentrated ammonium hydroxide at 55° C. for 12-16 hours, the oligomeric compounds, including without limitation oligonucleotides and oligonucleosides, are recovered by precipitation out of 1 M $NH_4OAc$ with >3 volumes of ethanol. Synthesized oligomeric compounds are analyzed by electrospray mass spectroscopy (molecular weight determination) and by capillary gel electrophoresis. The relative amounts of phosphorothioate and phosphodiester linkages obtained in the synthesis is determined by the ratio of correct molecular weight relative to the −16 amu product (+/−32+/−48). For some studies oligomeric compounds are purified by HPLC, as described by Chiang et al., J. Biol. Chem. 1991, 266, 18162-18171. Results obtained with HPLC-purified material are generally similar to those obtained with non-HPLC purified material.

Example 8

Synthesis of Oligomeric Compounds using the 96 Well Plate Format

Oligomeric compounds, including without limitation oligonucleotides, can be synthesized via solid phase P(III) phosphoramidite chemistry on an automated synthesizer capable of assembling 96 sequences simultaneously in a 96-well format. Phosphodiester internucleoside linkages are afforded by oxidation with aqueous iodine. Phosphorothioate internucleoside linkages are generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites can be purchased from commercial vendors (e.g. PE-Applied Biosystems, Foster City, Calif., or Pharmacia, Piscataway, N.J.). Non-standard nucleosides are synthesized as per standard or patented methods and can be functionalized as base protected beta-cyanoethyldiisopropyl phosphoramidites.

Oligomeric compounds can be cleaved from support and deprotected with concentrated $NH_4OH$ at elevated temperature (55-60° C.) for 12-16 hours and the released product then dried in vacuo. The dried product is then re-suspended in sterile water to afford a master plate from which all analytical and test plate samples are then diluted utilizing robotic pipettors.

Example 9

Analysis of Oligomeric Compounds using the 96-Well Plate Format

The concentration of oligomeric compounds in each well can be assessed by dilution of samples and UV absorption spectroscopy. The full-length integrity of the individual products can be evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition is confirmed by mass analysis of the oligomeric compounds utilizing electrospray-mass spectroscopy. All assay test plates are diluted from the master plate using single and multi-channel robotic pipettors. Plates are judged to be acceptable if at least 85% of the oligomeric compounds on the plate are at least 85% full length.

Example 10

In Vitro Treatment of Cells with Oligomeric Compounds

The effect of oligomeric compounds on target nucleic acid expression is tested in any of a variety of cell types provided that the target nucleic acid is present at measurable levels. This can be routinely determined using, for example, PCR or Northern blot analysis. Cell lines derived from multiple tissues and species can be obtained from American Type Culture Collection (ATCC, Manassas, Va.).

The following cell type is provided for illustrative purposes, but other cell types can be routinely used, provided that the target is expressed in the cell type chosen. This can be readily determined by methods routine in the art, for example Northern blot analysis, ribonuclease protection assays or RT-PCR.

b.END cells: The mouse brain endothelial cell line b.END was obtained from Dr. Werner Risau at the Max Plank Institute (Bad Nauheim, Germany). b.END cells are routinely cultured in DMEM, high glucose (Invitrogen Life Technologies, Carlsbad, Calif.) supplemented with 10% fetal bovine serum (Invitrogen Life Technologies, Carlsbad, Calif.). Cells are routinely passaged by trypsinization and dilution when they reached approximately 90% confluence. Cells are seeded into 96-well plates (Falcon-Primaria #353872, BD Biosciences, Bedford, Mass.) at a density of approximately 3000 cells/well for uses including but not limited to oligomeric compound transfection experiments.

Experiments involving treatment of cells with oligomeric compounds:

When cells reach appropriate confluency, they are treated with oligomeric compounds using a transfection method as described.

LIPOFECTIN™

When cells reached 65-75% confluency, they are treated with one or more oligomeric compounds. The oligomeric compound is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of the oligomeric compound(s) and a LIPOFECTIN™ concentration of 2.5 or 3 μg/mL per 100 nM oligomeric compound(s). This transfection mixture is incubated at room temperature for approximately 0.5 hours. For cells grown in 96-well plates, wells are washed once with 100 μL, OPTI-MEM™-1 and then treated with 130 μL of the transfection mixture. Cells grown in 24-well plates or other standard tissue culture plates are treated similarly, using appropriate volumes of medium and oligomeric compound(s). Cells are treated and data are obtained in duplicate or triplicate. After approximately 4-7 hours of treatment at 37° C., the medium containing the transfection mixture is replaced with fresh culture medium. Cells are harvested 16-24 hours after treatment with oligomeric compound(s).

Other suitable transfection reagents known in the art include, but are not limited to, CYTOFECTIN™, LIPOFECTAMINE™, OLIGOFECTAMINE™, and FUGENE™.

Other suitable transfection methods known in the art include, but are not limited to, electroporation.

Example 11

Real-Time Quantitative PCR Analysis of Target mRNA Levels

Quantitation of target mRNA levels is accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

RT and PCR reagents are obtained from Invitrogen Life Technologies (Carlsbad, Calif.). RT, real-time PCR is carried out by adding 20 μL PCR cocktail (2.5×PCR buffer minus $MgCl_2$, 6.6 mM $MgCl_2$, 375 μM each of dATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 μL total RNA solution (20-200 ng). The RT reaction is carried out by incubation for 30 minutes at 48° C. Following a 10 minute incubation at 95° C. to activate the PLATINUM® Taq, 40 cycles of a two-step PCR protocol are carried out: 95° C. for 15 seconds (denaturation) followed by 60° C. for 1.5 minutes (annealing/-extension).

Gene target quantities obtained by RT, real-time PCR are normalized using either the expression level of GAPDH, a gene whose expression is constant, or by quantifying total RNA using RIBOGREEN™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RIBOGREEN™ are taught in Jones, L. J., et al, (Analytical Biochemistry, 1998, 265, 368-374).

In this assay, 170 μL of RIBOGREEN™ working reagent (RIBOGREEN™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 485 nm and emission at 530 nm.

Example 12

Analysis of Inhibition of Target Expression

Antisense modulation of a target expression can be assayed in a variety of ways known in the art. For example, a target mRNA levels can be quantitated by, e.g., Northern blot analysis, competitive polymerase chain reaction (PCR), or real-time PCR. Real-time quantitative PCR is presently desired. RNA analysis can be performed on total cellular RNA or poly(A)+ mRNA. One method of RNA analysis of the present disclosure is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of a target can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Methods for preparation of polyclonal antisera are taught in, for example, Ausubel, F. M. et al., *Current Protocols in Molecular Biology*, Volume 2, pp. 11.12.1-11.12.9, John Wiley & Sons, Inc., 1997. Preparation of monoclonal antibodies is taught in, for example, Ausubel, F. M. et al., *Current Protocols in Molecular Biology*, Volume 2, pp. 11.4.1-11.11.5, John Wiley & Sons, Inc., 1997.

Immunoprecipitation methods are standard in the art and can be found at, for example, Ausubel, F. M. et al., *Current Protocols in Molecular Biology*, Volume 2, pp. 10.16.1-

10.16.11, John Wiley & Sons, Inc., 1998. Western blot (immunoblot) analysis is standard in the art and can be found at, for example, Ausubel, F. M. et al., *Current Protocols in Molecular Biology*, Volume 2, pp. 10.8.1-10.8.21, John Wiley & Sons, Inc., 1997. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

Example 13

Design of Phenotypic Assays and In Vivo Studies for the Use of Target Inhibitors Phenotypic Assays Once target inhibitors have been identified by the methods disclosed herein, the oligomeric compounds are further investigated in one or more phenotypic assays, each having measurable endpoints predictive of efficacy in the treatment of a particular disease state or condition.

Phenotypic assays, kits and reagents for their use are well known to those skilled in the art and are herein used to investigate the role and/or association of a target in health and disease. Representative phenotypic assays, which can be purchased from any one of several commercial vendors, include those for determining cell viability, cytotoxicity, proliferation or cell survival (Molecular Probes, Eugene, Oreg.; PerkinElmer, Boston, Mass.), protein-based assays including enzymatic assays (Panvera, LLC, Madison, Wis.; BD Biosciences, Franklin Lakes, N.J.; Oncogene Research Products, San Diego, Calif.), cell regulation, signal transduction, inflammation, oxidative processes and apoptosis (Assay Designs Inc., Ann Arbor, Mich.), triglyceride accumulation (Sigma-Aldrich, St. Louis, Mo.), angiogenesis assays, tube formation assays, cytokine and hormone assays and metabolic assays (Chemicon International Inc., Temecula, Calif.; Amersham Biosciences, Piscataway, N.J.).

In one non-limiting example, cells determined to be appropriate for a particular phenotypic assay (i.e., MCF-7 cells selected for breast cancer studies; adipocytes for obesity studies) are treated with a target inhibitors identified from the in vitro studies as well as control compounds at optimal concentrations which are determined by the methods described above. At the end of the treatment period, treated and untreated cells are analyzed by one or more methods specific for the assay to determine phenotypic outcomes and endpoints.

Phenotypic endpoints include changes in cell morphology over time or treatment dose as well as changes in levels of cellular components such as proteins, lipids, nucleic acids, hormones, saccharides or metals. Measurements of cellular status which include pH, stage of the cell cycle, intake or excretion of biological indicators by the cell, are also endpoints of interest.

Measurement of the expression of one or more of the genes of the cell after treatment is also used as an indicator of the efficacy or potency of the target inhibitors. Hallmark genes, or those genes suspected to be associated with a specific disease state, condition, or phenotype, are measured in both treated and untreated cells.

In Vivo Studies

The individual subjects of the in vivo studies described herein are warm-blooded vertebrate animals, which includes humans.

Example 14

RNA Isolation

Poly(A)+ mRNA Isolation

Poly(A)+ mRNA is isolated according to Miura et al., (Clin. Chem., 1996, 42, 1758-1764). Other methods for poly (A)+ mRNA isolation are routine in the art. Briefly, for cells grown on 96-well plates, growth medium is removed from the cells and each well is washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) is added to each well, the plate is gently agitated and then incubated at room temperature for five minutes. 55 µL of lysate is transferred to Oligo d(T) coated 96-well plates (AGCT Inc., Irvine Calif.). Plates are incubated for 60 minutes at room temperature, washed 3 times with 200 µL of wash buffer (10 mM Tris-HCl pH 7.6, 1 mM EDTA, 0.3 M NaCl). After the final wash, the plate is blotted on paper towels to remove excess wash buffer and then air-dried for 5 minutes. 60 µL of elution buffer (5 mM Tris-HCl pH 7.6), preheated to 70° C., is added to each well, the plate is incubated on a 90° C. hot plate for 5 minutes, and the eluate is then transferred to a fresh 96-well plate.

Cells grown on 100 mm or other standard plates may be treated similarly, using appropriate volumes of all solutions.

Total RNA Isolation

Total RNA is isolated using an RNEASY 96™ kit and buffers purchased from Qiagen Inc. (Valencia, Calif.) following the manufacturer's recommended procedures. Briefly, for cells grown on 96-well plates, growth medium is removed from the cells and each well is washed with 200 µL cold PBS. 150 µL Buffer RLT is added to each well and the plate vigorously agitated for 20 seconds. 150 µL of 70% ethanol is then added to each well and the contents mixed by pipetting three times up and down. The samples are then transferred to the RNEASY 96™ well plate attached to a QIAVAC™ manifold fitted with a waste collection tray and attached to a vacuum source. Vacuum is applied for 1 minute. 500 µL of Buffer RW1 is added to each well of the RNEASY 96™ plate and incubated for 15 minutes and the vacuum is again applied for 1 minute. An additional 500 µL of Buffer RW1 is added to each well of the RNEASY 96™ plate and the vacuum is applied for 2 minutes. 1 mL of Buffer RPE is then added to each well of the RNEASY 96™ plate and the vacuum applied for a period of 90 seconds. The Buffer RPE wash is then repeated and the vacuum is applied for an additional 3 minutes. The plate is then removed from the QIAVAC™ manifold and blotted dry on paper towels. The plate is then re-attached to the QIAVAC™ manifold fitted with a collection tube rack containing 1.2 mL collection tubes. RNA is then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 15

Target-Specific Primers and Probes

Probes and primers may be designed to hybridize to a target sequence, using published sequence information.

For example, for human PTEN, the following primer-probe set was designed using published sequence information (GENBANK™ accession number U92436.1, SEQ ID NO: 1).

Forward primer: AATGGCTAAGTGAAGATGACAATCAT (SEQ ID NO: 2)

Reverse primer: TGCACATATCATTACACCAGTTCGT (SEQ ID NO: 3)

And the PCR probe:
FAM-TTGCAGCAATTCACTGTAAAGCTG-GAAAGG-TAMRA (SEQ ID NO: 4), where FAM is the fluorescent dye and TAMRA is the quencher dye.

Example 16

Western Blot Analysis of Target Protein Levels

Western blot analysis (immunoblot analysis) is carried out using standard methods. Cells are harvested 16-20 h after oligonucleotide treatment, washed once with PBS, suspended in Laemmli buffer (100 μl/well), boiled for 5 minutes and loaded on a 16% SDS-PAGE gel. Gels are run for 1.5 hours at 150 V, and transferred to membrane for western blotting. Appropriate primary antibody directed to a target is used, with a radiolabeled or fluorescently labeled secondary antibody directed against the primary antibody species. Bands are visualized using a PHOSPHORIMAGER™ (Molecular Dynamics, Sunnyvale Calif.).

Example 17

In Vitro PTEN Study Using 2-10-2 Gapped Oligomers with Bicyclic Nucleoside Analogs in the Wings A 2-10-2 Gapped oligomeric compound was synthesized and tested for its ability to reduce PTEN expression in B.END cells. B.END cells were treated with the oligomeric compound indicated at a concentration of 20 and 40 nM using methods described herein. PTEN mRNA levels were measured using quantitative real-time PCR following routine methods described herein. The data represents averages from two experiments.

Tm's were assessed in 100 mM phosphate buffer, 0.1 mM EDTA, pH 7, at 260 nm using bicyclic cyclohexose nucleic acid modified oligomers and 4 μM complementary RNA.

| SEQ ID NO./ ISIS NO: | Composition (5' to 3') | Conc. (nM) | % Inhibition | Tm (° C.) |
|---|---|---|---|---|
| 05/402380 | $C_xU_x$TAGCACTGGCC$_x$U$_x$ | 20 | 18 | 41.5 |
| 05/402380 | $C_xU_x$TAGCACTGGCC$_x$U$_x$ | 40 | 22 | |
| 05/405837 | $C_yU_y$TAGCACTGGCC$_y$U$_y$ | 20 | 45 | 50.6 |
| 05/405837 | $C_yU_y$TAGCACTGGCC$_y$U$_y$ | 40 | 39 | |

All internucleoside linkages are phosphorothioate. Nucleosides not followed by a subscript are β-D-2'-deoxyribonucleosides. Nucleosides followed by a subscript are bicyclic nucleoside analogs having the formula and configuration:

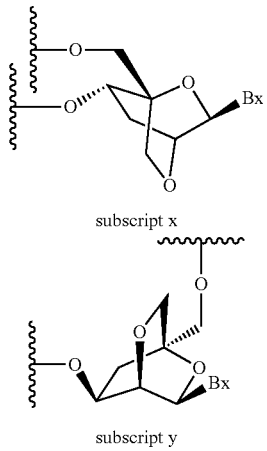

subscript x subscript y wherein Bx is the heterocyclic base.

---

What is claimed is:

1. A bicyclic nucleoside analog of Formula I:

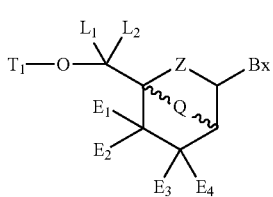

I wherein:
Bx is a heterocyclic base moiety;
Z is O;
Q is 5'-CR$_3$R$_4$—O-2', 5'-(CR$_3$R$_4$)$_2$-2', 5'-CR$_3$=CR$_4$-2', 5'-CR$_3$R$_4$—O—N(R$_5$)-2' or 5'-CR$_3$R$_4$—N(R$_5$)—O-2;
each R$_3$ and R$_4$ is, independently, H, C$_1$-C$_6$ alkyl, substituted C$_1$-C$_6$ alkyl, C$_1$-C$_6$ alkoxy, substituted C$_1$-C$_6$ alkoxy or halogen;
R$_5$ is H, C$_1$-C$_6$ alkyl, substituted C$_1$-C$_6$ alkyl, C$_1$-C$_6$ alkoxy or substituted C$_1$-C$_6$ alkoxy;
L$_1$ and L$_2$ are each H or one of L$_1$ and L$_2$ is H and the other of L$_1$ and L$_2$ is CH$_3$ or OCH$_3$;
one of E$_1$, E$_2$, E$_3$ and E$_4$ is O-T$_2$, two of E$_1$, E$_2$, E$_3$ and E$_4$ are H and the remaining one of E$_1$, E$_2$, E$_3$ and E$_4$ is H, halogen, C$_1$-C$_6$ alkyl or substituted C$_1$-C$_6$ alkyl;
one of T$_1$ and T$_2$ is H, a hydroxyl protecting group or a phosphorus moiety and the other of T$_1$ and T$_2$ is H, a hydroxyl protecting group or a reactive phosphorus group;
each substituted group comprises one or more optionally protected substituent groups independently selected from halogen, OJ$_5$, N(J$_5$)(J$_6$), =NJ$_5$, SJ$_5$, N$_3$, CN, OC(=L)J$_5$, OC(=L)N(J$_5$)(J$_6$) and C(=L)N(J$_5$)(J$_6$);
L is O, S or NJ$_7$; and
each J$_5$, J$_6$ and J$_7$ is, independently, H, C$_1$-C$_{12}$ alkyl, C$_2$-C$_{12}$ alkenyl, C$_2$-C$_{12}$ alkynyl, C$_5$-C$_{20}$ aryl or C$_1$-C$_{12}$ aminoalkyl.

2. The bicyclic nucleoside analog of claim 1 wherein Bx is uracil, thymine, cytosine, 5-methylcytosine, adenine or guanine.

3. The bicyclic nucleoside analog of claim 1 wherein three of E$_1$, E$_2$, E$_3$ and E$_4$ are H.

4. The bicyclic nucleoside analog of claim 1 wherein L$_1$ and L$_2$ are each H.

5. The bicyclic nucleoside analog of claim 1 wherein one of L$_1$ and L$_2$ is H and the other of L$_1$ and L$_2$ is CH$_3$.

6. The bicyclic nucleoside analog of claim 1 wherein T$_1$ is 4,4'-dimethoxytrityl and T$_2$ is diisopropylcyanoethoxy phosphoramidite.

7. The bicyclic nucleoside analog of claim 1 wherein Q is 5'-CR$_3$R$_4$—O-2' or 5'-(CR$_3$R$_4$)$_2$-2'.

8. The bicyclic nucleoside analog of claim 7 wherein each R$_3$ and R$_4$ is H.

9. The bicyclic nucleoside analog of claim 8 wherein Q is 5'-CH$_2$—O-2'.

10. The bicyclic nucleoside analog of claim 1 wherein said reactive phosphorus group is diisopropylcyanoethoxy phosphoramidite or H-phosphonate.

11. The bicyclic nucleoside analog of claim 1 wherein said phosphorus moiety has the formula:

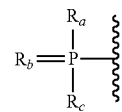

wherein:
R$_a$ and R$_c$ are each, independently, OH, SH, C$_1$-C$_6$ alkyl, substituted C$_1$-C$_6$ alkyl, C$_1$-C$_6$ alkoxy, substituted C$_1$-C$_6$ alkoxy, amino or substituted amino; and
R$_b$ is O or S.

12. The bicyclic nucleoside analog of claim 1 having the configuration of one of formulas Ia, Ib, Ic and Id:

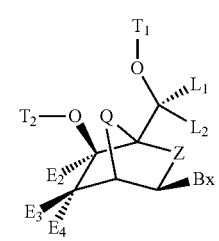

Ia

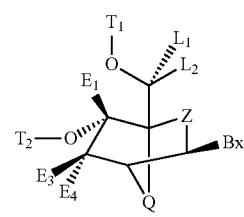

Ib

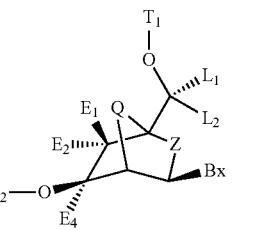

Ic and

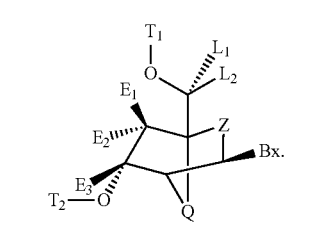

Id

13. An oligomeric compound comprising at least one bicyclic nucleoside analog of Formula II:

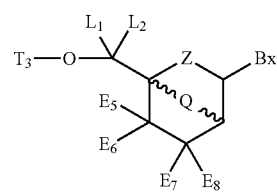

II wherein independently for each bicyclic nucleoside analog of formula II:
  Bx is a heterocyclic base moiety;
  Z is O;
  Q is 5'-$CR_3R_4$—O-2', 5'-$(CR_3R_4)_2$-2', 5'-$CR_3$=$CR_4$-2', 5'-$CR_3R_4$—O—N($R_5$)-2' or 5'-$CR_3R_4$—N($R_5$)—O-2;
  each $R_3$ and $R_4$ is, independently, H, $C_1$-$C_6$ alkyl, substituted $C_1$-$C_6$ alkyl, $C_1$-$C_6$ alkoxy, substituted $C_1$-$C_6$ alkoxy or halogen;
  $R_5$ is H, $C_1$-$C_6$ alkyl, substituted $C_1$-$C_6$ alkyl, $C_1$-$C_6$ alkoxy or substituted $C_1$-$C_6$ alkoxy;
  $L_1$ and $L_2$ are each H or one of $L_1$ and $L_2$ is H and the other of $L_1$ and $L_2$ is $CH_3$ or $OCH_3$;
  one of $E_4$, $E_5$, $E_6$ and $E_7$ is O-$T_4$, two of $E_4$, $E_5$, $E_6$ and $E_7$ are H and the remaining one of $E_4$, $E_5$, $E_6$ and $E_7$ is H, halogen, $C_1$-$C_6$ alkyl or substituted $C_1$-$C_6$ alkyl;
  one of $T_3$ and $T_4$ is an internucleoside linking group linking the bicyclic nucleoside analog to the oligomeric compound and the other of $T_3$ and $T_4$ is H, a protecting group, a phosphorus moiety, a 5' or 3'-terminal group or an internucleoside linking group linking the bicyclic nucleoside analog to the oligomeric compound;
  each substituted group comprises one or more optionally protected substituent groups independently selected from halogen, $OJ_5$, $N(J_5)(J_6)$, =$NJ_5$, $SJ_5$, $N_3$, CN, OC(=L)$J_5$, OC(=L)N($J_5$)($J_6$) and C(=L)N($J_5$)($J_6$);
  L is O, S or $NJ_7$; and
  each $J_5$, $J_6$ and $J_7$ is, independently, H, $C_1$-$C_{12}$ alkyl, $C_2$-$C_{12}$ alkenyl, $C_2$-$C_{12}$ alkynyl, $C_5$-$C_{20}$ aryl or $C_1$-$C_{12}$ aminoalkyl.

14. The oligomeric compound of claim 13 wherein independently for each bicyclic nucleoside analog of formula II, Bx is uracil, thymine, cytosine, 5-methylcytosine, adenine or guanine.

15. The oligomeric compound of claim 13 wherein independently for each bicyclic nucleoside analog of formula II, three of $E_5$, $E_6$, $E_7$ and $E_8$ are H.

16. The oligomeric compound of claim 13 wherein independently for each bicyclic nucleoside analog of formula II, $L_1$ and $L_2$ are each H.

17. The oligomeric compound of claim 13 wherein independently for each bicyclic nucleoside analog of formula II, one of $L_1$ and $L_2$ is H and the other of $L_1$ and $L_2$ is $CH_3$.

18. The oligomeric compound of claim 13 wherein each Q is 5'-$CR_3R_4$—O-2' or 5'-$(CR_3R_4)_2$-2'.

19. The oligomeric compound of claim 18 wherein each $R_3$ and $R_4$ is H.

20. The oligomeric compound of claim 19 wherein each Q is 5'-$CH_2$—O-2'.

21. The oligomeric compound of claim 13 wherein said phosphorus moiety has the formula:

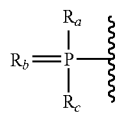

wherein:
  $R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and
  $R_b$ is O or S.

22. The oligomeric compound of claim 13 wherein each bicyclic nucleoside of Formula II has the configuration of one of formulas IIa, IIb, IIc and IId:

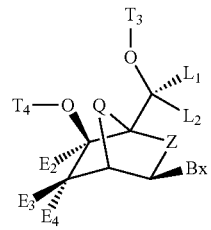

IIa

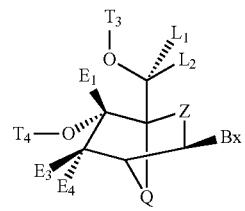

IIb

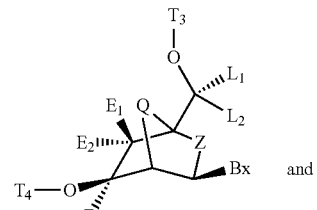

IIc and

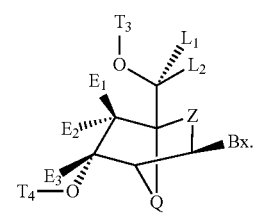

IId

23. The oligomeric compound of claim 22 comprising at least one region of from 2 to 5 contiguous bicyclic nucleoside analogs of formula II.

24. The oligomeric compound of claim 23 comprising a gapped oligomeric compound wherein one region of contiguous bicyclic nucleoside analogs of formula II is located at the 5'-end and a second region of contiguous bicyclic nucleoside analogs of formula II is located at the 3'-end, wherein the two regions are separated by an internal region comprising from about 6 to about 18 monomer subunits independently selected from nucleosides and modified nucleosides that are different from the bicyclic nucleoside analogs of formula II.

25. The oligomeric compound of claim 24 wherein said internal region comprises from about 8 to about 14 contiguous β-D-2'-deoxyribofuranosyl nucleosides.

26. The oligomeric compound of claim 13 wherein each internucleoside linking group is a phosphodiester or a phosphorothioate internucleoside linking group.

27. The oligomeric compound of claim 13 wherein essentially each internucleoside linking group is a phosphorothioate internucleoside linking group.

28. The oligomeric compound of claim 13 comprising from about 8 to about 40 monomer subunits in length.

29. A method of inhibiting gene expression comprising contacting one or more cells, a tissue or an animal with an oligomeric compound of claim 22.

* * * * *